United States Patent [19]
Martin

[11] Patent Number: 5,981,606
[45] Date of Patent: Nov. 9, 1999

[54] THERAPEUTIC TGF-BETA-WOUND HEALING COMPOSITIONS AND METHODS FOR PREPARING AND USING SAME

[75] Inventor: Alain Martin, Ringoes, N.J.

[73] Assignee: Warner-Lambert Company, Morris Plains, N.J.

[21] Appl. No.: 09/019,316

[22] Filed: Feb. 5, 1998

Related U.S. Application Data

[63] Continuation-in-part of application No. 08/053,922, Apr. 26, 1993, abandoned, which is a continuation of application No. 07/663,500, Mar. 1, 1991, abandoned, and a continuation of application No. 08/224,936, Apr. 8, 1994, abandoned
[60] Provisional application No. 60/037,730, Feb. 2, 1997.
[51] Int. Cl.$^6$ ................... A61K 31/045; A61K 31/07; A61K 31/355
[52] U.S. Cl. ................ 514/724; 514/725; 514/458; 514/946; 514/947
[58] Field of Search ..................... 514/724, 725, 514/458, 946, 947

[56] References Cited

U.S. PATENT DOCUMENTS 5,487,479 1/1996 Martin ........................ 514/724

Primary Examiner—Theodore J. Criares
Attorney, Agent, or Firm—Jean B. Barish

[57] ABSTRACT

This invention pertains to therapeutic wound healing compositions for protecting and resuscitating mammalian cells (Embodiment One (I)). This invention also pertains to therapeutic TGF-beta-wound healing compositions for reducing the formation of scar tissue and increasing the proliferation and resuscitation rate of mammalian cells (Embodiment Two (II)). In a first aspect of Embodiment One (I.A), the therapeutic wound healing composition comprises (a) pyruvate, (b) an antioxidant, and (c) a mixture of saturated and unsaturated fatty acids. In a second aspect of Embodiment One (I.B), the therapeutic wound healing composition comprises (a) pyruvate, (b) lactate, and (c) a mixture of saturated and unsaturated fatty acids. In a third aspect of Embodiment One (I.C), the therapeutic wound healing composition comprises (a) an antioxidant and (b) a mixture of saturated and unsaturated fatty acids. In a fourth aspect of Embodiment One (I.D), the therapeutic wound healing composition comprises (a) lactate, (b) an antioxidant, and (c) a mixture of saturated and unsaturated fatty acids. In Embodiment Two (II), the therapeutic wound healing compositions of Embodiment One (I.A–D) are combined with a therapeutically effective amount of a TGF-beta (GF) to form TGF-beta-wound healing compositions (II.A–D+GF). This invention also pertains to methods for preparing and using the TGF-beta-wound healing compositions and the topical and ingestible pharmaceutical products in which the therapeutic compositions may be used.

33 Claims, 8 Drawing Sheets

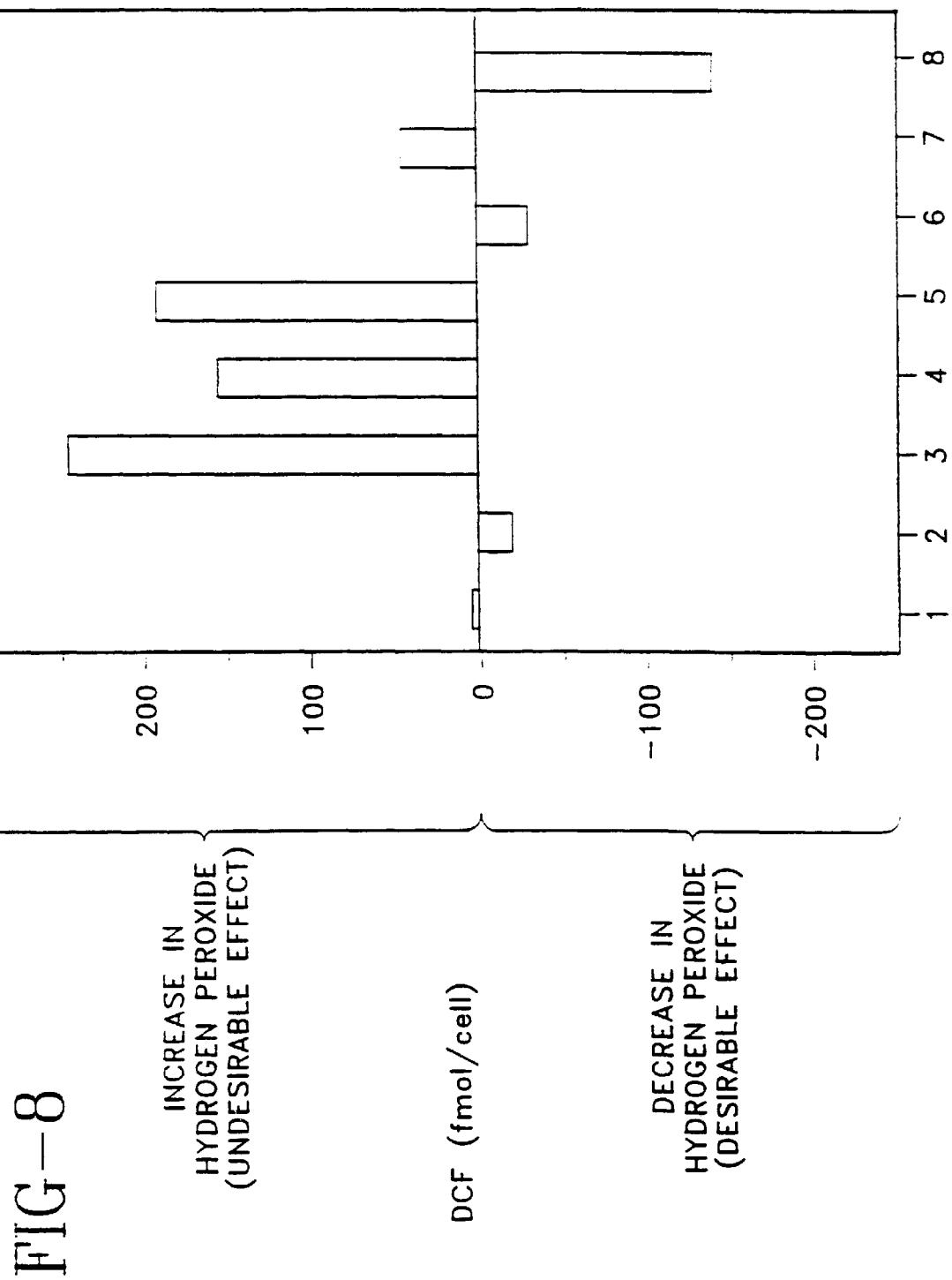

THERAPEUTIC TGF-BETA-WOUND HEALING COMPOSITIONS AND METHODS FOR PREPARING AND USING SAME

REFERENCE TO RELATED UNITED STATES APPLICATIONS

This application claims the benefit of U.S. Provisional Application No. 60/037,730 filed Feb. 2, 1997 and is a continuation-in-part of each of the following applications: (1) application Ser. No. 08/053,922, filed Apr. 26, 1993, abandoned, which application is a continuation of application Ser. No. 07/663,500, filed Mar. 1, 1991, now abandoned; (2) application Ser. No. 08/224,936, filed Apr. 8, 1994, abandoned. All of these applications are hereby incorporated by reference herein.

BACKGROUND OF THE INVENTION

1. Field of the Invention

This invention pertains to therapeutic wound healing compositions for protecting and resuscitating mammalian cells (Embodiment One (I)). This invention also pertains to therapeutic TGF-beta-wound healing compositions for reducing the formation of scar tissue and increasing the proliferation and resuscitation rate of mammalian cells (Embodirnent Two (II)).

In Embodiment One (I), the therapeutic wound healing compositions are used alone. In a first aspect of Embodiment One (I.A), the therapeutic wound healing composition comprises (a) pyruvate selected from the group consisting of pyruvic acid, pharmaceutically acceptable salts of pyruvic acid, and mixtures thereof, (b) an antioxidant, and (c) a mixture of saturated and unsaturated fatty acids wherein the fatty acids are those fatty acids required for the repair of cellular membranes and resuscitation of mammalian cells. In a second aspect of Embodiment One (I.B), the therapeutic wound healing composition comprises (a) pyruvate selected from the group consisting of pyruvic acid, pharmaceutically acceptable salts of pyruvic acid, and mixtures thereof, (b) lactate selected from the group consisting of lactic acid, pharmaceutically acceptable salts of lactic acid, and mixtures thereof, and (c) a mixture of saturated and unsaturated fatty acids wherein the fatty acids are those fatty acids required for the repair of cellular membranes and resuscitation of mammalian cells. In a third aspect of Embodiment One (I.C), the therapeutic wound healing composition comprises (a) an antioxidant and (b) a mixture of saturated and unsaturated fatty acids wherein the fatty acids are those fatty acids required for the repair of cellular membranes and resuscitation of mammalian cells. In a fourth aspect of Embodiment One (I.D), the therapeutic wound healing composition comprises (a) lactate selected from the group consisting of lactic acid, pharmaceutically acceptable salts of lactic acid, and mixtures thereof, (b) an antioxidant, and (c) a mixture of saturated and unsaturated fatty acids wherein the fatty acids are those fatty acids required for the repair of cellular membranes and resuscitation of mammalian cells.

In Embodiment Two (II), the therapeutic wound healing compositions of Embodiment One (I.A–D) are combined with a therapeutically effective amount of a TGF-beta (transforming growth factor-beta, GF) to form TGF-beta-wound healing compositions (II.A–D+GF). This invention also pertains to methods for preparing and using the TGF-beta-wound healing compositions and the topical and ingestible pharmaceutical products in which the therapeutic compositions may be used.

2. Description of the Background

Wound Healing

Wounds are internal or external bodily injuries or lesions caused by physical means, such as mechanical, chemical viral, bacterial, or thermal means, which disrupt the normal continuity of structures. Such bodily injuries include contusions, wounds in which the skin is unbroken, incisions, wounds in which the skin is broken by a cutting instrument, and lacerations, wounds in which the skin is broken by a dull or blunt instrument. Wounds may be caused by accidents or by surgical procedures. Patients who suffer major wounds could benefit from an enhancement in the wound healing process.

Wound healing consists of a series of processes whereby injured tissue is repaired, specialized tissue is regenerated, and new tissue is reorganized. Wound healing consists of three major phases: a) an inflammation phase (0–3 days), b) a cellular proliferation phase (3–12 days), and (c) a remodeling phase (3 days–6 months).

During the inflammation phase, platelet aggregation and clotting form a matrix which traps plasma proteins and blood cells to induce the influx of various types of cells. During the cellular proliferation phase, new connective or granulation tissue and blood vessels are formed. During the remodeling phase, granulation tissue is replaced by a network of collagen and elastin fibers leading to the formation of scar tissue.

When cells are injured or killed as a result of a wound, a wound healing step is desirable to resuscitate the injured cells and produce new cells to replace the dead cells. The healing process requires the reversal of cytotoxicity, the suppression of inflammation, and the stimulation of cellular viability and proliferation. Wounds require low levels of oxygen in the initial stages of healing to suppress oxidative damage and higher levels of oxygen in the later stages of healing to promote collagen formation by fibroblasts.

Mammalian cells are continuously exposed to activated oxygen species such as superoxide ($O_2$), hydrogen peroxide ($H_2O_2$), hydroxyl radical (OH), and singlet oxygen ($^1O_2$). In vivo, these reactive oxygen intermediates are generated by cells in response to aerobic metabolism, catabolism of drugs and other xenobiotics, ultraviolet and x-ray radiation, and the respiratory burst of phagocytic cells (such as white blood cells) to kill invading bacteria such as those introduced through wounds. Hydrogen peroxide, for example, is produced during respiration of most living organisms especially by stressed and injured cells.

These active oxygen species can injure cells. An important example of such damage is lipid peroxidation which involves the oxidative degradation of unsaturated lipids. Lipid peroxidation is highly detrimental to membrane structure and function and can cause numerous cytopathological effects. Cells defend against lipid peroxidation by producing radical scavengers such as superoxide dismutase, catalase, and peroxidase. Injured cells have a decreased ability to produce radical scavengers. Excess hydrogen peroxide can react with DNA to cause backbone breakage, produce mutations, and alter and liberate bases. Hydrogen peroxide can also react with pyrimidines to open the 5, 6-double bond, which reaction inhibits the ability of pyrimidines to hydrogen bond to complementary bases, Hallaender et al. (1971). Such oxidative biochemical injury can result in the loss of cellular membrane integrity, reduced enzyme activity, changes in transport kinetics, changes in membrane lipid content, and leakage of potassium ions, amino acids, and other cellular material.

Antioxidants have been shown to inhibit damage associated with active oxygen species. For example, pyruvate and other α-ketoacids have been reported to react rapidly and stoichiometrically with hydrogen peroxide to protect cells from cytolytic effects, O'Donnell-Tormey et al., J. Exp. Med., 165, pp. 500–514 (1987).

U.S. Pat. Nos. 3,920,835, 3,984,556, and 3,988,470, all issued to Van Scott et al., disclose methods for treating acne, dandruff, and palmar keratosis, respectively, which consist of applying to the affected area a topical composition comprising from about 1% to about 20% of a lower aliphatic compound containing from two to six carbon atoms selected from the group consisting of α-hydroxyacids, α-ketoacids and esters thereof, and 3-hydroxybutryic acid in a pharmaceutically acceptable carrier. The aliphatic compounds include pyruvic acid and lactic acid.

U.S. Pat. Nos. 4,105,783 and 4,197,316, both issued to Yu et al., disclose a method and composition, respectively, for treating dry skin which consists of applying to the affected area a topical composition comprising from about 1% to about 20% of a compound selected from the group consisting of amides and ammonium salts of α-hydroxyacids, β-hydroxyacids, and α-ketoacids in a pharmaceutically acceptable carrier. The compounds include the amides and ammonium salts of pyruvic acid and lactic acid.

U.S. Pat. No. 4,234,599, issued to Van Scott et al., discloses a method for treating actinic and nonactinic skin keratoses which consists of applying to the affected area a topical composition comprising an effective amount of a compound selected from the group consisting of α-hydroxyacids, β-hydroxyacids, and α-ketoacids in a pharmaceutically acceptable carrier. The acidic compounds include pyruvic acid and lactic acid.

U.S. Patent No. 4,294,852, issued to Wildnauer et al., discloses a composition for treating skin which comprises the α-hydroxyacids, βhydroxyacids, and α-ketoacids disclosed above by Van Scott et al. in combination with $C_3$–$C_8$ aliphatic alcohols.

U.S. Pat. No. 4,663,166, issued to Veech, discloses an electrolyte solution which comprises a mixture of L-lactate and pyruvate in a ratio from 20:1 to 1:1, respectively, or a mixture of D-β-hydroxybutyrate and acetoacetate, in a ratio from 6:1 to 0.5: 1, respectively.

Sodium pyruvate has been reported to reduce the number of erosions, ulcers, and hemorrhages on the gastric mucosa in guinea pigs and rats caused by acetylsalicylic acid. The analgesic and antipyretic properties of acetylsalicylic acid were not impaired by sodium pyruvate, Puschmann, Arzneimittelforschung, 33, pp. 410–415 and 415–416 (1983).

Pyruvate has been reported to exert a positive inotropic effect in stunned myocardum, which is a prolonged ventricular dysfunction following brief periods of coronary artery occlusions which does not produce irreversible damage, Mentzer et al., Ann. Surg., 209, pp. 629–633 (1989).

Pyruvate has been reported to produce a relative stabilization of left ventricular pressure and work parameter and to reduce the size of infarctions. Pyruvate improves resumption of spontaneous beating of the heart and restoration of normal rates and pressure development, Bunger et al., J. Mol. Cell. Cardiol., 18, pp. 423–438 (1986), Mochizuki et al., J. Physiol. (Paris), 76, pp. 805–812 (1980), Regitz et al., Cardiovasc. Res., 15, pp. 652–658 (1981), Giannelli et al., Ann. Thorac. Surg., 21, pp. 386–396 (1976).

Sodium pyruvate has been reported to act as an antagonist to cyanide intoxication (presumably through the formation of a cyanohydrin) and to protect against the lethal effects of sodium sulfide and to retard the onset and development of functional morphological and biochemical measures of acrylamide neuropathy of axons, Schwartz et al., Toxicol. Appl. Pharmacol., 50, pp. 437–442 (1979), Sabri et al., Brain Res., 483, pp. 1–11 (1989).

A chemotherapeutic cure of advanced L1210 leukemia has been reported using sodium pyruvate to restore abnormally deformed red blood cells to normal. The deformed red blood cells prevented adequate drug delivery to tumor cells, Cohen, Cancer Chemother. Pharmacol., 5, pp. 175–179 (1981).

Primary cultures of heterotopic tracheal transplant exposed in vivo to 7, 12-dimethyl-benz(a)anthracene were reported to be successfully maintained in enrichment medium supplemented with sodium pyruvate along with cultures of interleukin-2 stimulated peripheral blood lymphocytes, and plasmacytomas and hybridomas, pig embryos, and human blastocysts, Shacter, J. Immunol. Methods, 99, pp. 259–270 (1987), Marchok et al., Cancer Res., 37, pp. 1811–1821 (1977), Davis, J. Reprod. Fertil. Suppl., 33, pp. 115–124 (1985), Okamoto et al., No To Shinkei, 38, pp.593–598 (1986), Cohen et al., J. In Vitro Fert. Embryo Transfer, 2, pp. 59–64 (1985).

U.S. Pat. Nos. 4,158,057, 4,351,835, 4,415,576, and 4,645,764, all issued to Stanko, disclose methods for preventing the accumulation of fat in the liver of a mammal due to the ingestion of alcohol, for controlling weight in a mammal, for inhibiting body fat while increasing protein concentration in a mammal, and for controlling the deposition of body fat in a living being, respectively. The methods comprise administering to the mammal a therapeutic mixture of pyruvate and dihydroxyacetone, and optionally riboflavin. U.S. Pat. No. 4,548,937, issued to Stanko, discloses a method for controlling the weight gain of a mammal which comprises administering to the mammal a therapeutically effective amount of pyruvate, and optionally riboflavin. U.S. Pat. No. 4,812,479, issued to Stanko, discloses a method for controlling the weight gain of a mammal which comprises administering to the mammal a therapeutically effective amount of dihydroxyacetone, and optionally riboflavin and pyruvate.

Rats fed a calcium-oxalate lithogenic diet including sodium pyruvate were reported to develop fewer urinary calculi (stones) than control rats not given sodium pyruvate, Ogawa et al., Hinyokika Kiyo, 32, pp. 1341–1347 (1986).

U.S. Pat. No. 4,521,375, issued to Houlsby, discloses a method for sterilizing surfaces which come into contact with living tissue. The method comprises sterilizing the surface with aqueous hydrogen peroxide and then neutralizing the surface with pyruvic acid.

U.S. Pat. No. 4,416,982, issued to Tauda et al., discloses a method for decomposing hydrogen peroxide by reacting the hydrogen peroxide with a phenol or aniline derivative in the presence of peroxidase.

U.S. Pat. No. 4,696,917, issued to Lindstrom et al., discloses an eye irrigation solution which comprises Eagle's Minimum Essential Medium with Earle's salts, chondroitin sulfate, a buffer solution, 2-mercaptoethanol, and a pyruvate. The irrigation solution may optionally contain ascorbic acid and α-tocopherol. U.S. Pat. No. 4,725,586, issued to Lindstrom et al., discloses an irrigation solution which comprises a balanced salt solution, chondroitin sulfate, a buffer solution, 2-mercaptoethanol, sodium bicarbonate or dextrose, a pyruvate, a sodium phosphate buffer system, and cystine. The irrigation solution may optionally contain ascorbic acid and γ-tocopherol.

U.S. Pat. No. 3,887,702 issued to Baldwin, discloses a composition for treating fingernails and toenails which consists essentially of soybean oil or sunflower oil in combination with Vitamin E.

U.S. Pat. No. 4,847,069, issued to Bissett et al., discloses a photoprotective composition comprising (a) a sorbohydroxamic acid, (b) an anti-inflammatory agent selected from steroidal anti-inflammatory agents and a natural anti-inflammatory agent, and (c) a topical carrier. Fatty acids may be present as an emollient. U.S. Pat. No. 4,847,071, issued to Bissett et al., discloses a photoprotective composition comprising (a) a tocopherol or tocopherol ester radical scavenger, b) an anti-inflammatory agent selected from steroidal anti-inflammatory agents and a natural anti-inflammatory agent, and (c) a topical carrier. U.S. Pat. No. 4,847,072, issued to Bissett et al., discloses a topical composition comprising not more than 25% tocopherol sorbate in a topical carrier.

U.S. Pat. No. 4,533,637, issued to Yamane et al., discloses a culture medium which comprises a carbon source, a nucleic acid source precursor, amino acids, vitamins, minerals, a lipophilic nutrient, and serum albumin, and cyclodextrins. The lipophilic substances include unsaturated fatty acids and lipophilic vitamins such as Vitamin A, D, and E. Ascorbic acid may also be present.

United Kingdom patent application no.2,196,348A, to Kovar et al., discloses a synthetic culture medium which comprises inorganic salts, monosaccharides, amino acids, vitamins, buffering agents, and optionally sodium pyruvate adding magnesium hydroxide or magnesium oxide to the emulsion. The oil phase may include chicken fat.

U.S. Patent No. 4,284,630, issued to Yu et al., discloses a method for stabilizing a water-in-oil emulsion which comprises adding magnesium hydroxide or magnesium oxide to the emulsion. The oil phase may include chicken fat.

PREPARATION H® has been reported to increase the rate of wound healing in artificially created rectal ulcers. The active ingredients in PREPARATION H® are skin respiratory factor and shark liver oil Subramanyam et al., Digestive Diseases and Sciences, 29, pp. 829–832 (1984).

The addition of sodium pyruvate to bacterial and yeast systems has been reported to inhibit hydrogen peroxide production, enhance growth, and protect the systems against the toxicity of reactive oxygen intermediates. The unsaturated fatty acids and saturated fatty acids contained within chicken fat enhanced membrane repair and reduced cytotoxicity. The antioxidants glutathione and thioglycollate reduced the injury induced by oxygen radical species, Martin, Ph.D. thesis, (1987–89).

U.S. Pat. No. 4,615,697, issued to Robinson, discloses a controlled release treatment composition comprising a treating agent and a TGF-beta comprising a water-swellable but water-insoluble, fibrous cross-linked carboxy-functional polymer.

European patent application no. 0410696A1, to Kellaway et al., discloses a mucoadhesive delivery system comprising a treating agent and a polyacrylic acid cross-linked with from about 1% to about 20% by weight of a polyhydroxy compound such as a sugar, cyclitol, or lower polyhydric alcohol.

Transforming Growth Factor-beta

Human transforming growth factor-beta (TGF-beta, TGF-β) has been isolated from human blood platelets and placenta and purified to essential homogeneity using sequential gel filtration cation-exchange chromatography and high performance liquid chromatography. The purified protein has been characterized as having a molecular weight of 25,000 daltons and composed of 2 sub-units of 12,500 daltons each held together by disulfide bonds. The molecular weight, sub-unit structure and amino acid composition of the purified protein differed from that of platelet derived growth factor. European Patent Application EP 128849 (Dec. 19, 1984).

TGF-beta has also been purified from platelets or conditioned media utilizing acid ethanol extraction, cation-exchange separation on the extract, and hydrophobic separations on the active fractions to obtain a homogenous preparation. The purified product is said to be useful in wound healing and tissue repair. European Patent Application EP322842-A (Jul. 12, 1989).

TGF-beta has also been prepared utilizing recombinant DNA, wherein the cloned human gene coding for TGF-beta was inserted into eukaryotic cell lines for expression. The protein product was said to be useful in promoting anchorage-dependent independent growth in cell culture. JP61219395 (Sep. 29, 1980) and JP63028386 (Feb. 6, 1988).

A composition containing purified insulin-like growth factor and TGF-beta in ratios of 1:4 to 25:1 is disclosed to be useful in wound healing. PCT application WO 8911293-A (Nov. 30, 1989).

U.S. Pat. No. 5,147,854 discloses that the therapeutic activity of transforming growth factor-beta is enhanced when it is used in combination with a synergistically effective amount of a polyunsaturated fatty acid.

While the above therapeutic wound healing compositions are reported to inhibit the production of reactive oxygen intermediates, none of the above compositions are entirely satisfactory. None of the compositions has the ability to simultaneously decrease cellular levels of hydrogen peroxide production, increase cellular resistance to cytotoxic agents, increase rates of cellular proliferation, increase cellular viability to protect and resuscitate mammalian cells, and reduce the formation of scar tissue. The present invention provides such improved therapeutic TGF-beta-wound healing compositions without the disadvantages characteristic of previously known compositions. This invention also relates to methods for preparing and using the therapeutic TGF-beta-wound healing compositions and the topical and ingestible pharmaceutical products in which the therapeutic compositions may be used.

SUMMARY OF THE INVENTION

This invention pertains to therapeutic wound healing compositions for protecting and resuscitating mammalian cells (Embodiment One (I)). This invention also pertains to therapeutic TGF-beta-wound healing compositions for reducing the formation of scar tissue and increasing the proliferation and resuscitation rate of mammalian cells (Embodiment Two (II)).

In Embodiment One (I), the therapeutic wound healing compositions are used alone. In a first aspect of Embodiment One (I.A), the therapeutic wound healing composition comprises (a) pyruvate selected from the group consisting of pyruvic acid, pharmaceutically acceptable salts of pyruvic acid, and mixtures thereof, (b) an antioxidant, and (c) a mixture of saturated and unsaturated fatty acids wherein the fatty acids are those fatty acids required for the repair of cellular membranes and resuscitation of mammalian cells. In a second aspect of Embodiment One (I.B), the therapeutic wound healing composition comprises (a) pyruvate selected from the group consisting of pyruvic acid, pharmaceutically acceptable salts of pyruvic acid, and mixtures thereof, (b) lactate selected from the group consisting of lactic acid, pharmaceutically acceptable salts of lactic acid, and mixtures thereof, and (c) a mixture of saturated and unsaturated fatty acids wherein the fatty acids are those fatty acids required for the repair of cellular membranes and resuscitation of mammalian cells. In a third aspect of Embodiment One (I.C), the therapeutic wound healing composition comprises (a) an antioxidant and (b) a mixture of saturated and unsaturated fatty acids wherein the fatty acids are those fatty acids required for the repair of cellular membranes and resuscitation of mammalian cells. In a fourth aspect of Embodiment One (I.D), the therapeutic wound healing composition comprises (a) lactate selected from the group consisting of lactic acid, pharmaceutically acceptable salts of lactic acid, and mixtures thereof, (b) an antioxidant, and (c) a mixture of saturated and unsaturated fatty acids wherein the fatty acids are those fatty acids required for the repair of cellular membranes and resuscitation of mammalian cells.

Preferably, the wound healing composition comprises (I.A):

(a) pyruvate selected from the group consisting of pyruvic acid, pharmaceutically acceptable salts of pyruvic acid, and mixtures thereof, (b) an antioxidant; and (c) a mixture of saturated and unsaturated fatty acids wherein the fatty acids are those fatty acids required for the repair of cellular membranes and resuscitation of mammalian cells.

In Embodiment Two (II), the therapeutic wound healing compositions of Embodiment One (I.A–D) are combined with a therapeutically effective amount of a TGF-beta (GF) to form TGF-beta-wound healing compositions (II.A–D+GF). The TGF-befa-wound healing compositions may be used alone or in combination with other medicaments. This invention also pertains to methods for preparing and using the TGF-beta-wound healing compositions and the topical and ingestible pharmaceutical products in which the therapeutic compositions may be used.

Preferably, the therapeutic TGF-beta-wound healing composition (II.A–D+GF) comprises a therapeutically effective amount of a TGF-beta and a wound healing composition, wherein the wound healing composition comprises:

(a) pyruvate selected from the group consisting of pyruvic acid, pharmaceutically acceptable salts of pyruvic acid, and mixtures thereof;

(b) an antioxidant; and (c) a mixture of saturated and unsaturated fatty acids wherein the fatty acids are those fatty acids required for the resuscitation of injured mammalian cells; wherein components a, b, and c are present in amounts sufficient to enhance wound healing.

BRIEF DESCRIPTION OF THE FIGURES

FIG. 8 depicts in bar graph format a summary analysis of the levels of hydrogen peroxide produced by epidermal keratinocytes following exposure of the cells to the individual components of the wound healing composition, to various combinations of the wound healing composition, and to the wound healing composition.

DETAILED DESCRIPTION OF THE INVENTION

Figure 1:
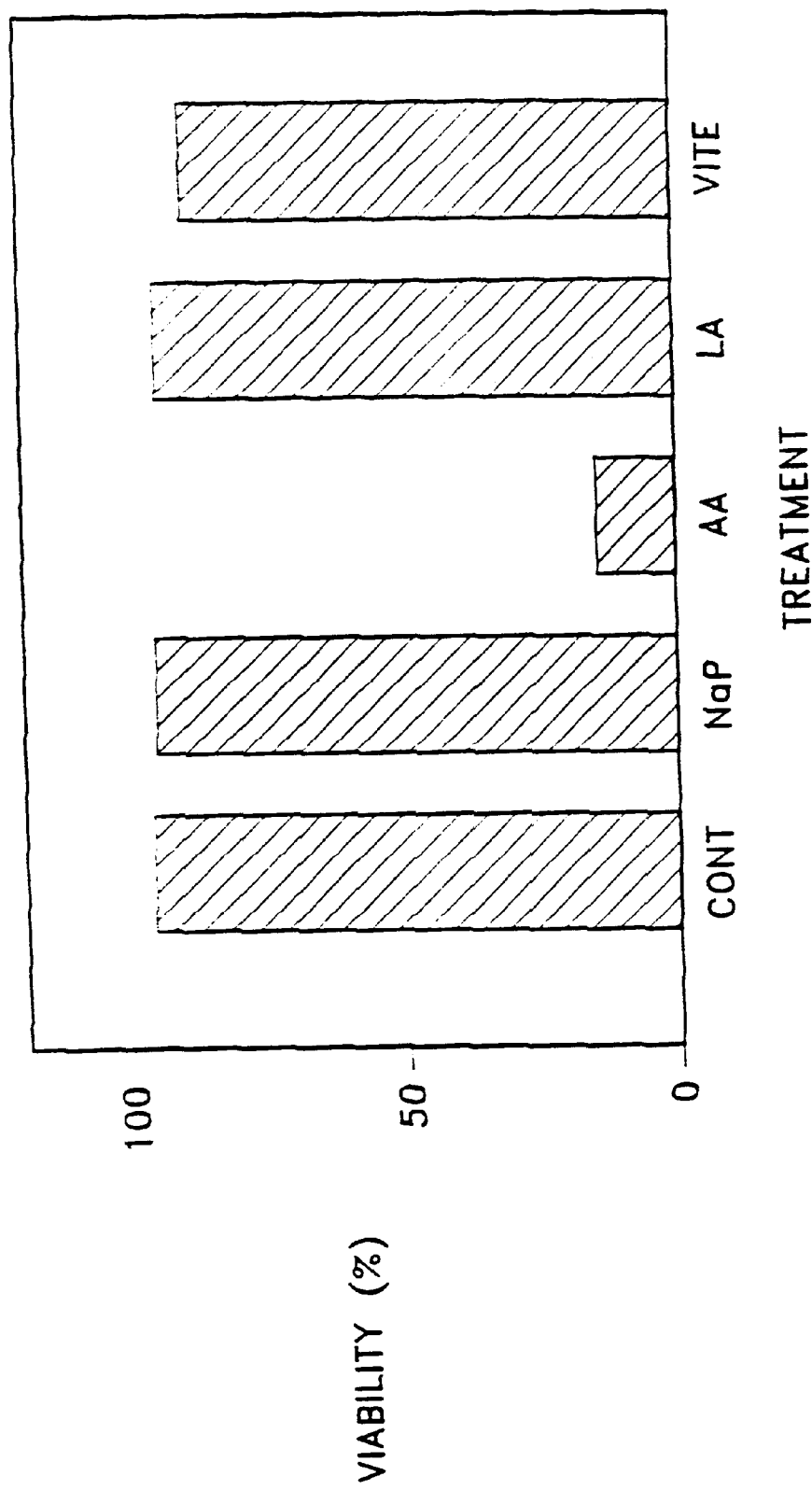
FIG. 1 depicts in bar graph format the viability of U937 monocytic cells following exposure of the cells to various antioxidants (Examples 1–5).

This invention pertains to therapeutic wound healing compositions for protecting and resuscitating mammalian cells (Embodiment One (I)). This invention also pertains to therapeutic TGF-beta-wound healing compositions for reducing the formation of scar tissue and increasing the proliferation and resuscitation rate of mammalian cells Embodiment Two (II).

In Embodiment One (I), the therapeutic wound healing compositions are used alone. In a first aspect of Embodiment One (I.A), the therapeutic wound healing composition comprises (a) pyruvate selected from the group consisting of pyruvic acid, pharmaceutically acceptable salts of pyruvic acid, and mixtures thereof (b) an antioxidant, and (c) a mixture of saturated and unsaturated fatty acids wherein the fatty acids are those fatty acids required for the repair of cellular membranes and resuscitation of mammalian cells. In a second aspect of Embodiment One (I.B), the therapeutic wound healing composition comprises (a) pyruvate selected from the group consisting of pyruvic acid, pharmaceutically acceptable salts of pyruvic acid, and mixtures thereof (b) lactate selected from the group consisting of lactic acid, pharmaceutically acceptable salts of lactic acid, and mixtures thereof and (c) a mixture of saturated and unsaturated fatty acids wherein the fatty acids are those fatty acids required for the repair of cellular membranes and resuscitation of mammalian cells. In a third aspect of Embodiment One (I.C), the therapeutic wound healing composition comprises (a) an antioxidant and (b) a mixture of saturated and unsaturated fatty acids wherein the fatty acids are those fatty acids required for the repair of cellular membranes and resuscitation of mammalian cells. In a fourth aspect of Embodiment One (I.D), the therapeutic wound healing composition comprises (a) lactate selected from the group consisting of lactic acid, pharmaceutically acceptable salts of lactic acid, and mixtures thereof, (b) an antioxidant, and (c) a mixture of saturated and unsaturated fatty acids wherein the fatty acids are those fatty acids required for the repair of cellular membranes and resuscitation of mammalian cells.

Preferably, the wound healing composition comprises (I.A):

(a) pyruvate selected from the group consisting of pyruvic acid, pharmaceutically acceptable salts of pyruvic acid, and mixtures thereof;

(b) an antioxidant; and (c) a mixture of saturated and unsaturated fatty acids wherein the fatty acids are those fatty acids required for the repair of cellular membranes and resuscitation of mammalian cells.

In Embodiment Two (II), the therapeutic wound healing compositions of Embodiment One (I.A–D) are combined with a therapeutically effective amount of a TGF-beta (GF) to form TGF-beta-wound healing compositions (II.A–D+GF). The TGF-beta-wound healing compositions may be used alone or in combination with other medicaments. This invention also pertains to methods for preparing and using the TGF-beta-wound healing compositions and the topical and ingestible pharmaceutical products in which the therapeutic compositions may be used.

As set out above, applicant has discovered therapeutic TGF-beta-wound healing compositions (II.A–D+GF) which comprise a therapeutically effective amount of a TGF-beta (GF) and the wound healing compositions of Embodiment One (I.A–D). TGF-betas can reduce the formation of scar tissue in a patient but do not promote the wound healing process. Wound healing compositions can increase the resuscitation rate of injured mammalian cells and the proliferation rate of new mammalian cells to replace dead cells but do not reduce the formation of scar tissue. Applicant believes that the combination of a TGF-beta and a wound healing composition results in a therapeutic TGF-beta-wound healing composition which reduces the formation of scar tissue following trauma such as in surgical procedures, especially eye surgery. Cells treated with the therapeutic wound healing compositions of the present invention show decreased levels of hydrogen peroxide production, increased resistance to cytotoxic agents, increased rates of proliferation, and increased viability. Cellular cultures containing the therapeutic wound healing compositions showed enhanced differentiation and proliferation over control cultures and rapidly formed attachments or tight junctions between the cells to form an epidermal sheet. Wounded mammals treated with the therapeutic TGF-beta-wound healing compositions would show significantly improved wound closing and healing over untreated mammals and mammals treated with conventional healing compositions.

The combination of the TGF-beta and the wound healing compositions of the present invention provides a pharmaceutical composition useful for reducing the formation of scar tissue and having an enhanced ability to prevent and reduce injury to mammalian cells and further increase the resuscitation rate of injured mammalian cells. The tissue damage associated with many traumas such as surgeries is believed to be caused by the production of cellular produced active oxygen species. Combination of the TGF-beta and the wound healing compositions may suppress such reactive oxygen-linked tissue injury.

The term "injured cell" as used herein means a cell that has any activity disrupted for any reason. For example, an injured cell may be a cell that has injured membranes or damaged DNA, RNA, and ribosomes, for example, a cell which has (a) injured membranes so that transport through the membranes is diminished resulting in an increase in toxins and normal cellular wastes inside the cell and a decrease in nutrients and other components necessary for cellular repair inside the cell, (b) an increase in concentration of oxygen radicals inside the cell because of the decreased ability of the cell to produce antioxidants and enzymes, or (c) damaged DNA, RNA, and ribosomes which must be repaired or replaced before normal cellular functions can be resumed. The term "resuscitation" of injured mammalian cells as used herein means the reversal of cytotoxicity, the stabilization of the cellular membrane, an increase in the proliferation rate of the cell, and/or the normalization of cellular functions such as the secretion of growth factors, hormones, and the like. The term "cytotoxicity" as used herein means a condition caused by a cytotoxic agent that injures the cell. Injured cells do not proliferate because injured cells expend all energy on cellular repair. Aiding cellular repair promotes cellular proliferation.

The term "prodrug", as used herein, refers to compounds which undergo biotransformation prior to exhibiting their pharmacological effects. The chemical modification of drugs to overcome pharmaceutical problems has also been termed "drug latentiation." Drug latentiation is the chemical modification of a biologically active compound to form a new compound which upon in vivo enzymatic attack will liberate the parent compound. The chemical alterations of the parent compound are such that the change in physicochemical properties will affect the absorption, distribution and enzymatic metabolism. The definition of drug latentiation has also been extended to include nonenzymatic regeneration of the parent compound. Regeneration takes place as a consequence of hydrolytic, dissociative, and other reactions not necessarily enzyme mediated. The terms prodrugs, latentiated drugs, and bioreversible derivatives are used interchangeably. By inference, latentiation implies a time lag element or time component involved in regenerating the bioactive parent molecule in vivo. The term prodrug is general in that it includes latentiated drug derivatives as well as those substances which are converted after administration to the actual substance which combines with receptors. The term prodrug is a generic term for agents which undergo biotransformation prior to exhibiting their pharmacological actions. In the case where the administered drug is not the active agent, but rather is biotransformed to the active agent, the term "prodrug" also includes compounds which may not necessarily undergo biotransformation to the administered drug but may undergo biotransformation to the active agent which exhibits the desired pharmacological effect.

1. Wound Healing Compositions

A. Embodiment One (I.A–D)

The cells which may be treated with the therapeutic wound healing compositions in the present invention are mammalian cells. Although applicant will describe the present therapeutic wound healing compositions as useful for treating mammalian epidermal keratinocytes and mammalian monocytes, applicant contemplates that the therapeutic wound healing compositions may be used to protect or resuscitate all mammalian cells. Keratinocytes are representative of normal mammalian cells and are the fastest proliferating cells in the body. The correlation between the reaction of keratinocytes to injury and therapy and that of mammalian cells in general is very high. Monocytes are representative of specialized mammalian cells such as the white blood cells in the immune system and the organ cells in liver, kidney, heart, and brain. The mammalian cells may be treated in vivo and in vitro.

Epidermal keratinocytes are the specialized epithelial cells of the epidermis which synthesize keratin, a sclerotein which is the principal constituent of epidermis, hair, nails, horny tissue, and the organic matrix of the enamel of teeth. Mammalian epidermal keratinocytes constitute about 95% of the epidermal cells and together with melanocytes form the binary system of the epidermis. In its various successive stages, epidermal keratinocytes are also known as basal cells, prickle cells, and granular cells.

Monocytes are mononuclear phagocytic leukocytes which undergo respiratory bursting and are involved in reactive oxygen mediated damage within the epidermis. Leukocytes are white blood cells or corpuscles which may be classified into two main groups: granular leukocytes (granulocytes) which are leukocytes with abundant granules in the cytoplasm and nongranular leukocytes (nongranulocytes) which are leukocytes without specific granules in the cytoplasm and which include the lymphocytes and monocytes. Phagocyte cells are cells which ingest microorganisms or other cells and foreign particles. Monocytes are also known as large mononuclear leukocytes, and hyaline or transitional leukocytes.

Epidermal keratinocyfic cells and monocytic cells have multiple oxygen generating mechanisms and the degree to which each type of mechanism functions differs in each type of cell. In monocytes, for example, the respiratory bursting process is more pronounced than in epidermal keratinocytes. Hence, the components in the therapeutic wound healing compositions of the present invention may vary depending upon the types of cells involved in the condition being treated.

As set out above, in a first aspect of Embodiment One (I.A), the therapeutic wound healing composition for treating mammalian cells, preferably epidermal keratinocytes, comprises (a) pyruvate selected from the group consisting of pyruvic acid, pharmaceutically acceptable salts of pyruvic acid, and mixtures thereof, (b) an antioxidant, and (c) a mixture of saturated and unsaturated fatty acids wherein the fatty acids are those fatty acids required for the repair of cellular membranes and resuscitation of mammalian cells. In a second aspect of Embodiment One (I.B), the therapeutic wound healing composition for treating mammalian cells, preferably epidermal keratinocytes, comprises (a) pyruvate selected from the group consisting of pyruvic acid, pharmaceutically acceptable salts of pyruvic acid, and mixtures thereof, (b) lactate selected from the group consisting of lactic acid, pharmaceutically acceptable salts of lactic acid, and mixtures thereof and (c) a mixture of saturated and unsaturated fatty acids wherein the fatty acids are those fatty acids required for the repair of cellular membranes and resuscitation of mammalian cells. In a third aspect of Embodiment One (I.C), the therapeutic wound healing composition for treating mammalian cells, preferably epidermal keratinocytes, comprises (a) an antioxidant and (b) a mixture of saturated and unsaturated fatty acids wherein the fatty acids are those fatty acids required for the repair of cellular membranes and resuscitation of mammalian cells. In a fourth aspect of Embodiment One (I.D), the therapeutic wound healing composition for treating mammalian cells, preferably monocytes, comprises (a) lactate selected from the group consisting of lactic acid, pharmaceutically acceptable salts of lactic acid, and mixtures thereof, (b) an antioxidant, and (c) a mixture of saturated and unsaturated fatty acids wherein the fatty acids are those fatty acids required for the repair of cellular membranes and resuscitation of mammalian cells.

Pyruvic acid (2-oxopropanoic acid, α-ketopropionic acid, $CH_3COCOOH$) or pyruvate is a fundamental intermediate in protein and carbohydrate metabolism and in the citric acid cycle. The citric acid cycle (tricarboxylic acid cycle, Kreb's cycle) is the major reaction sequence which executes the reduction of oxygen to generate adenosine triphosphate (ATP) by oxidizing organic compounds in respiring tissues to provide electrons to the transport system. Acetyl coenzyme A ("active acetyl") is oxidized in this process and is thereafter utilized in a variety of biological processes and is a precursor in the biosynthesis of many fatty acids and sterols. The two major sources of acetyl coenzyme A are derived from the metabolism of glucose and fatty acids. Glycolysis consists of a series of transformations wherein each glucose molecule is transformed in the cellular cytoplasm into two molecules of pyruvic acid. Pyruvic acid may then enter the mitochondria where it is oxidized by coenzyme A in the presence of enzymes and cofactors to acetyl coenzyme A. Acetyl coenzyme A can then enter the citric acid cycle.

In muscle, pyruvic acid (derived from glycogen) can be reduced to lactic acid during anaerobic metabolism which can occur during exercise. Lactic acid is reoxidized and partially retransformed to glycogen during rest. Pyruvate can also act as an antioxidant to neutralize oxygen radicals in the cell and can be used in the multifunction oxidase system to reverse cytotoxicity.

The pyruvate in the present invention may be selected from the group consisting of pyruvic acid, pharmaceutically acceptable salts of pyruvic acid, prodrugs of pyruvic acid, and mixtures thereof. In general, the pharmaceutically acceptable salts of pyruvic acid may be alkali salts and alkaline earth salts. Preferably, the pyruvate is selected from the group consisting of pyruvic acid, lithium pyruvate, sodium pyruvate, potassium pyruvate, magnesium pyruvate, calcium pyruvate, zinc pyruvate, manganese pyruvate, methyl pyruvate, α-ketoglutaric acid, and mixtures thereof. More preferably, the pyruvate is selected from the group of salts consisting of sodium pyruvate, potassium pyruvate, magnesium pyruvate, calcium pyruvate, zinc pyruvate, manganese pyruvate, and the like, and mixtures thereof. Most preferably, the pyruvate is sodium pyruvate.

The amount of pyruvate present in the therapeutic wound healing compositions of the present invention is a therapeutically effective amount. A therapeutically effective amount of pyruvate is that amount of pyruvate necessary for the inventive composition to prevent and reduce injury to mammalian cells or increase the resuscitation rate of injured mammalian cells. The exact amount of pyruvate is a matter of preference subject to such factors as the type of condition being treated as well as the other ingredients in the composition. In a preferred embodiment, pyruvate is present in the therapeutic wound healing composition in an amount from about 10% to about 50%, preferably from about 20% to about 45%, and more preferably from about 25% to about 40%, by weight of the therapeutic wound healing composition.

L-Lactic acid ((S)-2-hydroxypropanoic acid, (+) α-hydroxypropionic acid, $CH_3CHOHCOOH$) or lactate occurs in small quantities in the blood and muscle fluid of mammals. Lactic acid concentration increases in muscle and blood after vigorous activity. Lactate is a component in the cellular feedback mechanism and inhibits the natural respiratory bursting process of cells thereby suppressing the production of oxygen radicals.

The lactate in the present invention may be selected from the group consisting of lactic acid, pharmaceutically acceptable salts of lactic acid, prodrugs of lactic acid, and mixtures thereof. In general, the pharmaceutically acceptable salts of lactic acid may be alkali salts and alkaline earth salts. Preferably, the lactate is selected from the group consisting of lactic acid, lithium lactate, sodium lactate, potassium lactate, magnesium lactate, calcium lactate, zinc lactate, manganese lactate, and the like, and mixtures thereof. More preferably, the lactate is selected from the group consisting of lactic acid, sodium lactate, potassium lactate, magnesium lactate, calcium lactate, zinc lactate, manganese lactate, and mixtures thereof. Most preferably, the lactate is lactic acid.

The amount of lactate present in the therapeutic wound healing compositions of the present invention is a therapeutically effective amount. A therapeutically effective amount of lactate is that amount of lactate necessary for the inventive composition to prevent and reduce injury to mammalian cells or increase the resuscitation rate of injured mammalian cells. For an ingestible composition, a therapeutically effective amount of lactate is that amount necessary to suppress the respiratory bursting process of white blood cells to protect and resuscitate the mammalian cells. In general, a therapeutically effective amount of lactate in an ingestible composition is from about 5 to about 10 times the amount of lactate normally found in serum. The exact amount of lactate is a matter of preference subject to such factors as the type of condition being treated as well as the other ingredients in the composition. In a preferred embodiment, lactate is present in the therapeutic wound healing composition in an amount from about 10% to about 50%, preferably from about 20% to about 45%, and more preferably from about 25% to about 40%, by weight of the therapeutic wound healing composition.

Antioxidants are substances which inhibit oxidation or suppress reactions promoted by oxygen or peroxides. Antioxidants, especially lipid-soluble antioxidants, can be absorbed into the cellular membrane to neutralize oxygen radicals and thereby protect the membrane. The antioxidants useful in the present invention may be selected from the group consisting of all forms of Vitamin A (retinol), all forms of Vitamin $A_2$ (3,4-didehydroretinol), all forms of carotene such as $\alpha$-carotene, $\beta$-carotene (beta,$\beta$-carotene), $\gamma$-carotene, $\delta$-carotene, all forms of Vitamin C (D-ascorbic acid, L-ascorbic acid), all forms of tocopherol such as Vitamin E ($\alpha$-tocopherol, 3,4-dihydro-2,5,7,8-tetramethyl-2-(4,8,12-trimethyltri-decyl)-2H-1-benzopyran-6-ol), $\beta$-tocopherol, $\gamma$-tocopherol $\delta$-tocopherol, tocoquinone, tocotrienol, and Vitamin E esters which readily undergo hydrolysis to Vitamin E such as Vitamin E acetate and Vitamin E succinate, and pharmaceutically acceptable Vitamin E salts such as Vitamin E phosphate, prodrugs of Vitamin A, carotene, Vitamin C, and Vitamin E, pharmaceutically acceptable salts of Vitamin A, carotene, Vitamin C, and Vitamin E, and the like, and mixtures thereof. Preferably, the antioxidant is selected from the group of lipid-soluble antioxidants consisting of Vitamin A, $\beta$-carotene, Vitamin E, Vitamin E acetate, and mixtures thereof. More preferably, the antioxidant is Vitamin E or Vitamin E acetate. Most preferably, the antioxidant is Vitamin E acetate.

The amount of antioxidant present in the therapeutic wound healing compositions of the present invention is a therapeutically effective amount. A therapeutically effective amount of antioxidant is that amount of antioxidant necessary for the inventive composition to prevent and reduce injury to mammalian cells or increase the resuscitation rate of injured mammalian cells. The exact amount of antioxidant is a matter of preference subject to such factors as the type of condition being treated as well as the other ingredients in the composition. In a preferred embodiment, the antioxidant is present in the therapeutic wound healing composition in an amount from about 0.1% to about 40%, preferably from about 0.2% to about 30%, and more preferably from about 0.5% to about 20%, by weight of the therapeutic wound healing composition.

The mixture of saturated and unsaturated fatty acids in the present invention are those fatty acids required for the repair of mammalian cellular membranes and the production of new cells. Fatty acids are carboxylic acid compounds found in animal and vegetable fat and oil. Fatty acids are classified as lipids and are composed of chains of alkyl groups containing from 4 to 22 carbon atoms and 0–3 double bonds and characterized by a terminal carboxyl group, —COOH. Fatty acids may be saturated or unsaturated and may be solid, semisolid, or liquid. The most common saturated fatty acids are butyric acid ($C_4$), lauric acid ($C_{12}$), palmitic acid ($C_{16}$), and stearic acid ($C_{18}$). Unsaturated fatty acids are usually derived from vegetables and consist of alkyl chains containing from 16 to 22 carbon atoms and 0–3 double bonds with the characteristic terminal carboxyl group. The most common unsaturated fatty acids are oleic acid, linoleic acid, and linolenic acid (all $C_{18}$ acids).

In general, the mixture of saturated and unsaturated fatty acids required for the repair of mammalian cellular membranes in the present invention may be derived from animal and vegetable fats and waxes, prodrugs of saturated and unsaturated fatty acids useful in the present invention, and mixtures thereof. For example, the fatty acids in the therapeutic wound healing composition may be in the form of mono-, di-, or triglycerides, or free fatty acids, or mixtures thereof, which are readily available for the repair of injured cells. Cells produce the chemical components and the energy required for cellular viability and store excess energy in the form of fat. Fat is adipose tissue stored between organs of the body to furnish a reserve supply of energy. The preferred animal fats and waxes have a fatty acid composition similar to that of human fat and the fat contained in human breast milk. The preferred animal fats and waxes may be selected from the group consisting of human fat, chicken fat, cow fat (defined herein as a bovine domestic animal regardless of sex or age), sheep fat, horse fat, pig fat, and whale fat. The more preferred animal fats and waxes may be selected from the group consisting of human fat and chicken fat. The most preferred animal fat is human fat. Mixtures of other fats and waxes, such as vegetable waxes (especially sunflower oil), marine oils (especially shark liver oil), and synthetic waxes and oils, which have a fatty acid composition similar to that of animal fats and waxes, and preferably to that of human fats and waxes, may also be employed.

In a preferred embodiment, the mixture of saturated and unsaturated fatty acids has a composition similar to that of human fat and comprises the following fatty acids: butric acid, caproic acid, caprylic acid, capric acid, lauric acid, myristic acid, myristoleic acid, palmitic acid, palmitoleic acid, stearic, oleic acid, linoleic acid, linolenic acid, arachidic acid, and gaddoleic acid. Preferably, butyric acid, caproic acid, caprylic acid, capric acid, lauric acid, myristic acid, myristoleic acid, palmitic acid, palmitoleic acid, stearic, oleic acid, linoleic acid, linolenic acid, arachidic acid, and gaddoleic acid are present in the mixture in about the following percentages by weight, respectively (carbon chain number and number of unsaturations are shown parenthetically, respectively): 0.2%–0.4% ($C_4$), 0.1% ($C_6$), 0.3%–0.8% ($C_8$), 2.2%–3.5% ($C_{10}$), 0.9%–5.5% ($C_{12}$), 2.8%–8.5% ($C_{14}$), 0.1%–0.6% ($C_{14:1}$), 23.2%–24.6% ($C_{16}$), 1.8%–3.0% ($C_{16:1}$), 6.9%–9.9% ($C_{18}$), 36.0%–36.5% ($C_{18:1}$), 20%–20.6% ($C_{18:2}$), 7.5–7.8% ($C_{18:3}$), 1.1%–4.9% ($C_{20}$), and 3.3%–6.4% ($C_{20:1}$).

In another preferred embodiment, the mixture of saturated and unsaturated fatty acids is typically chicken fat comprising the following fatty acids: lauric acid, myristic acid, myristoleic acid, pentadecanoic acid, palmitic acid, palmitoleic acid, margaric acid, margaroleic acid, stearic, oleic acid, linoleic acid, linolenic acid, arachidic acid, and gaddoleic acid. Preferably, lauric acid, myristic acid, myristoleic acid, pentadecanoic acid, palmitic acid, palmitoleic acid, margaric acid, margaroleic acid, stearic, oleic acid, linoleic acid, linolenic acid, arachidic acid, and gaddoleic acid are present in the mixture in about the following percentages by weight, respectively: 0.1% ($C_{12}$), 0.8% ($C_{14}$), 0.2% ($C_{14:1}$), 0.1% ($C_{15}$), 25.3% ($C_{16}$), 7.2% ($C_{16:1}$), 0.1% ($C_{17}$), 0.1% ($C_{17:1}$), 6.5% ($C_{18}$), 37.7% ($C_{18:1}$), 20.6% ($C_{18:2}$), 0.8% ($C_{18:3}$), 0.2% ($C_{20}$), and 0.3% ($C_{20:1}$), all percentages +/−10%.

In another preferred embodiment, the mixture of saturated and unsaturated fatty acids comprises lecithin. Lecithin (phosphatidylcholine) is a phosphatide found in all living organisms (plants and animals) and is a significant constituent of nervous tissue and brain substance. Lecithin is a mixture of the diglycerides of stearic, palmitic, and oleic acids, linked to the choline ester of phosphoric acid. The product of commerce is predominantly soybean lecithin obtained as a by-product in the manufacturing of soybean oil. Soybean lecithin contains palmitic acid 11.7%, stearic 4.0%, palmitoleic 8.6%, oleic 9.8%, linoleic 55.0%, linolenic 4.0%, $C_{20}$ to $C_{22}$ acids (includes arachidonic) 5.5%. Lecithin may be represented by the formula:

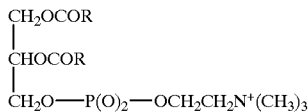

wherein R is selected from the group consisting of stearic, palmitic, and oleic acid.

The above fatty acids and percentages thereof present in the fatty acid mixture are given as an example. The exact type of fatty acid present in the fatty acid mixture and the exact amount of fatty acid employed in the fatty acid mixture may be varied in order to obtain the result desired in the final product and such variations are now within the capabilities of those skilled in the art without the need for undue experimentation.

The amount of fatty acids present in the therapeutic wound healing compositions of the present invention is a therapeutically effective amount. A therapeutically effective amount of fatty acids is that amount of fatty acids necessary for the inventive composition to prevent and reduce injury to mammalian cells or increase the resuscitation rate of injured mammalian cells. The exact amount of fatty acids employed is subject to such factors as the type and distribution of fatty acids employed in the mixture, the type of condition being treated, and the other ingredients in the composition. In a preferred embodiment, the fatty acids are present in the therapeutic wound healing composition in an amount from about 10% to about 50%, preferably from about 20% to about 45%, and more preferably from about 25% to about 40%, by weight of the therapeutic wound healing composition.

In accord with the present invention, the therapeutic wound healing compositions of Embodiment One (I) for treating mammalian cells may be selected from the group consisting of:

(I.A)

(1)
(a) pyruvate selected from the group consisting of pyruvic acid, pharmaceutically acceptable salts of pyruvic acid, and mixtures thereof;
(b) an antioxidant; and
(c) a mixture of saturated and unsaturated fatty acids wherein the fatty acids are those fatty acids required for the repair of cellular membranes and resuscitation of mammalian cells;

(I.B)

(2)
(a) pyruvate selected from the group consisting of pyruvic acid, pharmaceutically acceptable salts of pyruvic acid, and mixtures thereof;
(b) lactate selected from the group consisting of lactic acid, pharmaceutically acceptable salts of lactic acid, and mixtures thereof; and
(c) a mixture of saturated and unsaturated fatty acids wherein the fatty acids are those fatty acids required for the repair of cellular membranes and resuscitation of mammalian cells;

(I.C)

(3)
(a) an antioxidant; and
(b) a mixture of saturated and unsaturated fatty acids wherein the fatty acids are those fatty acids required for the repair of cellular membranes and resuscitation of mammalian cells;

(ID)

(4)
(a) lactate selected from the group consisting of lactic acid, pharmaceutically acceptable salts of lactic acid, and mixtures thereof;
(b) an antioxidant; and
(c) a mixture of saturated and unsaturated fatty acids wherein the fatty acids are those fatty acids required for the repair of cellular membranes and resuscitation of mammalian cells.

Preferably, the wound healing compositions of Embodiment One (I) for treating mammalian cells, preferably epidermal keratinocytes, may be selected from the group consisting of:

(I.A)

(1)
(a) pyruvate selected from the group consisting of pyruvic acid, pharmaceutically acceptable salts of pyruvic acid, and mixtures thereof;
(b) an antioxidant; and
(c) a mixture of saturated and unsaturated fatty acids wherein the fatty acids are those fatty acids required for the repair of cellular membranes and resuscitation of mammalian cells;

(2)
(a) pyruvate selected from the group consisting of pyruvic acid, pharmaceutically acceptable salts of pyruvic acid, and mixtures thereof;

(b) lactate selected from the group consisting of lactic acid, pharmaceutically acceptable salts of lactic acid, and mixtures thereof; and (c) a mixture of saturated and unsaturated fatty acids wherein the fatty acids are those fatty acids required for the repair of cellular membranes and resuscitation of mammalian cells; and (I.C)

(3)

(a) an antioxidant; and (b) a mixture of saturated and unsaturated fatty acids wherein the fatty acids are those fatty acids required for the repair of cellular membranes and resuscitation of mammalian cells.

More preferably, the wound healing compositions of Embodiment One (I) for treating mammalian cells, preferably epidermal keratinocytes, may be selected from the group consisting of:

(I.A)

(1)

(a) pyruvate selected from the group consisting of pyruvic acid, pharmaceutically acceptable salts of pyruvic acid, and mixtures thereof;

(b) an antioxidant; and (c) a mixture of saturated and unsaturated fatty acids wherein the fatty acids are those fatty acids required for the repair of cellular membranes and resuscitation of mammalian cells; and (I.C)

(3)

(a) an antioxidant; and (b) a mixture of saturated and unsaturated fatty acids wherein the fatty acids are those fatty acids required for the repair of cellular membranes and resuscitation of mammalian cells.

More preferably, the wound healing compositions of Embodiment One (I) for treating mammalian cells, preferably epidermal keratinocytes, may be selected from the group consisting of:

(I.A)

(1)

(a) pyruvate selected from the group consisting of pyruvic acid, pharmaceutically acceptable salts of pyruvic acid, and mixtures thereof;

(b) an antioxidant; and (c) a mixture of saturated and unsaturated fatty acids wherein the fatty acids are those fatty acids required for the repair of cellular membranes and resuscitation of mammalian cells; and (I.B)

(2)

(a) pyruvate selected from the group consisting of pyruvic acid, pharmaceutically acceptable salts of pyruvic acid, and mixtures thereof;

(b) lactate selected from the group consisting of lactic acid, pharmaceutically acceptable salts of lactic acid, and mixtures thereof; and (c) a mixture of saturated and unsaturated fatty acids wherein the fatty acids are those fatty acids required for the repair of cellular membranes and resuscitation of mammalian cells.

Most preferably, the wound healing compositions of Embodiment One (I) for treating mammalian cells, preferably epidermal keratinocytes, comprise:

(I.A)

(a) pyruvate selected from the group consisting of pyruvic acid, pharmaceutically acceptable salts of pyruvic acid, and mixtures thereof;

(b) an antioxidant; and (c) a mixture of saturated and unsaturated fatty acids wherein the fatty acids are those fatty acids required for the repair of cellular membranes and resuscitation of mammalian cells.

Most preferably, the wound healing compositions of Embodiment One (I) for treating mammalian cells, preferably monocytes, comprise:

(I.D)

(a) lactate selected from the group consisting of lactic acid, pharmaceutically acceptable salts of lactic acid, and mixtures thereof;

(b) an antioxidant; and (c) a mixture of saturated and unsaturated fatty acids wherein the fatty acids are those fatty acids required for the repair of cellular membranes and resuscitation of mammalian cells.

Throughout this disclosure, applicant will suggest various theories or mechanisms by which applicant believes the components in the therapeutic wound healing compositions and the TGF-beta function together in an unexpected synergistic manner to prevent and reduce injury to mammalian cells, increase the resuscitation rate of injured mammalian cells, and reduce viral titers. While applicant may offer various mechanisms to explain the present invention, applicant does not wish to be bound by theory. These theories are suggested to better understand the present invention but are not intended to limit the effective scope of the claims.

In the first aspect of Embodiment One (I.A), applicant believes that pyruvate can be transported inside a cell where it can act as an antioxidant to neutralize oxygen radicals in the cell. Pyruvate can also be used inside the cell in the citric acid cycle to provide energy to increase cellular viability, and as a precursor in the synthesis of important biomolecules to promote cellular proliferation. In addition, pyruvate can be used in the multifunction oxidase system to reverse cytotoxicity. Antioxidants, especially lipid-soluble antioxidants, can be absorbed into the cell membrane to neutralize oxygen radicals and thereby protect the membrane. The saturated and unsaturated fatty acids in the present invention are those fatty acids required for the resuscitation of mammalian cells and are readily available for the repair of injured cells and the proliferation of new cells. Cells injured by oxygen radicals need to produce unsaturated fatty acids to repair cellular membranes. However, the production of unsaturated fatty acids by cells requires oxygen. Thus, the injured cell needs high levels of oxygen to produce unsaturated fatty acids and at the same time needs to reduce the level of oxygen within the cell to reduce oxidative injury. By providing the cell with the unsaturated fatty acids needed for repair, the need of the cell for unsaturated fatty acids is reduced and the need for high oxygen levels is also reduced.

The combination of pyruvate inside the cell and an antioxidant in the cellular membrane functions in an unexpected synergistic manner to reduce hydrogen peroxide production in the cell to levels lower than can be achieved by use of either type of component alone. The presence of mixtures of saturated and unsaturated fatty acids in the therapeutic wound healing composition significantly enhances the ability of pyruvate and the antioxidant to inhibit reactive oxygen production. By stabilizing the cellular membrane, unsaturated fatty acids also improve membrane function and enhance pyruvate transport into the cell. Hence, the three components in the therapeutic wound healing composition of the first aspect of Embodiment One (I. A) function together in an unexpected synergistic manner to prevent and reduce injury to mammalian cells and increase the resuscitation rate of injured mammalian cells.

In the second aspect of Embodiment One (I.B), lactate is employed instead of an antioxidant. Antioxidants react with, and neutralize, oxygen radicals after the radicals are already formed. Lactate, on the other hand, is a component in the cellular feedback mechanism and inhibits the respiratory bursting process to suppress the production of active oxygen species. The combination of pyruvate to neutralize active oxygen species and lactate to suppress the respiratory bursting process functions in a synergistic manner to reduce hydrogen peroxide production in the cell to levels lower than can be achieved by use of either type of component alone. The presence of mixtures of saturated and unsaturated fatty acids in the therapeutic wound healing composition significantly enhances the ability of pyruvate and lactate to inhibit reactive oxygen production. Hence, the three components in the therapeutic wound healing composition in the second aspect of Embodiment One (I.B) function together in a synergistic manner to protect and resuscitate mammalian cells.

In the third aspect of Embodiment One (I.C), the presence of mixtures of saturated and unsaturated fatty acids in the therapeutic wound healing composition in this embodiment significantly enhances the ability of the antioxidant to inhibit reactive oxygen production. The combination of an antioxidant to neutralize active oxygen species and fatty acids to rebuild cellular membranes and reduce the need of the cell for oxygen functions in a synergistic manner to reduce hydrogen peroxide production in the cell to levels lower than can be achieved by either type of component alone. Hence, the components in the therapeutic wound healing composition in the third aspect of Embodiment One (I.C) function together in a synergistic manner to protect and resuscitate mammalian cells.

In the fourth aspect of Embodiment One (I.D), lactate is employed because the respiratory bursting process is more pronounced in monocytes than in epidermal keratinocytes. The combination of lactate to suppress the respiratory bursting process and an antioxidant to neutralize active oxygen species functions in a synergistic manner to reduce hydrogen peroxide production in the cell to levels lower than can be achieved by either component alone. The presence of mixtures of saturated and unsaturated fatty acids in the therapeutic wound healing composition in this embodiment significantly enhances the ability of lactate and the antioxidant to inhibit reactive oxygen production. Hence, the three components in the therapeutic wound healing composition in the fourth aspect of Embodiment One (I.D) function together in an unexpected synergistic manner to protect and resuscitate mammalian cells.

Accordingly, the combination of ingredients set out in the above embodiments functions together in an enhanced manner to prevent and reduce injury to mammalian cells and increase the resuscitation rate of injured mammalian cells. The therapeutic effect of the combination of the components in each of the above embodiments is markedly greater than that expected by the mere addition of the individual therapeutic components. Hence, applicant's therapeutic wound healing compositions for treating mammalian cells have the ability to decrease intracellular levels of hydrogen peroxide production, increase cellular resistance to cytotoxic agents, increase rates of cellular proliferation, and increase cellular viability.

B. Methods For Making The Wound Healing Compositions Of Embodiment One (I.A–D)

The present invention extends to methods for making the therapeutic wound healing compositions of Embodiment One (I.A–D). In general, a therapeutic wound healing composition is made by forming an admixture of the components of the composition. In a first aspect of Embodiment One (I.A), a therapeutic wound healing composition is made by forming an admixture of (a) pyruvate selected from the group consisting of pyruvic acid, pharmaceutically acceptable salts of pyruvic acid, and mixtures thereof, (b) an antioxidant, and (c) a mixture of saturated and unsaturated fatty acids wherein the fatty acids are those fatty acids required for the repair of cellular membranes and resuscitation of mammalian cells. In a second aspect of Embodiment One (I.B), a therapeutic wound healing composition is made by forming an admixture of (a) pyruvate selected from the group consisting of pyruvic acid, pharmaceutically acceptable salts of pyruvic acid, and mixtures thereof, (b) lactate selected from the group consisting of lactic acid, pharmaceutically acceptable salts of lactic acid, and mixtures thereof and (c) a mixture of saturated and unsaturated fatty acids wherein the fatty acids are those fatty acids required for the repair of cellular membranes and resuscitation of mammalian cells. In a third aspect of Embodiment One (I.C), a therapeutic wound healing composition is made by forming an admixture of (a) an antioxidant and (b) a mixture of saturated and unsaturated fatty acids wherein the fatty acids are those fatty acids required for the repair of cellular membranes and resuscitation of mammalian cells. In a fourth aspect of Embodiment One (I.D), a therapeutic wound healing composition is made by forming an admixture of (a) lactate selected from the group consisting of lactic acid, pharmaceutically acceptable salts of lactic acid, and mixtures thereof, (b) an antioxidant, and (c) a mixture of saturated and unsaturated fatty acids wherein the fatty acids are those fatty acids required for the repair of cellular membranes and resuscitation of mammalian cells.

For some applications, the admixture may be formed in a solvent such as water, and a surfactant may be added if required. If necessary, the pH of the solvent is adjusted to a range from about 3.5 to about 8.0, and preferably from about 4.5 to about 7.5, and more preferably about 6.0 to about 7.4. The admixture is then sterile filtered. Other ingredients may also be incorporated into the therapeutic wound healing composition as dictated by the nature of the desired composition as well known by those having ordinary skill in the art. The ultimate therapeutic wound healing compositions are readily prepared using methods generally known in the pharmaceutical arts.

In a preferred embodiment, the invention is directed to a method for preparing a therapeutic wound healing composition (I.A) for preventing and reducing injury to mammalian cells, and increasing the resuscitation rate of injured mammalian cells, which comprises the steps of admixing the following ingredients:

(a) pyruvate selected from the group consisting of pyruvic acid, pharmaceutically acceptable salts of pyruvic acid, and mixtures thereof;

(b) an antioxidant; and (c) a mixture of saturated and unsaturated fatty acids wherein the fatty acids are those fatty acids required for the resuscitation of injured mammalian cells.

C. Methods For Employing The Wound Healing Compositions Of Embodiment One (I.A–D)

The present invention extends to methods for employing the therapeutic wound healing compositions of Embodiment One (I) in vivo and in vitro. In general, a therapeutic wound healing composition is employed by contacting the therapeutic composition with mammalian cells.

In a first aspect of Embodiment One (I.A), the invention is directed to a method for preventing and reducing injury to mammalian cells, and increasing the resuscitation rate of injured mammalian cells, which comprises the steps of (A) providing a therapeutic wound healing composition which comprises (a) pyruvate selected from the group consisting of pyruvic acid, pharmaceutically acceptable salts of pyruvic acid, and mixtures thereof, (b) an antioxidant, and (c) a mixture of saturated and unsaturated fatty acids wherein the fatty acids are those fatty acids required for the resuscitation of injured mammalian cells, and (B) contacting the therapeutic wound healing composition with the mammalian cells.

In a second aspect of Embodiment One (I.B), the invention is directed to a method for preventing and reducing injury to mammalian cells, and increasing the resuscitation rate of injured mammalian cells, which comprises the steps of (A) providing a therapeutic wound healing composition which comprises (a) pyruvate selected from the group consisting of pyruvic acid, pharmaceutically acceptable salts of pyruvic acid, and mixtures thereof, (b) lactate selected from the group consisting of lactic acid, pharmaceutically acceptable salts of lactic acid, and mixtures thereof, and (c) a mixture of saturated and unsaturated fatty acids wherein the fatty acids are those fatty acids required for the resuscitation of injured mammalian cells, and (B) contacting the therapeutic wound healing composition with the mammalian cells.

In a third aspect of Embodiment One (I.C), the invention is directed to a method for preventing and reducing injury to mammalian cells, and increasing the resuscitation rate of injured mammalian cells, which comprises the steps of (A) providing a therapeutic wound healing composition which comprises (a) an antioxidant, and (b) a mixture of saturated and unsaturated fatty acids wherein the fatty acids are those fatty acids required for the resuscitation of injured mammalian cells, and (B) contacting the therapeutic wound healing composition with the mammalian cells.

In a fourth aspect of Embodiment One (I.D), the invention is directed to a method for preventing and reducing injury to mammalian cells, and increasing the resuscitation rate of injured mammalian cells, which comprises the steps of (A) providing a therapeutic wound healing composition which comprises (a) lactate selected from the group consisting of lactic acid, pharmaceutically acceptable salts of lactic acid, and mixtures thereof, (b) an antioxidant, and (c) a mixture of saturated and unsaturated fatty acids wherein the fatty acids are those fatty acids required for the resuscitation of injured mammalian cells, and (B) contacting the therapeutic wound healing composition with the mammalian cells.

In a preferred embodiment, the invention is directed to a method for healing a wound in a mammal which comprises the steps of (A) providing a therapeutic wound healing composition (I.A) which comprises:
   (a) pyruvate selected from the group consisting of pyruvic acid, pharmaceutically acceptable salts of pyruvic acid, and mixtures thereof;
   (b) an antioxidant; and
   (c) a mixture of saturated and unsaturated fatty acids wherein the fatty acids are those fatty acids required for the resuscitation of injured mammalian cells; and (B) contacting the therapeutic wound healing composition with the wound.

The types of wounds which may be healed using the wound healing compositions of Embodiment One (I.A–D) of the present invention are those which result from an injury which causes epidermal damage such as incisions, wounds in which the skin is broken by a cutting instrument, and lacerations, wounds in which the skin is broken by a dull or blunt instrument. The therapeutic compositions may also be used to treat various dermatological disorders such as hyperkeratosis, photo-aging, burns, donor site wounds from skin transplants, ulcers (cutaneous, decubitis, venous stasis, and diabetic), psoriasis, skin rashes, and sunburn photoreactive processes. The topical therapeutic compositions may also be used orally in the form of a mouth wash or spray to protect and accelerate the healing of injured oral tissue such as mouth sores and burns. The topical therapeutic compositions may further be used in ophthalmological preparations to treat wounds such as those which result from corneal ulcers, radialkeratotomy, corneal transplants, epikeratophakia and other surgically induced wounds in the eye. The topical therapeutic compositions may in addition be used in anorectal creams and suppositories to treat such conditions as pruritus ani, proctitis, anal fissures, and hemorrhoids. In a preferred embodiment, the therapeutic compositions are used to treat wounds such as incisions and lacerations.

The wound healing compositions of Embodiment One (I.A–D) of the present invention may be utilized in topical products, ingestible products, and tissue culture medium to protect mammalian ceUs and increase the resuscitation rate of injured mammalian cells. For example, the therapeutic wound healing compositions may be used in topical skin care products to protect and increase the resuscitation rate of skin tissue such as in the treatment of various dermatological disorders such as hyperkeratosis, photo-aging, and sunburn photoreactive processes. Injury to skin can occur for a variety of reasons. Injury often occurs to individuals who wash their hands often, to individuals who are exposed to stressful environmental conditions (overexposure to sun or chemicals), or to the elderly or individuals with an underlining disease. The addition of the wound healing compositions of the present invention to a lotion provides a source of antioxidants to the skin which would protect the skin from the harmful effects of UV light, chemicals, and severe drying. The wound healing compositions can be used for the following indications: a) Moisturizing and protecting; b) Healing dry cracked skin; c) Treating irritated skin such as diaper rash; d) Healing severe dry skin due to other diseases (venous dermatitis); e) Treating psoriasis and other hyperproliferative diseases; f) Protecting skin from UV light damage (antioxidant skin replacement); g) Treating seborrheic conditions; and h) Treating shaving wounds in an after shave lotion.

The topical therapeutic wound healing compositions may also be used orally in the form of a mouth wash or spray to protect and accelerate the healing of injured oral tissue such as mouth sores and burns. The topical therapeutic wound healing compositions may further be used in ophthalmological preparations such as eye care products to neutralize hydrogen peroxide used in the cleaning of contact lenses. The topical therapeutic wound healing compositions may in addition be used in anorectal creams and suppositories to treat such conditions as pruritus ani, proctitis, anal fissures, and hemorrhoids. Initially as white blood cells enter a wound site, the cells release oxygen radicals, depleting the antioxidants at the wound site, thus impairing the healing process. Incorporating the wound healing compositions of the present invention into a wound healing formulation would facilitate healing by providing the site with usable antioxidants, and a source of fatty acids needed for membrane repair. The wound healing compositions can be used for the following indications: a) Healing of cuts and scrapes; b) Burns (heals burns with less scaring and scabbing); c) Decubitus ulcers; d) Bed sores, pressure ulcers; e) Fissures, Hemorrhoids; f) Use in combination with immunostimulators (simulated healing in healing deficient people); g) Post surgical wounds; h) Bandages; i) Diabetic ulcers; j) Venous ulceration; and k) Use in combination with wound cleansing agents.

The therapeutic wound healing compositions may also be used in ingestible products to protect and increase the resuscitation rate of erosions, stomach ulcers, and hemorrhages in the gastric mucosa. Other ingestible therapeutic products include: stroke medications; autoimmune disease medications; arthritis medications; ulcer medications; cancer medications (cytotoxic agents); heart medication to improve regional ventricular function and restore normal heart rate and pressure functions; lung medication to repair injured tissue; liver medication to suppress lipogenesis of alcoholic origin and prevent hepatic steatosis; kidney medication to suppress urinary calculi (kidney stones); detoxification medication to antagonize heavy metal poisoning, cyanide poisoning, sodium sulfide poisoning, other types of poisoning; and reduce and neutralize the production of oxygen radicals which produces injury to tissue, to protect and further enhance the resuscitation rate of the injured mammalian cells. The therapeutic wound healing compositions may be used in ingestible products to treat inflammatory diseases such as hepatitis, gastritis, colitis, esophagitis, arthritis, and pancreatitis.

The therapeutic wound healing compositions of the present invention may also be used in tissue culture media and organ transplant media to prevent and reduce injury to mammalian cells and increase the resuscitation rate of injured mammalian cells. Tissue cultures and transplant organs encounter reactive oxygen species generated in the culture media by the injured cells. Organs particularly susceptible to oxidative damage during transport and transplantation due to reperfusion injury following ischemia are corneas, livers, hearts, and kidneys. The therapeutic wound healing compositions may be useful to abrogate reperfusion injury to such transplant organs.

In a specific embodiment, the invention is directed to a method for preserving mammalian cells in a culture medium which comprises the steps of:
(A) providing a therapeutic wound healing composition selected from the group of consisting of:

(I.A)

(1)
(a) pyruvate selected from the group consisting of pyruvic acid, pharmaceutically acceptable salts of pyruvic acid, and mixtures thereof;

(b) an antioxidant; and
(c) a mixture of saturated and unsaturated fatty acids wherein the fatty acids are those fatty acids required for the repair of cellular membranes and resuscitation of mammalian cells;

(I.B)

(2)
(a) pyruvate selected from the group consisting of pyruvic acid, pharmaceutically acceptable salts of pyruvic acid, and mixtures thereof;
(b) lactate selected from the group consisting of lactic acid, pharmaceutically acceptable salts of lactic acid, and mixtures thereof; and
(c) a mixture of saturated and unsaturated fatty acids wherein the fatty acids are those fatty acids required for the repair of cellular membranes and resuscitation of mammalian cells;

(I.C)

(3)
(a) an antioxidant; and
(b) a mixture of saturated and unsaturated fatty acids wherein the fatty acids are those fatty acids required for the repair of cellular membranes and resuscitation of mammalian cells;

(I.D)

(4)
(a) lactate selected from the group consisting of lactic acid, pharmaceutically acceptable salts of lactic acid, and mixtures thereof;
(b) an antioxidant; and
(c) a mixture of saturated and unsaturated fatty acids wherein the fatty acids are those fatty acids required for the repair of cellular membranes and resuscitation of mammalian cells;
(B) providing mammalian cells in a culture medium; and
(C) contacting the therapeutic wound healing composition from step (A) with the mammalian cells in the culture medium from step (B).

D. Formulations Of The Wound Healing Compositions Of Embodiment One (I.A–D)

Once prepared, the inventive therapeutic wound healing compositions of Embodiment One (I.A–D) may be stored for future use or may be formulated in effective amounts with pharmaceutically acceptable carriers to prepare a wide variety of pharmaceutical compositions. Examples of pharmaceutically acceptable carriers are pharmaceutical appliances, topical vehicles (non-oral and oral), and ingestible vehicles.

Examples of pharmaceutical appliances are sutures, staples, gauze, bandages, burn dressings, artificial skins, liposome or micell formulations, microcapsules, aqueous vehicles for soaking gauze dressings, and the like, and mixtures thereof. Non-oral topical compositions employ non-oral topical vehicles, such as creams, gels formulations, foams, ointments and sprays, salves, and films, which are intended to be applied to the skin or body cavity and are not intended to be taken by mouth. Oral topical compositions employ oral vehicles, such as mouthwashes, rinses, oral sprays, suspensions, and dental gels, which are intended to be taken by mouth but are not intended to be ingested. Ingestible compositions employ ingestible or partly ingestible vehicles such as confectionery bulking agents which include hard and soft confectionery such as lozenges, tablets, toffees, nougats, suspensions, chewy candies, and chewing gums.

In one form of the invention, the therapeutic wound healing composition is incorporated into a pharmaceutical appliance which may be in the form of sutures, staples, gauze, bandages, burn dressings, artificial skins, liposome or micell formulations, microcapsules, aqueous vehicles for soaking gauze dressings, and the like, and mixtures thereof A variety of traditional ingredients may optionally be included in the pharmaceutical composition in effective amounts such as buffers, preservatives, tonicity adjusting agents, antioxidants, polymers for adjusting viscosity or for use as extenders, and excipients, and the like. Specific illustrative examples of such traditional ingredients include acetate and borate buffers; thimerosol, sorbic acid, methyl and propyl paraben and chlorobutanol preservatives; sodium chloride and sugars to adjust the tonicity; and excipients such as mannitol, lactose and sucrose. Other conventional pharmaceutical additives known to those having ordinary skill in the pharmaceutical arts may also be used in the pharmaceutical composition.

In accordance with this invention, therapeutically effective amounts of the therapeutic wound healing compositions of the present invention may be employed in the pharmaceutical appliance. These amounts are readily determined by those skilled in the art without the need for undue experimentation. The exact amount of the therapeutic wound healing composition employed is subject to such factors as the type and concentration of the therapeutic wound healing composition and the type of pharmaceutical appliance employed. Thus, the amount of therapeutic wound healing composition may be varied in order to obtain the result desired in the final product and such variations are within the capabilities of those skilled in the art without the need for undue experimentation. In a preferred embodiment, the pharmaceutical composition will comprise the therapeutic wound healing composition in an amount from about 0.1% to about 5%, by weight of the pharmaceutical composition. In a more preferred embodiment, the pharmaceutical composition will comprise the therapeutic wound healing composition in an amount from about 0.1% to about 3%, by weight of the pharmaceutical composition. In a most preferred embodiment, the pharmaceutical composition will comprise the therapeutic wound healing composition in an amount from about 0.1% to about 1%, by weight of the pharmaceutical composition.

The present invention extends to methods for making the pharmaceutical compositions. In general, a pharmaceutical composition is made by contacting a therapeutically effective amount of a therapeutic wound healing composition with a pharmaceutical appliance and the other ingredients of the final desired pharmaceutical composition. The therapeutic wound healing composition may be in a solvent and may be absorbed onto a pharmaceutical appliance.

Other ingredients will usually be incorporated into the composition as dictated by the nature of the desired composition as well known by those having ordinary skill in the art. The ultimate pharmaceutical compositions are readily prepared using methods generally known in the pharmaceutical arts.

In another form of the invention, the therapeutic wound healing composition is incorporated into a non-oral topical vehicle which may be in the form of a cream, gel, foam, ointment, spray, and the like. Typical non-toxic non-oral topical vehicles known in the pharmaceutical arts may be used in the present invention. The preferred non-oral topical vehicles are water and pharmaceutically acceptable water-miscible organic solvents such as ethyl alcohol, isopropyl alcohol propylene glycol glycerin, and the like, and mixtures of these solvents. Water-alcohol mixtures are particularly preferred and are generally employed in a weight ratio from about 1:1 to about 20:1, preferably from about 3:1 to about 20:1, and most preferably from about 3:1 to about 10:1, respectively.

The non-oral topical therapeutic wound healing compositions may also contain conventional additives employed in those products. Conventional additives include humectants, emollients, lubricants, stabilizers, dyes, and perfumes, providing the additives do not interfere with the therapeutic properties of the therapeutic wound healing composition.

Suitable humectants useful in the non-oral topical therapeutic wound healing compositions include glycerin, propylene glycol, polyethylene glycol, sorbitan, fructose, and the like, and mixtures thereof. Humectants, when employed, may be present in amounts from about 10% to about 20%, by weight of the topical therapeutic wound healing composition.

The coloring agents (colors, colorants) useful in the non-oral topical therapeutic wound healing composition are used in amounts effective to produce the desired color. These coloring agents include pigments which may be incorporated in amounts up to about 6% by weight of the non-oral topical therapeutic wound healing composition. A preferred pigment, titanium dioxide, may be incorporated in amounts up to about 2%, and preferably less than about 1%, by weight of the non-oral topical therapeutic wound healing composition. The coloring agents may also include natural food colors and dyes suitable for food, drug and cosmetic applications. These coloring agents are known as F.D.& C. dyes and lakes. The materials acceptable for the foregoing uses are preferably water-soluble. Illustrative nonlimiting examples include the indigoid dye known as F.D.& C. Blue No.2, which is the disodium salt of 5,5-indigotindisulfonic acid. Similarly, the dye known as F.D.& C. Green No.1 comprises a triphenylmethane dye and is the monosodium salt of 4-[4-(N-ethyl-p-sulfoniumbenzylamino) diphenylmethylene]-[1-(N-ethyl-N-p-sulfoniumbenzyl)-$\delta$2, 5-cyclohexadieneimine]. A full recitation of all F.D.& C. coloring agents and their corresponding chemical structures may be found in the Kirk-Othmer Encyclopedia of Chemical Technology, 3rd Edition, in volume 5 at pages 857–884, which text is incorporated herein by reference.

In accordance with this invention, therapeutically effective amounts of the therapeutic wound healing compositions of the present invention may be admixed with a non-oral topical vehicle to form a topical therapeutic wound healing composition. These amounts are readily determined by those skilled in the art without the need for undue experimentation. In a preferred embodiment, the non-oral topical therapeutic wound healing compositions will comprise the therapeutic wound healing composition in an amount from about 0.1% to about 10% and a non-oral topical vehicle in a quantity sufficient to bring the total amount of composition to 100%, by weight of the non-oral topical therapeutic wound healing composition. In a more preferred embodiment, the non-oral topical therapeutic wound healing compositions will comprise the therapeutic wound healing composition in an amount from about 0.1% to about 5%, and in a most preferred embodiment, the non-oral topical therapeutic wound healing compositions will comprise the therapeutic wound healing composition in an amount from about 0.1% to about 2%, and a non-oral topical vehicle in a quantity sufficient to bring the total amount of composition to 100%, by weight of the non-oral topical therapeutic wound healing composition.

The present invention extends to methods for preparing the non-oral topical therapeutic wound healing compositions. In such a method, the non-oral topical therapeutic wound healing composition is prepared by admixing a therapeutically effective amount of the therapeutic wound healing composition of the present invention and a non-oral topical vehicle. The final compositions are readily prepared using standard methods and apparatus generally known by those skilled in the pharmaceutical arts. The apparatus useful in accordance with the present invention comprises mixing apparatus well known in the pharmaceutical arts, and therefore the selection of the specific apparatus will be apparent to the artisan.

In another form of the invention, the therapeutic wound healing composition is incorporated into an oral topical vehicle which may be in the form of a mouthwash, rinse, oral spray, suspension, dental gel, and the like. Typical non-toxic oral vehicles known in the pharmaceutical arts may be used in the present invention. The preferred oral vehicles are water, ethanol, and water-ethanol mixtures. The water-ethanol mixtures are generally employed in a weight ratio from about 1:1 to about 20:1, preferably from about 3:1 to about 20:1, and most preferably from about 3:1 to about 10:1, respectively. The pH value of the oral vehicle is generally from about 4 to about 7, and preferably from about 5 to about 6.5. An oral topical vehicle having a pH value below about 4 is generally irritating to the oral cavity and an oral vehicle having a pH value greater than about 7 generally results in an unpleasant mouth feel.

The oral topical therapeutic wound healing compositions may also contain conventional additives normally employed in those products. Conventional additives include a fluorine providing compound, a sweetening agent, a flavoring agent, a coloring agent, a humectant, a buffer, and an emulsifier, providing the additives do not interfere with the therapeutic properties of the therapeutic wound healing composition.

The coloring agents and humectants, and the amounts of these additives to be employed, set out above as useful in the non-oral topical therapeutic wound healing composition may be used in the oral topical therapeutic wound healing composition.

Fluorine providing compounds may be fully or slightly water soluble and are characterized by their ability to release fluoride ions or fluoride containing ions in water and by their lack of reaction with other components in the composition. Typical fluorine providing compounds are inorganic fluoride salts such as water-soluble alkali metal, alkaline earth metal, and heavy metal salts, for example, sodium fluoride, potassium fluoride, ammonium fluoride, cuprous fluoride, zinc fluoride, stannic fluoride, stannous fluoride, barium fluoride, sodium fluorosilicate, ammonium fluorosilicate, sodium fluorozirconate, sodium monofluorophosphate, aluminum mono- and di-fluorophosphates and fluorinated sodium calcium pyrophosphate. Alkali metal fluorides, tin fluoride and monofluorophosphates, such as sodium and stannous fluoride, sodium monofluorophosphate and mixtures thereof, are preferred.

The amount of fluorine providing compound present in the present oral topical therapeutic wound healing composition is dependent upon the type of fluorine providing compound employed, the solubility of the fluorine compound, and the nature of the final oral therapeutic wound healing composition. The amount of fluorine providing compound used must be a nontoxic amount. In general, the fluorine providing compound when used will be present in an amount up to about 1%, preferably from about 0.001% to about 0.1%, and most preferably from about 0.001% to about 0.05%, by weight of the oral topical therapeutic wound healing composition.

When sweetening agents (sweeteners) are used, those sweeteners well known in the art, including both natural and artificial sweeteners, may be employed. The sweetening agent used may be selected from a wide range of materials including water-soluble sweetening agents, water-soluble artificial sweetening agents, water-soluble sweetening agents derived from naturally occurring water-soluble sweetening agents, dipeptide based sweetening agents, and protein based sweetening agents, including mixtures thereof Without being limited to particular sweetening agents, representative categories and examples include:

(a) water-soluble sweetening agents such as monosaccharides, disaccharides and polysaccharides such as xylose, ribose, glucose (dextrose), mannose, galactose, fructose (levulose), sucrose (sugar), maltose, invert sugar (a mixture of fructose and glucose derived from sucrose), partially hydrolyzed starch, corn syrup solids, dihydrochalcones, monellin, steviosides, and glycyrrhizin, and mixtures thereof;

(b) water-soluble artificial sweeteners such as soluble saccharin salts, i.e., sodium or calcium saccharin salts, cyclamate salts, the sodium, ammonium or calcium salt of 3,4-dihydro-6-methyl-1,2,3-oxathiazine4-one-2,2-dioxide, the potassium salt of 3,4-dihydro-6-methyl-1,2,3-oxathiazine4-one-2,2-dioxide (Acesulfame-K), the free acid form of saccharin, and the like;

(c) dipeptide based sweeteners, such as L-aspartic acid derived sweeteners, such as L-aspartyl-L-phenylalanine methyl ester (Aspartame) and materials described in U.S. Pat. No. 3,492,131, L-α-aspartyl-N-(2,2,4,4-tetramethyl-3-thietanyl)-D-alanin-amide hydrate (Alitame), methyl esters of L-aspartyl-L-phenylglycerine and L-aspartyl-L-2,5-dihydrophenyl-glycine, L-aspartyl-2,5-dihydro-L-phenylalanine; L-aspartyl-L-(1-cyclohexen)-alanine, and the like;

(d) water-soluble sweeteners derived from naturally occurring water-soluble sweeteners, such as chlorinated derivatives of ordinary sugar (sucrose), e.g., chlorodeoxysugar derivatives such as derivatives of chlorodeoxysucrose or chlorodeoxygalactosucrose, known, for example, under the product designation of Sucralose; examples of chlorodeoxysucrose and chlorodeoxygalacto-sucrose derivatives include but are not limited to: 1-chloro-1'-deoxysucrose; 4-chloro4-deoxyα-D-galacto-pyranosyl-α-D-fructofuranoside, or 4-chloro-4-deoxygalactosucrose; 4-chloro4-deoxyα-D-galacto-pyranosyl-1-chloro-1-deoxy-β-D-fructo-furanoside, or 4,1'-dichloro-4,1'-dideoxygalactosucrose; 1',6'-dichloro-1',6'-dideoxysucrose; 4-chloro4-deoxy-α-D-galacto-pyranosyl-1,6-dichloro-1,6-dideoxy-β-D-fructo-furanoside, or 4,1',6'-trichloro-4,1',6'-trideoxygalacto-sucrose; 4,6-dichloro-4,6-dideoxy-α-D-galacto-pyranosyl-6-chloro-6- deoxy-β-D-fructofuranoside, or 4,6,6'-trichloro-4,6,6'-trideoxygalactosucrose; 6,1',6'-trichloro-6,1',6'-trideoxysucrose; 4,6-dichloro4,6-dideoxy-α-D-galacto-pyranosyl-1,6-dichloro-1,6-di-deoxy-β-D-fructofuranoside, or 4,6,1',6'-tetrachloro-4,6,1',6'-tetradeoxygalacto-sucrose; and 4,6,1',6'-tetrachloro-4,6,1', 6'-tetradeoxy-sucrose; and (e) protein based sweeteners such as thaumaoccous danielli (Thaumatin I and II).

In general, an effective amount of sweetening agent is utilized to provide the level of sweetness desired in the particular oral topical therapeutic wound healing composition, and this amount will vary with the sweetener selected and the final oral therapeutic product desired. The amount of sweetener normally present is in the range from about 0.0025% to about 90%, by weight of the oral topical therapeutic wound healing composition, depending upon the sweetener used. The exact range of amounts for each type of sweetener is well known in the art and is not the subject of the present invention.

The flavoring agents (flavors, flavorants) which may be used include those flavors known to the skilled artisan, such as natural and artificial flavors. Suitable flavoring agents include mints, such as peppermint, citrus flavors such as orange and lemon, artificial vanilla, cinnamon, various fruit flavors, both individual and mixed, and the like.

The amount of flavoring agent employed in the oral topical therapeutic wound healing composition is normally a matter of preference subject to such factors as the type of final oral therapeutic wound healing composition, the individual flavor employed, and the strength of flavor desired. Thus, the amount of flavoring may be varied in order to obtain the result desired in the final product and such variations are within the capabilities of those skilled in the art without the need for undue experimentation. The flavoring agents, when used, are generally utilized in amounts that may, for example, range in amounts from about 0.05% to about 6%, by weight of the oral topical therapeutic wound healing composition.

Suitable buffer solutions useful in the non-oral topical therapeutic wound healing compositions include citric acid-sodium citrate solution, phosphoric acid-sodium phosphate solution, and acetic acid-sodium acetate solution in amounts up to about 1%, and preferably from about 0.05% to about 0.5% by weight of the oral topical therapeutic wound healing composition.

In accordance with this invention, therapeutically effective amounts of the therapeutic wound healing compositions of the present invention may be admixed with an oral topical vehicle to form a topical therapeutic wound healing composition. These amounts are readily determined by those skilled in the art without the need for undue experimentation. In a preferred embodiment, the oral topical therapeutic wound healing compositions will comprise the therapeutic wound healing composition in an amount from about 0.1% to about 10% and a oral topical vehicle in a quantity sufficient to bring the total amount of composition to 100%, by weight of the oral topical therapeutic wound healing composition. In a more preferred embodiment, the oral topical therapeutic wound healing compositions will comprise the therapeutic wound healing composition in an amount from about 0.1% to about 5%, and in a most preferred embodiment, the oral topical therapeutic wound healing compositions will comprise the therapeutic wound healing composition in an amount from about 0.1% to about 2%, and a oral topical vehicle in a quantity sufficient to bring the total amount of composition to 100%, by weight of the oral topical therapeutic wound healing composition.

The present invention extends to methods for preparing the oral topical therapeutic wound healing compositions. In such a method, the oral topical therapeutic wound healing composition is prepared by admixing a therapeutically effective amount of the therapeutic wound healing composition of the present invention and an oral topical vehicle. The final compositions are readily prepared using standard methods and apparatus generally known by those skilled in the pharmaceutical arts. The apparatus useful in accordance with the present invention comprises mixing apparatus well known in the pharmaceutical arts, and therefore the selection of the specific apparatus will be apparent to the artisan.

In a preferred embodiment, an oral topical therapeutic wound healing composition is made by first dissolving coloring agents, sweetening agents, and similar additives in water. The therapeutic wound healing composition is then admixed with the aqueous solution. Then sufficient water or ethanol, or mixtures of water and ethanol, are added to the solution with mixing until the final solution volume is reached. In a more preferred embodiment, the therapeutic wound healing composition is added to the solution as the final ingredient. The final oral topical therapeutic wound healing compositions are readily prepared using methods generally known in the pharmaceutical arts.

The oral therapeutic wound healing composition may also be in the form of dental gel. As used herein, the term "gel" means a solid or semisolid colloid which contains considerable quantities of water. The colloid particles in a gel are linked together in a coherent meshwork which immobilizes the water contained inside the meshwork.

The dental gel compositions of the present invention may contain the conventional additives set out above for oral topical therapeutic wound healing compositions such as mouthwashes, rinses, oral sprays, and suspensions and, in addition, may contain additional additives such as a polishing agent, a desensitizing agent, and the like, providing the additional additives do not interfere with the therapeutic properties of the therapeutic wound healing composition.

In a dental gel composition, the oral vehicle generally comprises water, typically in an amount from about 10% to about 90%, by weight of the dental gel composition. Polyethylene glycol, propylene glycol, glycerin, and mixtures thereof may also be present in the vehicle as humectants or binders in amounts from about 18% to about 30%, by weight of the dental gel composition. Particularly preferred oral vehicles comprise mixtures of water with polyethylene glycol or water with glycerin and polypropylene glycol.

The dental gels of the present invention include a gelling agent (thickening agent) such as a natural or synthetic gum or gelatin. Gelling agents such as hydroxyethyl cellulose, methyl cellulose, glycerin, carboxypolymethylene, and gelatin and the like, and mixtures thereof may be used. The preferred gelling agent is hydroxyethyl cellulose. Gelling agents may be used in amounts from about 0.5% to about 5%, and preferably from about 0.5% to about 2%, by weight of the dental gel composition.

The dental gel compositions of the present invention may also include a polishing agent. In clear gels, a polishing agent of colloidal silica and/or alkali metal aluminosilicate complexes is preferred since these materials have refractive indices close to the refractive indices of the gelling systems commonly used in dental gels. In non-clear gels, a polishing agent of calcium carbonate or calcium dihydrate may be used. These polishing agents may be used in amounts up to about 75%, and preferably in amounts up to about 50%, by weight of the dental gel composition.

The dental gel may also contain a desensitizing agent such as a combination of citric acid and sodium citrate. Citric acid may be used in an amount from about 0.1% to about 3%, and preferably from about 0.2% to about 1%, by weight, and sodium citrate may be used in an amount from about 0.3% to about 9%, and preferably from about 0.6% to about 3%, by weight of the dental gel composition.

In accordance with this invention, therapeutically effective amounts of the therapeutic wound healing compositions of the present invention may be admixed into the dental gel compositions. These amounts are readily determined by those skilled in the art without the need for undue experimentation. In a preferred embodiment, the dental gel compositions will comprise the therapeutic wound healing composition in an amount from about 0.1% to about 10% and an oral topical vehicle in a quantity sufficient to bring the total amount of composition to 100%, by weight of the dental gel composition. In a more preferred embodiment, the dental gel compositions will comprise the therapeutic wound healing composition in an amount from about 0.1% to about 5%, and in a most preferred embodiment, the dental gel compositions will comprise the therapeutic wound healing composition in an amount from about 0.1% to about 2%, and an oral topical vehicle in a quantity sufficient to bring the total amount of composition to 100%, by weight of the dental gel composition.

The present invention extends to methods for preparing the therapeutic dental gel compositions. In such a method, the dental gel composition is prepared by admixing a therapeutically effective amount of the therapeutic wound healing composition of the present invention and an oral topical vehicle. The final compositions are readily prepared using methods generally known by those skilled in the dental and pharmaceutical arts. The apparatus useful in accordance with the present invention comprises mixing apparatus well known in the pharmaceutical arts, and therefore the selection of the specific apparatus will be apparent to the artisan.

In a preferred embodiment, a therapeutic dental gel composition is made by first dispersing a gelling agent in a humectant or water, or a mixture of both, then admixing to the dispersion an aqueous solution of the water-soluble additives such as the fluorine providing compound, sweeteners and the like, then adding the polishing agent, and lastly admixing the flavoring agent and the therapeutic wound healing composition. The final gel mixture is then tubed or otherwise packaged. The liquids and solids in a gel product are proportioned to form a creamy or gelled mass which is extrudable from a pressurized container or from a collapsible tube. The final therapeutic wound healing compositions are readily prepared using methods generally known in the pharmaceutical arts.

In yet another form of the invention, the therapeutic wound healing composition is incorporated into an ingestible vehicle. The ingestible vehicle may be a confectionery bulldng agent in the form of lozenges, tablets, toffees, nougats, suspensions, chewy candies, chewing gums, and the like. The pharmaceutically acceptable carriers may be prepared from a wide range of materials including, but not limited to, diluents, binders and adhesives, lubricants, disintegrants, coloring agents, bulking agents, flavoring agents, sweetening agents and miscellaneous materials such as buffers and adsorbents that may be needed in order to prepare a particular therapeutic confection.

The preparation of confectionery formulations is historically well known and has changed little through the years. Confectionery items have been classified as either "hard" confectionery or "soft"confectionery. The therapeutic wound healing compositions of the present invention can be incorporated into confectionery compositions by admixing the inventive composition into conventional hard and soft confections.

As used herein, the term confectionery material means a product containing a bulking agent selected from a wide variety of materials such as sugar, corn syrup, and in the case of sugarless bulking agents, sugar alcohols such as sorbitol and mannitol and mixtures thereof. Confectionery material may include such exemplary substances as lozenges, tablets, toffee, nougat, suspensions, chewy candy, chewing gum and the like. The bulking agent is present in a quantity sufficient to bring the total amount of composition to 100%. In general, the bulking agent will be present in amounts up to about 99.98%, preferably in amounts up to about 99.9%, and more preferably in amounts up to about 99%, by weight of the ingestible therapeutic wound healing composition.

Lozenges are flavored medicated dosage forms intended to be sucked and held in the mouth. Lozenges may be in the form of various shapes such as flat, circular, octagonal and biconvex forms. The lozenge bases are generally in two forms: hard boiled candy lozenges and compressed tablet lozenges.

Hard boiled candy lozenges may be processed and formulated by conventional means. In general, a hard boiled candy lozenge has a base composed of a mixture of sugar and other carbohydrate bulking agents kept in an amorphous or glassy condition. This amorphous or glassy form is considered a solid syrup of sugars generally having from about 0.5% to about 1.5% moisture. Such materials normally contain up to about 92% corn syrup, up to about 55% sugar and from about 0.1% to about 5% water, by weight of the final composition. The syrup component is generally prepared from corn syrups high in fructose, but may include other materials. Further ingredients such as flavoring agents, sweetening agents, acidulants, coloring agents and the like may also be added.

Boiled candy lozenges may also be prepared from non-fermentable sugars such as sorbitol, mannitol, and hydrogenated corn syrup. Typical hydrogenated corn syrups are Lycasin, a commercially available product manufactured by Roquette Corporation, and Hystar, a commercially available product manufactured by Lonza, Inc. The candy lozenges may contain up to about 95% sorbitol, a mixture of sorbitol and mannitol in a ratio from about 9.5:0.5 up to about 7.5:2.5, and hydrogenated corn syrup up to about 55%, by weight of the solid syrup component.

Boiled candy lozenges may be routinely prepared by conventional methods such as those involving fire cookers, vacuum cookers, and scraped-surface cookers also referred to as high speed atmospheric cookers.

Fire cookers involve the traditional method of making a boiled candy lozenge base. In this method, the desired quantity of carbohydrate bulking agent is dissolved in water by heating the agent in a kettle until the bulking agent dissolves. Additional bulking agent may then be added and cooking continued until a final temperature of 145° C. to 156° C. is achieved. The batch is then cooled and worked as a plastic-like mass to incorporate additives such as flavors, colorants and the like.

A high-speed atmospheric cooker uses a heat-exchanger surface which involves spreading a film of candy on a heat exchange surface, the candy is heated to 165° C. to 170° C. in a few minutes. The candy is then rapidly cooled to 100° C. to 120° C. and worked as a plastic-like mass enabling incorporation of the additives, such as flavors, colorants and the like.

In vacuum cookers, the carbohydrate bulking agent is boiled to 125° C. to 132° C., vacuum is applied and additional water is boiled off without extra heating. When cooking is complete, the mass is a semi-solid and has a plastic-like consistency. At this point, flavors, colorants, and other additives are admixed in the mass by routine mechanical mixing operations.

The optimum mixing required to uniformly mix the flavoring agents, coloring agents and other additives during conventional manufacturing of boiled candy lozenges is determined by the time needed to obtain a uniform distribution of the materials. Normally, mixing times of from 4 to 10 minutes have been found to be acceptable.

Once the boiled candy lozenge has been properly tempered, it may be cut into workable portions or formed into desired shapes. A variety of forming techniques may be utilized depending upon the shape and size of the final product desired. A general discussion of the composition and preparation of hard confections may be found in H. A. Lieberman, Pharmaceutical Dosage Forms: Tablets, Volume 1 (1980), Marcel Dekker, Inc., New York, N.Y. at pages 339 to 469, which disclosure is incorporated herein by reference.

The apparatus useful in accordance with the present invention comprises cooking and mixing apparatus well known in the confectionery manufacturing arts, and therefore the selection of the specific apparatus will be apparent to the artisan.

In contrast, compressed tablet confections contain particulate materials and are formed into structures under pressure. These confections generally contain sugars in amounts up to about 95%, by weight of the composition, and typical tablet excipients such as binders and lubricants as well as flavoring agents, coloring agents and the like.

In addition to hard confectionery materials, the lozenges of the present invention may be made of soft confectionery materials such as those contained in nougat. The preparation of soft confections, such as nougat, involves conventional methods, such as the combination of two primary components, namely (1) a high boiling syrup such as a corn syrup, hydrogenated starch hydrolysate or the like, and (2) a relatively light textured frappe, generally prepared from egg albumin, gelatin, vegetable proteins, such as soy derived compounds, sugarless milk derived compounds such as milk proteins, and mixtures thereof. The frappe is generally relatively light, and may, for example, range in density from about 0.5 to about 0.7 grams/cc.

The high boiling syrup, or "bob syrup" of the soft confectionery is relatively viscous and has a higher density than the frappe component, and frequently contains a substantial amount of carbohydrate bulking agent such as a hydrogenated starch hydrolysate. Conventionally, the final nougat composition is prepared by the addition of the "bob syrup" to the frappe under agitation, to form the basic nougat mixture. Further ingredients such as flavoring agents, additional carbohydrate bulking agent, coloring agents, preservatives, medicaments, mixtures thereof and the like may be added thereafter also under agitation. A general discussion of the composition and preparation of nougat confections may be found in B. W. Minifle, Chocolate, Cocoa and Confectionery: Science and Technology, 2nd edition, AVI Publishing Co., Inc., Westport, Conn. (1980), at pages 424–425, which disclosure is incorporated herein by reference.

The procedure for preparing the soft confectionery involves known procedures. In general, the frappe component is prepared first and thereafter the syrup component is slowly added under agitation at a temperature of at least about 65° C., and preferably at least about 100° C. The mixture of components is continued to be mixed to form a uniform mixture, after which the mixture is cooled to a temperature below 80° C., at which point, the flavoring agent may be added. The mixture is further mixed for an additional period until it is ready to be removed and formed into suitable confectionery shapes.

The ingestible therapeutic wound healing compositions may also be in the form of a pharmaceutical suspension. Pharmaceutical suspensions of this invention may be prepared by conventional methods long established in the art of pharmaceutical compounding. Suspensions may contain adjunct materials employed in formulating the suspensions of the art. The suspensions of the present invention can comprise:

(a) preservatives such as butylated hydroxyanisole (BHA), butylated hydroxytoluene (BHT), benzoic acid, ascorbic acid, methyl paraben, propyl paraben, tocopherols, and the like, and mires thereof. Preservatives are generally present in amounts up to about 1%, and preferably from about 0.05% to about 0.5%, by weight of the suspension;

(b) buffers such as citric acid-sodium citrate, phosphoric acid-sodium phosphate, and acetic acid-sodium acetate in amounts up to about 1%, and preferably from about 0.05% to about 0.5%, by weight of the suspension;

(c) suspending agents or thickeners such as cellulosics like methylcellulose, carrageenans like alginic acid and its derivatives, xanthan gums, gelatin, acacis, and microcrystalline cellulose in amounts up to about 20%, and preferably from about 1% to about 15%, by weight of the suspension;

(d) antifoaming agents such as dimethyl polysiloxane in amounts up to about 0.2%, and preferably from about 0.01% to about 0.1%, by weight of the suspension;

(e) sweetening agents such as those sweeteners well known in the art, including both natural and artificial sweeteners. Sweetening agents such as monosaccharides, disaccharides and polysaccharides such as xylose, ribose, glucose (dextrose), mannose, galactose, fructose (levulose), sucrose (sugar), maltose, invert sugar (a mixture of fructose and glucose derived from sucrose), partially hydrolyzed starch, corn syrup solids, dihydrochalcones, monellin, steviosides, glycyrrhizin, and sugar alcohols such as sorbitol, mannitol, maltitol, hydrogenated starch hydrolysates and mixtures thereof may be utilized in amounts up to about 60%, and preferably from about 20% to about 50%, by weight of the suspension. Water-soluble artificial sweeteners such as soluble saccharin salts, i.e., sodium or calcium saccharin salts, cyclamate salts, the sodium, ammonium or calcium salt of 3,4-dihydro-6-methyl-1,2,3-oxathiazine4-one-2,2-dioxide, the potassium salt of 3,4-dihydro-6-methyl-1,2,3-oxathiazine4-one-2,2-dioxide (Acesulfame-K), the free acid form of saccharin, and the like may be utilized in amounts from about 0.001% to about 5%, by weight of the suspension;

(f) flavoring agents such as those flavors well known to the skilled artisan, such as natural and artificial flavors and mints, such as peppermint, menthol, citrus flavors such as orange and lemon, artificial vanilla, cinnamon, various fruit flavors, both individual and mixed and the like may be utilized in amounts from about 0.5% to about 5%, by weight of the suspension;

(g) coloring agents such as pigments which may be incorporated in amounts up to about 6%, by weight of the suspension. A preferred pigment, titanium dioxide, may be incorporated in amounts up to about 2%, and preferably less than about 1%, by weight of the suspension. The coloring agents may also include natural food colors and dyes suitable for food, drug and cosmetic applications. These colorants are known as F.D.& C. dyes and lakes. The materials acceptable for the foregoing uses are preferably water-soluble. Such dyes are generally present in amounts up to about 0.25%, and preferably from about 0.05% to about 0.2%, by weight of the suspension;

(h) decolorizing agents such as sodium metabisulfite, ascorbic acid and the like may be incorporated into the suspension to prevent color changes due to aging. In general, decolorizing agents may be used in amounts up to about 0.25%, and preferably from about 0.05% to about 0.2%, by weight of the suspension; and (i) solubilizers such as alcohol, propylene glycol, polyethylene glycol, and the like may be used to solubilize the flavoring agents. In general, solubilizing agents may be used in amounts up to about 10%, and preferably from about 2% to about 5%, by weight of the suspension.

The pharmaceutical suspensions of the present invention may be prepared as follows:

(A) admix the thickener with water heated from about 40° C. to about 95° C., preferably from about 40° C. to about 70° C., to form a dispersion if the thickener is not water soluble or a solution if the thickener is water soluble;

(B) admix the sweetening agent with water to form a solution;

(C) admix the therapeutic wound healing composition with the thickener-water admixture to form a uniform thickener-therapeutic wound healing composition;

(D) combine the sweetener solution with the thickener-therapeutic wound healing composition and mix until uniform; and (E) admix the optional adjunct materials such as coloring agents, flavoring agents, decolorants, solubilizers, antifoaming agents, buffers and additional water with the mixture of step (D) to form the suspension.

The ingestible therapeutic wound healing compositions of this invention may also be in chewable form. To achieve acceptable stability and quality as well as good taste and mouth feel in a chewable formulation several considerations are important. These considerations include the amount of active substance per tablet, the flavoring agent employed, the degree of compressibility of the tablet and the organoleptic properties of the composition.

Chewable therapeutic candy is prepared by procedures similar to those used to make soft confectionery. In a typical procedure, a boiled sugar-corn syrup blend is formed to which is added a frappe mixture. The boiled sugar-corn syrup blend may be prepared from sugar and corn syrup blended in parts by weight ratio of about 90:10 to about 10:90. The sugar-corn syrup blend is heated to temperatures above about 120° C. to remove water and to form a molten mass. The frappe is generally prepared from gelatin, egg albumin, milk proteins such as casein, and vegetable proteins such as soy protein, and the like, which is added to a gelatin solution and rapidly mixed at ambient temperature to form an aerated sponge like mass. The frappe is then added to the molten candy mass and mixed until homogeneous at temperatures between about 65° C. and about 120° C.

The ingestible therapeutic wound healing composition of the instant invention can then be added to the homogeneous mixture as the temperature is lowered to about 65° C.–95° C. whereupon additional ingredients can then be added such as flavoring agents and coloring agents. The formulation is further cooled and formed into pieces of desired dimensions.

A general discussion of the lozenge and chewable tablet forms of confectionery may be found in H. A. Lieberman and L. Lachman, Pharmaceutical Dosage Forms: Tablets Volume 1, Marcel Dekker, Inc., New York, N.Y. at pages 289 to 466, which disclosure is incorporated herein by reference.

In accordance with this invention, therapeutically effective amounts of the therapeutic wound healing compositions of the present invention may be admixed into the hard and soft confectionery products. These amounts are readily determined by those skilled in the art without the need for undue experimentation. In a preferred embodiment, the ingestible therapeutic wound healing composition will comprise the therapeutic wound healing composition in an amount from about 0.1% to about 10% and an ingestible vehicle, that is a pharmaceutically acceptable carrier, in a quantity sufficient to bring the total amount of composition to 100%, by weight the ingestible therapeutic wound healing composition. In a more preferred embodiment, the ingestible composition will comprise the therapeutic wound healing composition in an amount from about 0.1% to about 5%, and in a most preferred embodiment, the ingestible composition will comprise the therapeutic wound healing composition in an amount from about 0.1% to about 2%, and an ingestible vehicle in a quantity sufficient to bring the total amount of composition to 100%, by weight the ingestible therapeutic wound healing composition.

The present invention extends to methods of making the ingestible therapeutic wound healing compositions. In such methods, an ingestible therapeutic wound healing composition is prepared by admixing a therapeutically effective amount of the therapeutic wound healing composition with a pharmaceutically-acceptable carrier. The apparatus useful in accordance with the present invention comprises mixing and heating apparatus well known in the confectionery arts, and therefore the selection of the specific apparatus will be apparent to the artisan. The final ingestible therapeutic wound healing compositions are readily prepared using methods generally known in the confectionery arts.

The therapeutic wound healing compositions may also be incorporated into chewing gums. In this form of the invention, the chewing gum composition contains a gum base, a bulking agent, the inventive therapeutic wound healing composition, and various additives.

The gum base employed will vary greatly depending upon various factors such as the type of base desired, the consistency of gum desired and the other components used in the composition to make the final chewing gum product. The gum base may be any water-insoluble gum base known in the art, and includes those gum bases utilized for chewing gums and bubble gums. Illustrative examples of suitable polymers in gum bases include both natural and synthetic elastomers and rubbers. For example, those polymers which are suitable as gum bases include, without limitation, substances of vegetable origin such as chicle, crown gum, nispero, rosadinha, jelutong, perillo, niger gutta, tunu, balata, gutta-percha, lechi-capsi, sorva, gutta kay, mixtures thereof and the like. Synthetic elastomers such as butadiene-styrene copolymers, polyisobutylene, isobutylene-isoprene copolymers, polyethylene, mixtures thereof and the like are particularly useful.

The gum base may include a non-toxic vinyl polymer, such as polyvinyl acetate and its partial hydrolysate, polyvinyl alcohol and mixtures thereof. When utilized, the molecular weight of the vinyl polymer may range from about 2,000 up to and including about 94,000.

The amount of gum base employed will vary greatly depending upon various factors such as the type of base used, the consistency of the gum desired and the other components used in the composition to make the final chewing gum product. In general, the gum base will be present in amounts from about 5% to about 94%, by weight of the final chewing gum composition, and preferably in amounts from about 15% to about 45%, and more preferably in amounts from about 15% to about 35%, and most preferably in amounts from about 20% to about 30%, by weight of the final chewing gum composition.

The gum base composition may contain conventional elastomer solvents to aid in softening the elastomer base component. Such elastomer solvents may comprise terpinene resins such as polymers of α-pinene or β-pinene, methyl, glycerol or pentaerythritol esters of rosins or modified rosins and gums, such as hydrogenated, dimerized or polymerized rosins or mixtures thereof. Examples of elastomer solvents suitable for use herein include the pentaerythritol ester of partially hydrogenated wood or gum rosin, the pentaerythritol ester of wood or gum rosin, the glycerol ester of wood rosin, the glycerol ester of partially dimerized wood or gum rosin, the glycerol ester of polymerized wood or gum rosin, the glycerol ester of tall oil rosin, the glycerol ester of wood or gum rosin and the partially hydrogenated wood or gum rosin and the partially hydrogenated methyl ester of wood or rosin, mixtures thereof, and the like. The elastomer solvent may be employed in amounts from about 5% to about 75%, by weight of the gum base, and preferably from about 45% to about 70%, by weight of the gum base.

A variety of traditional ingredients may be included in the gum base in effective amounts such as plasticizers or softeners such as lanolin, palmitic acid, oleic acid, stearic acid, sodium stearate, potassium stearate, glyceryl triacetate, glyceryl lecithin, glyceryl monostearate, propylene glycol monostearate, acetylated monoglyceride, glycerine, mixtures thereof, and the like may also be incorporated into the gum base to obtain a variety of desirable textures and consistency properties. Waxes, for example, natural and synthetic waxes, hydrogenated vegetable oils, petroleum waxes such as polyurethane waxes, polyethylene waxes, paraffin waxes, microcrystalline waxes, fatty waxes, sorbitan monostearate, tallow, propylene glycol, mixtures thereof, and the like may also be incorporated into the gum base to obtain a variety of desirable textures and consistency properties. These traditional additional materials are generally employed in amounts up to about 30%, by weight of the gum base, and preferably in amounts from about 3% to about 20%, by weight of the gum base.

The gum base may include effective amounts of mineral adjuvants such as calcium carbonate, magnesium carbonate, alumina, aluminum hydroxide, aluminum silicate, talc, tricalcium phosphate, dicalcium phosphate and the like as well as mixtures thereof. These mineral adjuvants may serve as fillers and textural agents. These fillers or adjuvants may be used in the gum base in various amounts. Preferably the amount of filler when used will be present in an amount up to about 60%, by weight of the chewing gum base.

The chewing gum base may additionally include the conventional additives of coloring agents, antioxidants, preservatives and the like. For example, titanium dioxide and other dyes suitable for food, drug and cosmetic applications, known as F.D. & C. dyes, may be utilized. An antioxidant such as butylated hydroxytoluene (BHT), butylated hydroxyanisole (BHA), propyl gallate, and mixtures thereof may also be included. Other conventional chewing gum additives known to one having ordinary skill in the chewing gum art may also be used in the chewing gum base.

The gum composition may include effective amounts of conventional additives selected from the group consisting of sweetening agents (sweeteners), plasticizers, softeners, emulsifiers, waxes, fillers, bulking agents, mineral adjuvants, flavoring agents (flavors, flavorings), coloring agents (colorants, colorings), antioxidants, acidulants, thickeners, mixtures thereof and the like. Some of these additives may serve more than one purpose. For example, in sugarless gum compositions, the sweetener, e.g., sorbitol or other sugar alcohol or mixtures thereof, may also function as a bulking agent. Similarly, in sugar containing gum compositions, the sugar sweetener can also function as a bulking agent.

The plasticizers, softeners, mineral adjuvants, colorants, waxes and antioxidants discussed above as being suitable for use in the gum base may also be used in the gum composition. Examples of other conventional additives which may be used include emulsifiers, such as lecithin and glyceryl monostearate, thickeners, used alone or in combination with other softeners, such as methyl cellulose, alginates, carrageenan, xanthan gum, gelatin, carob, tragacanth, locust bean, and carboxy methyl cellulose, acidulants such as malic acid, adipic acid, citric acid, tartaric acid, fumaric acid, and mixtures thereof, and fillers, such as those discussed above under the category of mineral adjuvants. The fillers when used may be utilized in an amount up to about 60%, by weight of the gum composition.

Bulking agents (carriers, extenders) suitable for use in chewing gums include sweetening agents selected from the group consisting of monosaccharides, disaccharides, polysaccharides, sugar alcohols, and mixtures thereof; polydextrose; maltodextrins; minerals, such as calcium carbonate, talc, titanium dioxide, dicalcium phosphate, and the like. Bulking agents may be used in amounts up to about 90%, by weight of the final gum composition, with amounts from about 40% to about 70%, by weight of the gum composition being preferred, with from about 50% to about 65%, by weight, being more preferred and from about 55% to about 60%, by weight of the chewing gum composition, being most preferred.

The sweetening agent used may be selected from a wide range of materials including water-soluble sweeteners, water-soluble artificial sweeteners, water-soluble sweeteners derived from naturally occurring water-soluble sweeteners, dipeptide based sweeteners, and protein based sweeteners, including mixtures thereof. Without being limited to particular sweeteners, representative categories and examples include:

(a) water-soluble sweetening agents such as monosaccharides, disaccharides and polysaccharides such as xylose, ribulose, glucose (dextrose), mannose, galactose, fructose (levulose), sucrose (sugar), maltose, invert sugar (a mixture of fructose and glucose derived from sucrose), partially hydrolyzed starch, corn syrup solids, dihydrochalcones, monellin, steviosides, glycyrrhizin, and sugar alcohols such as sorbitol, mannitol, maltitol, hydrogenated starch hydrolysates and mixtures thereof;

(b) water-soluble artificial sweeteners such as soluble saccharin salts, i.e., sodium or calcium saccharin salts, cyclamate salts, the sodium, ammonium or calcium salt of 3,4-dihydro-6-methyl-1,2,3-oxathiazine4one-2,2-dioxide, the potassium salt of 3,4-dihydro-6-methyl-1,2,3-oxathiazine-4-one-2,2-dioxide (Acesulfame-K), the free acid form of saccharin, and the like;

(c) dipeptide based sweeteners, such as L-aspartic acid derived sweeteners, such as L-aspartyl-L-phenylalanine methyl ester (Aspartame) and materials described in U.S. Pat. No. 3,492,131, L-α-aspartyl-N-(2,2,4,4-tetramethyl-3- thietanyl)-D-alanin-amide hydrate (Alitame), methyl esters of L-aspartyl-L-phenylglycerine and L-aspartyl-L-2,5-dihydrophenyl-glycine, L-aspartyl-2,5-dihydro-L-phenylalanine; L-aspartyl-L-(1-cyclohexen)-alanine, and the like;

(d) water-soluble sweeteners derived from naturally occurring water-soluble sweeteners, such as chlorinated derivatives of ordinary sugar (sucrose), known, for example, under the product designation of Sucralose; and (e) protein based sweeteners such as thaumaoccous danielli (Thaumatin I and II).

In general, an effective amount of sweetener is utilized to provide the level of bulk and/or sweetness desired, and this amount will vary with the sweetener selected. This amount of sweetener will normally be present in amounts from about 0.0025% to about 90%, by weight of the gum composition, depending upon the sweetener used. The exact range of amounts for each type of sweetener is well known in the art and is not the subject of the present invention. The amount of sweetener ordinarily necessary to achieve the desired level of sweetness is independent from the flavor level achieved from flavor oils.

Preferred sugar based-sweeteners are sugar (sucrose), corn syrup and mixtures thereof. Preferred sugarless sweeteners are the sugar alcohols, artificial sweeteners, dipeptide based sweeteners and mixtures thereof. Preferably, sugar alcohols are used in the sugarless compositions because these sweeteners can be used in amounts which are sufficient to provide bulk as well as the desired level of sweetness. Preferred sugar alcohols are selected from the group consisting of sorbitol, xylitol, maltitol, mannitol, and mixtures thereof. More preferably, sorbitol or a mixture of sorbitol and mannitol is utilized. The γ form of sorbitol is preferred. An artificial sweetener or dipeptide based sweetener is preferably added to the gum compositions which contain sugar alcohols.

The coloring agents useful in the gum compositions are used in amounts effective to produce the desired color. These coloring agents include pigments which may be incorporated in amounts up to about 6% by weight of the gum composition. A preferred pigment, titanium dioxide, may be incorporated in amounts up to about 2%, and preferably less than about 1% by weight of the composition. The colorants may also include natural food colors and dyes suitable for food, drug and cosmetic applications. These colorants are known as F.D.& C. dyes and lakes. The materials acceptable for the foregoing uses are preferably water-soluble. Illustrative nonlirniting examples include the indigoid dye known as F.D.& C. Blue No.2, which is the disodium salt of 5,5-indigotindisulfonic acid. Similarly, the dye known as F.D.& C. Green No.1 comprises a triphenylmethane dye and is the monosodium salt of 4-[4-(N-ethyl-p-sulfoniumbenzylamino) diphenylmethylene]-[1-N-ethyl-N-p-sulfoniumbenzyl)-δ-2,5-cyclohexadieneimine]. A full recitation of all F.D.& C. colorants and their corresponding chemical structures may be found in the Kirk-Othmer Encyclopedia of Chemical Technology, 3rd Edition, in volume 5 at pages 857–884, which text is incorporated herein by reference.

Suitable oils and fats usable in gum compositions include partially hydrogenated vegetable or animal fats, such as coconut oil, palm kernel oil, beeftallow, lard, and the like. These ingredients when used are generally present in amounts up to about 7%, by weight, and preferably up to about 3.5%, by weight of the gum composition.

In accordance with this invention, therapeutically effective amounts of the therapeutic wound healing compositions of the present invention may be admixed into a chewing gum. These amounts are readily determined by those skilled in the art without the need for undue experimentation. In a preferred embodiment, the final chewing gum composition will comprise the therapeutic wound healing composition in an amount from about 0.1% to about 10% and a chewing gum composition in a quantity sufficient to bring the total amount of composition to 100%, by weight of the chewing gum composition. In a more preferred embodiment, the final chewing gum composition will comprise the therapeutic wound healing composition in an amount from about 0.1% to about 5%, and in a most preferred embodiment, the final chewing gum composition will comprise the therapeutic wound healing composition in an amount from about 0.1% to about 2%, and a chewing gum composition in a quantity sufficient to bring the total amount of composition to 100%, by weight of the chewing gum composition.

The present invention extends to methods of making the therapeutic chewing gum compositions. The therapeutic wound healing compositions may be incorporated into an otherwise conventional chewing gum composition using standard techniques and equipment known to those skilled in the art. The apparatus useful in accordance with the present invention comprises mixing and heating apparatus well known in the chewing gum manufacturing arts, and therefore the selection of the specific apparatus will be apparent to the artisan.

For example, a gum base is heated to a temperature sufficiently high enough to soften the base without adversely effecting the physical and chemical make up of the base. The optimum temperatures utilized may vary depending upon the composition of the gum base used, but such temperatures are readily determined by those skilled in the art without undue experimentation.

The gum base is conventionally melted at temperatures that range from about 60° C. to about 120° C. for a period of time sufficient to render the base molten. For example, the gum base may be heated under these conditions for a period of about thirty minutes just prior to being admixed incrementally with the remaining ingredients of the base such as the plasticizer, fillers, the bulking agent and/or sweeteners, the softener and coloring agents to plasticize the blend as well as to modulate the hardness, viscoelasticity and formability of the base. The chewing gum base is then blended with the therapeutic wound healing composition of the present invention which may have been previously blended with other traditional ingredients. Mixing is continued until a uniform mixture of gum composition is obtained. Thereafter the gum composition mixture may be formed into desirable chewing gum shapes.

In a specific embodiment, the invention is directed to a therapeutic pharmaceutical composition for preventing and reducing injury to mammalian cell, and increasing the resuscitation rate of injured mammalian cells, which comprises:

(A) a therapeutically effective amount of a therapeutic wound healing composition of Embodiment One (I) selected from the group consisting of:

(I.A)

(1)
(a) pyruvate selected from the group consisting of pyruvic acid, pharmaceutically acceptable salts of pyruvic acid, and mixtures thereof;
(b) an antioxidant; and
(c) a mixture of saturated and unsaturated fatty acids wherein the fatty acids are those fatty acids required for the repair of cellular membranes and resuscitation of mammalian cells;

(I.B)

(2)
(a) pyruvate selected from the group consisting of pyruvic acid, pharmaceutically acceptable salts of pyruvic acid, and mixtures thereof;
(b) lactate selected from the group consisting of lactic acid, pharmaceutically acceptable salts of lactic acid, and mixtures thereof; and
(c) a mixture of saturated and unsaturated fatty acids wherein the fatty acids are those fatty acids required for the repair of cellular membranes and resuscitation of mammalian cells;

(I.C)

(3)
(a) an antioxidant; and
(b) a mixture of saturated and unsaturated fatty acids wherein the fatty acids are those fatty acids required for the repair of cellular membranes and resuscitation of mammalian cells;

(I.D)

(4)
(a) lactate selected from the group consisting of lactic acid, pharmaceutically acceptable salts of lactic acid, and mixtures thereof;
(b) an antioxidant; and
(c) a mixture of saturated and unsaturated fatty acids wherein the fatty acids are those fatty acids required for the repair of cellular membranes and resuscitation of mammalian cells; and
(B) a pharmaceutically acceptable carrier.

The pharmaceutically acceptable carrier may be selected from the group consisting of pharmaceutical appliances, topical vehicles, and ingestible vehicle.

In another specific embodiment, the invention is directed to a method for preparing a therapeutic pharmaceutical composition for preventing and reducing injury to mammalian cells, and increasing the resuscitation rate of injured mammalian cells, which comprises the steps of:
(A) providing a therapeutically effective amount of a therapeutic wound healing composition of Embodiment One (I) selected from the group consisting of (I.A)

(1)
(a) pyruvate selected from the group consisting of pyruvic acid, pharmaceutically acceptable salts of pyruvic acid, and mixtures thereof;
(b) an antioxidant; and
(c) a mixture of saturated and unsaturated fatty acids wherein the fatty acids are those fatty acids required for the repair of cellular membranes and resuscitation of mammalian cells;

(I.B)

(2)
(a) pyruvate selected from the group consisting of pyruvic acid, pharmaceutically acceptable salts of pyruvic acid, and mixtures thereof;

(b) lactate selected from the group consisting of lactic acid, pharmaceutically acceptable salts of lactic acid, and mixtures thereof; and
(c) a mixture of saturated and unsaturated fatty acids wherein the fatty acids are those fatty acids required for the repair of cellular membranes and resuscitation of mammalian cells;

(I.C)

(3)
(a) an antioxidant; and
(b) a mixture of saturated and unsaturated fatty acids wherein the fatty acids are those fatty acids required for the repair of cellular membranes and resuscitation of mammalian cells;

(I.D)

(4)
(a) lactate selected from the group consisting of lactic acid, pharmaceutically acceptable salts of lactic acid, and mixtures thereof;
(b) an antioxidant; and
(c) a mixture of saturated and unsaturated fatty acids wherein the fatty acids are those fatty acids required for the repair of cellular membranes and resuscitation of mammalian cells; and
(B) providing a pharmaceutically acceptable carrier; and
(C) admixing the therapeutic wound healing composition from step (A) and the pharmaceutically acceptable carrier from step (B) to form a therapeutic pharmaceutical composition.

Throughout this application, various publications have been referenced. The disclosures in these publications are incorporated herein by reference in order to more fully describe the state of the art.

The present invention is further illustrated by the following examples which are not intended to limit the effective scope of the claims. All parts and percentages in the examples and throughout the specification and claims are by weight of the final composition unless otherwise specified.

E. Examples Of The Wound Healing Compositions Of Embodiment One (I.A–D)

Study 1

This study demonstrates a comparison of the viability of U937 monocytic cells after exposure of the cells to various antioxidants and combinations of antioxidants. This study also demonstrate a comparison of the levels of hydrogen peroxide produced by U937 monocytic cells and mammalian epidermal keratinocytes after exposure of the cells to various antioxidants and combinations of antioxidants. The results of this study are illustrated in FIGS. 1–4 and examples 1–26 below.

Mammalian epidermal keratinocytes and monocytes were employed to examine the ability of various antioxidants to reduce levels of hydrogen peroxide in these cells. Hydrogen peroxide was measured after the cells were exposed to ultraviolet light in the wavelength range from 290 to 320 nm (UV-B) or to the inflammatory compound 12-0-tetradecanoyl-phorbol-13-acetate (TPA). Sodium pyruvate was tested at various concentrations to determine the effect of concentrations of this antioxidant on the hydrogen peroxide production by epidermal cells and monocytes. Magnesium pyruvate, calcium pyruvate, zinc pyruvate, and combinations of sodium pyruvate with ascorbic acid, lactic acid, and Vitamin E were then tested to determine the effect of these salts and combinations of antioxidants on the hydrogen peroxide production by epidermal cells and monocytes.

Mammalian epidermal keratinocytes were isolated by trypsinization of epithelial sheets and grown in modified basal MCDB 153 medium supplemented with epidermal growth factor, bovine pituitary extract, and hydrocortisone. Cells were maintained in a humidified incubator with 5% carbon dioxide at 37° C. Keratinocytes were seeded in 60 mm culture dishes at a cell density of $3 \times 10^5$ cells per dish and the cultures were exposed to 1 M.E.D. dose of ultraviolet-B light (100 MJ/cm$^2$) or treated with 100 ng/ml of TPA.

U937 monocytic cells are a cultured cell line grown in RPMI media with 10% fetal calf serum. Cells were maintained in a 60 mm culture dish at 5% carbon dioxide at 37 ° C. at a seeding density not exceeding $1 \times 10^6$ cells per dish.

Sodium pyruvate, lactic acid, ascorbic acid, and Vitamin E were dissolved in distilled water, with sufficient surfactant. The concentrations of the sodium pyruvate solutions prepared were 1 mM, 10 mM, 50 mM, 100 mM, and 200 mM. The concentrations of the lactic acid solutions prepared were 1.0%, 0.1%, and 0.05%. The concentrations of the ascorbic acid solutions prepared were 1.0%, 0.1%, 0.05%, and 0.025%. The concentrations of the Vitamin E solutions prepared were 1 U, 10 U, 50 U, and 100 U. The test solutions were adjusted to a pH value of 7.4 with 1.0 N sodium hydroxide solution and then sterile filtered. The appropriate concentration of test solution or combination of test solutions was added to the cells immediately prior to exposure of the cells to ultraviolet light-B or TPA [100 ng/ml]. Stock solutions were prepared so that the vehicle did not constitute more than 1% of the total volume of the culture media.

Intracellular hydrogen peroxide production by mammalian epidermal keratinocytes and U937 monocytes was measured using dichlorofluorescein diacetate (DCFH-DA, Molecular Probes, Eugene, Oreg.). DCFH-DA is a non-polar non-fluorescent compound that readily diffuses into cells where it is hydrolyzed to the polar non-fluorescent derivative DCFH which then becomes trapped within the cells. In the presence of intracellular hydrogen peroxide, DCFH is oxidized to the highly fluorescent compound DCF. Hence, cellular fluorescence intensity is directly proportional to the level of intracellular hydrogen peroxide produced. Cellular fluorescence intensity can be monitored by fluorimetry and by flow cytometry.

Mammalian epidermal keratinocytes and U937 cultured monocytes (1×106 per dish) were incubated at 37° C. with 5 uM of DCFH-DA. Production of hydrogen peroxide was measured using a Coulter Profile analytical flow cytometer. Linear and log intensity of green fluorescence data was collected. For each analysis, a quantity of 10,000 to 20,000 events was accumulated. Optical alignment for the instrument was performed daily. Coefficients of variation for forward angle light scatter and integrated green fluorescence were generally less than two. Each analysis was repeated three times and the quantitation of fluorescence was expressed in terms of femtomoles (fmol, $10^{-15}$ moles) of DCF oxidized per cell, which is a direct measure of the intracellular hydrogen peroxide produced. Alternatively, in the saturated and unsaturated fatty acid examples in examples 27–52, fluorimetry was used to assess the DCF oxidation per cell.

Figure 2:
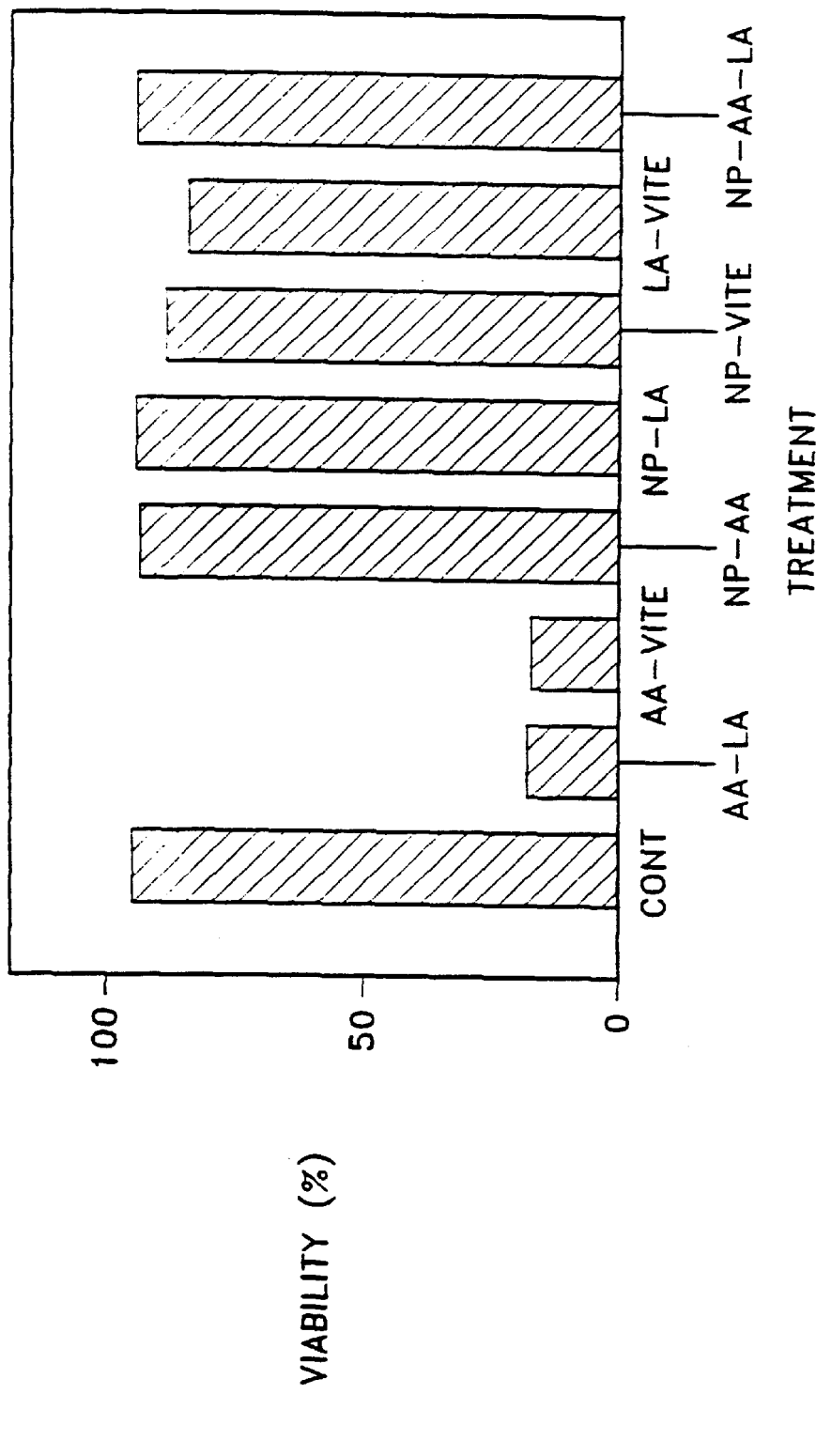
FIG. 2 depicts in bar graph format the viability of U937 monocytic cells following exposure of the cells to various combinations of antioxidants (Examples 6–13).

The viability of the U937 monocytic cells after exposure of the cells to various antioxidants for 24 hours was measured. The viability of the cells was determined by exposing the cells to the dye propidium iodide. Permeable cell membranes which absorbed the dye were not considered viable. The viability of the cells was represented as the percentage of cells that excluded propidium iodide. FIG. 1 depicts in bar graph format the viability of U937 monocytic cells after exposure of the cells to no antioxidant (Example 1, control), to sodium pyruvate (Example 2), to ascorbic acid (Example 3), to lactic acid (Example 4), and to Vitamin E (Example 5). FIG. 2 depicts in bar graph format the viability of U937 monocytic cells after exposure of the cells to various combinations of antioxidants. Specifically, the viability of U937 monocytic cells was measured after exposure to no antioxidant (Example 6, control), to ascorbic acid and lactic acid (Example 7), to ascorbic acid and Vitamin E (Example 8), to sodium pyruvate and ascorbic acid (Example 9), to sodium pyruvate and lactic acid (Example 10), to sodium pyruvate and Vitamin E (Example 11), to lactic acid and Vitamin E (Example 12), and to sodium pyruvate, ascorbic acid, and lactic acid (Example 13).

FIG. 1 shows that ascorbic acid is cytotoxic to monocytes at concentrations as low as 0.25%. FIG. 2 shows that the cytotoxicity of ascorbic acid was reversed by the addition of 10 mM of sodium pyruvate. FIGS. 1 and 2 show that the viability rate of 15% to 20% of the cells when treated with ascorbic acid was increased to 95% to 98% upon addition of sodium pyruvate. Lactic acid and Vitamin E did not reverse the cytotoxicity of ascorbic acid.

Sodium pyruvate was then tested at various concentrations to determine the effect of concentrations of this antioxidant on the hydrogen peroxide production by epidermal cells and monocytes. Mammalian epidermal keratinocytes and monocytes were exposed to (a) 1 M.E.D. dose of ultraviolet light-B and (b) 100 ng/ml of 12-0-tetradecanoylphorbol-13-acetate (TPA) in the presence of sodium pyruvate at the following concentrations: 200 mM, 100 mM, 50 mM, 10 mM, 1 mM.

The optimum concentration of sodium pyruvate to reduce the hydrogen peroxide production by epidermal cells and monocytes was found to be 10 mM. Concentrations of sodium pyruvate of 50 mM and above were cytotoxic to both epidermal keratinocytes and monocytes.

Magnesium pyruvate, calcium pyruvate, zinc pyruvate, ascorbic acid, lactic acid, and Vitamin E, and combinations of sodium pyruvate with ascorbic acid, lactic acid, and Vitamin E were then tested to determine the effect of these salts and combinations of antioxidants on the hydrogen peroxide production by epidermal cells and monocytes. The following test solutions were prepared.

(a) sodium pyruvate [10 mM];

(b) zinc salt [10 mM];

(c) magnesium salt [10 mM];

(d) calcium salt [10 mM];

(e) sodium pyruvate [10 mM] and ascorbic acid [0.025%];

(f) sodium pyruvate [10 mM] and lactic acid [0.05%];

(g) sodium pyruvate [10 mM], lactic acid, [0.05%], and ascorbic acid [0.025%];

(h) lactic acid [1.0%, 0.1%, and 0.05%];

(i) ascorbic acid [1.0%, 0.1%, 0.05%, and 0.025%];

Vitamin E [1 U, 10 U, 50 U, and 100 U]; and (k) vehicle solvent controls.

There was no significant difference among the zinc, magnesium, and calcium salts of pyruvic acid on the hydrogen peroxide production by epidermal cells and monocytes.

The zinc and calcium salts of pyruvic acid induced differentiation of keratinocytes. For convenience, the sodium salt was used in subsequent tests.

The optimum concentration of lactic acid to reduce the hydrogen peroxide production by epidermal cells and monocytes was found to be 0.05%. The optimum concentration of ascorbic acid was found to be 0.025%. The higher concentrations of both of these compounds were found to be cytotoxic to both types of cells. The optimum concentration of Vitamin E was found to be 50 U.

Figure 3:
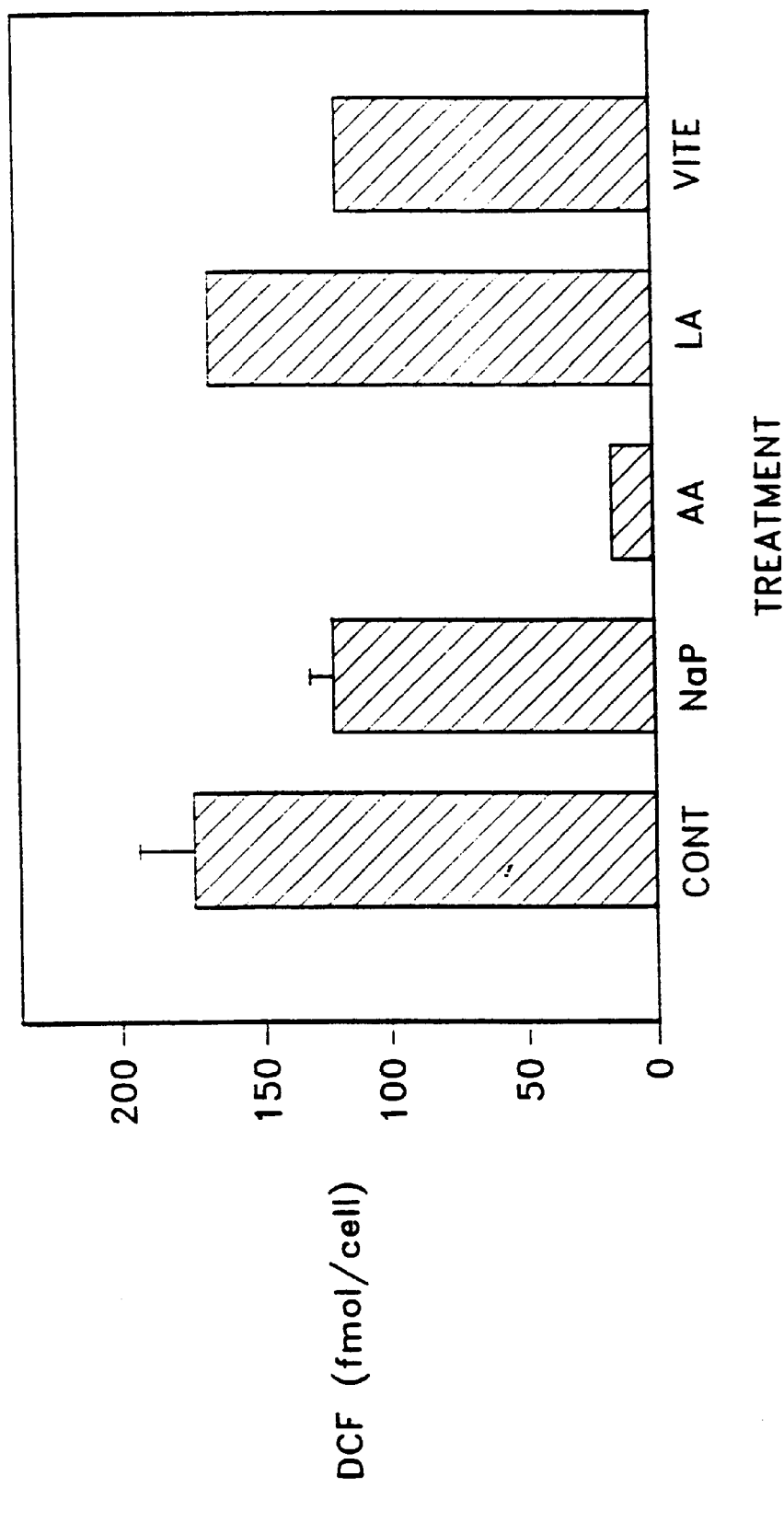
FIG. 3 depicts in bar graph format the levels of hydrogen peroxide produced by U937 monocytic cells following exposure of the cells to various antioxidants (Examples 14–18).

FIG. 3 depicts in bar graph format the levels of hydrogen peroxide produced by U937 monocytic cells after exposure of the cells to no antioxidant (Example 14, control), to sodium pyruvate (Example 15), to ascorbic acid (Example 16), to lactic acid (Example 17), and to Vitamin E (Example 18). Sodium pyruvate and Vitamin E significantly reduced the hydrogen peroxide production by monocytes.

Figure 4:
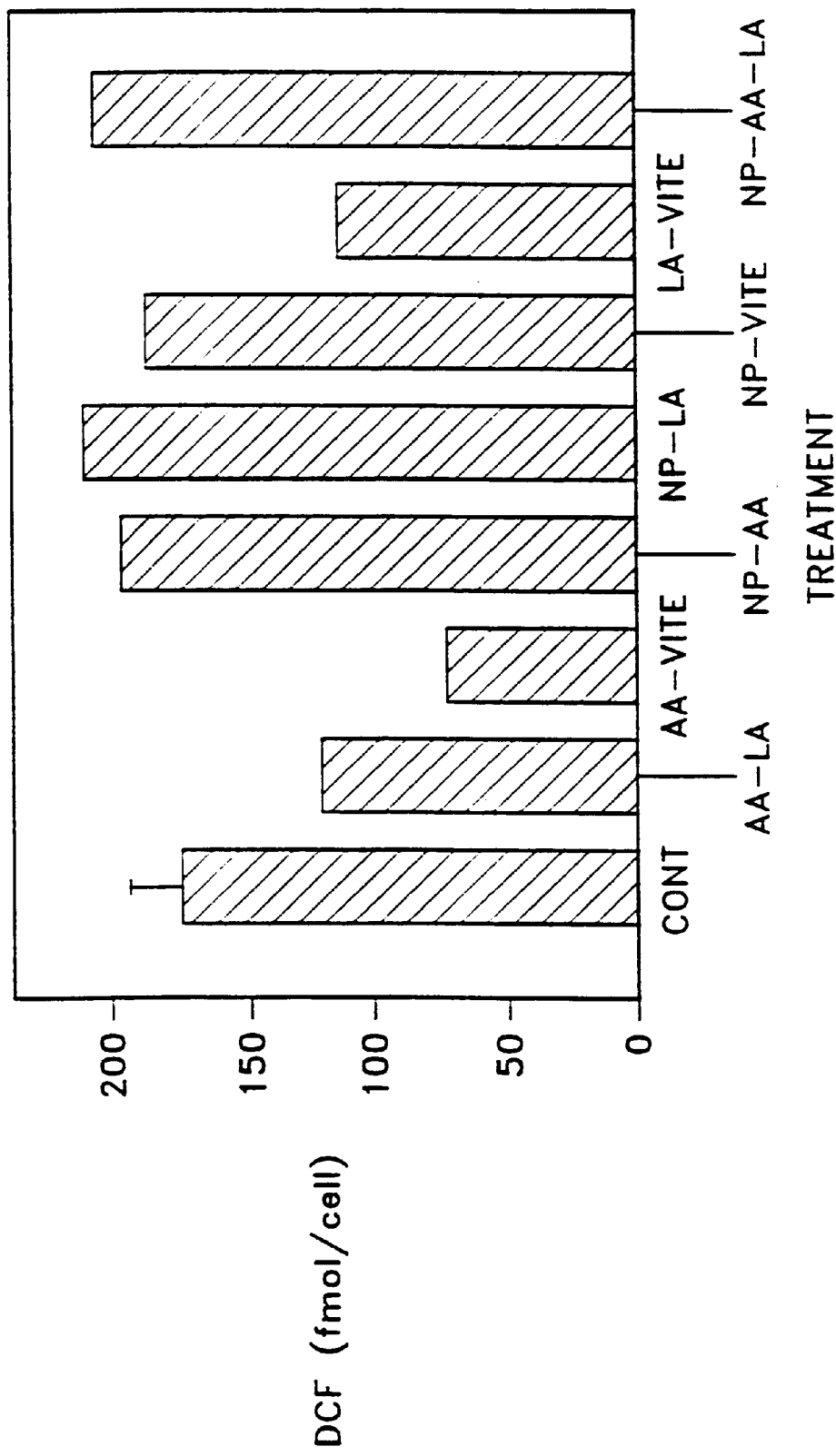
FIG. 4 depicts in bar graph format the levels of hydrogen peroxide produced by U937 monocytic cells following exposure of the cells to various combinations of antioxidants (Examples 19–26).

FIG. 4 depicts in bar graph format the levels of hydrogen peroxide produced by U937 monocytic cells after exposure of the cells to various combinations of antioxidants. Specifically, the levels of hydrogen peroxide produced by U937 monocytic cells were measured after exposure to no antioxidant (Example 19, control), to ascorbic acid and lactic acid (Example 20), to ascorbic acid and Vitamin E (Example 21), to sodium pyruvate and ascorbic acid (Example 22), to sodium pyruvate and lactic acid (Example 23), to sodium pyruvate and Vitamin E (Example 24), to lactic acid and Vitamin E (Example 25), and to sodium pyruvate, ascorbic acid, and lactic acid (Example 26). The combination of lactic acid (0.05%) and Vitamin E (50 U) significantly reduced the hydrogen peroxide production by monocytes.

The morphological alterations in epidermal keratinocytes were observed in control cultures and in cultures exposed to ultraviolet-B. Cells in the layer closest to the dermis are basal keratinocytes. These cells proliferate and migrate into the spinous and granular layers of the epidermis where the cells begin to differentiate. The differentiation pattern results in cells enucleating and forming cornified envelopes at the uppermost portion of the epidermis, the statum corneum. The differentiation of keratinocytes is controlled by the levels of calcium, magnesium, and other elements in the medium. Cells in culture systems promoting differentiation appear as an epidermal sheet forming attachments or tight junctions with each other. Keratinocytes that become nonadherent or float in the media were considered responding to a cytotoxic event.

The following morphological alterations in the mammalian epidermal keratinocytes were observed for the following control cultures:

10 mM Sodium Pyruvate: Tight junctions of cells were formed and the proliferation rate of the cells was higher than the rate of the control cells.

0.025% Ascorbic Acid: Cells were floating in a cytotoxic response to ascorbic acid.

0.025% Ascorbic acid and 10 mM Sodium Pyruvate: Few tight junctions of cells were observed and cells appeared similar to the cells in the sodium pyruvate culture.

0.05% Lactic Acid: Cells appeared dramatically altered as an epidermal sheet and as flat granular cells.

0.05% Lactic Acid and 10 mM Sodium Pyruvate: Cells formed an epidermal sheet but appeared smaller than the cell in the lactic acid culture.

50 U Vitamin E: Cells appeared the same as the cells in the control culture.

50 U Vitamin E and 10 mM Sodium Pyruvate: Cells increased in number and changed in appearance resembling the cells in the sodium pyruvate culture.

The following morphological alterations in the mammalian epidermal keratinocytes were observed for the corresponding cultures exposed to ultraviolet light-B, 100 mJoules, for 24 hours:

10 mM Sodium Pyruvate: Cells proliferated more rapidly than the cells in the control culture.

0.025% Ascorbic Acid: Cells were nonadherent and floating in a cytotoxic response to ascorbic acid greater than the cytotoxic response of the corresponding cells without ultraviolet-B light exposure.

0.05% Lactic Acid: Cells formed an epidermal sheet and were more granular than cells in the control culture without ultraviolet-B light exposure.

50 U Vitamin E: Cell growth was inhibited but cells appeared similar to cells in the control culture without ultraviolet-B light exposure.

50 U Vitamin E and 10 mM Sodium Pyruvate: Cells appeared similar to cells in the control culture and proliferated to a greater extent than cells in the control cultures without ultraviolet-B light exposure.

Morphological alterations in the U937 monocytic cell line were also observed for control cultures and cultures exposed to ultraviolet light-B, 100 mJoules, for 24 hours. The following compounds and combination of compounds, at the concentrations set out below, significantly inhibited the levels of hydrogen peroxide produced by U937 monocytic cells Sodium pyruvate at 10 mM and 50 mM;

Vitamin E at 50 U and 100 U; and

Lactic acid at 0.05% and Vitamin E at 50 U.

E. (continued) Examples Of The Wound Healing Compositions Of Embodiment One (I.A–D)

Study 2

Figure 5:
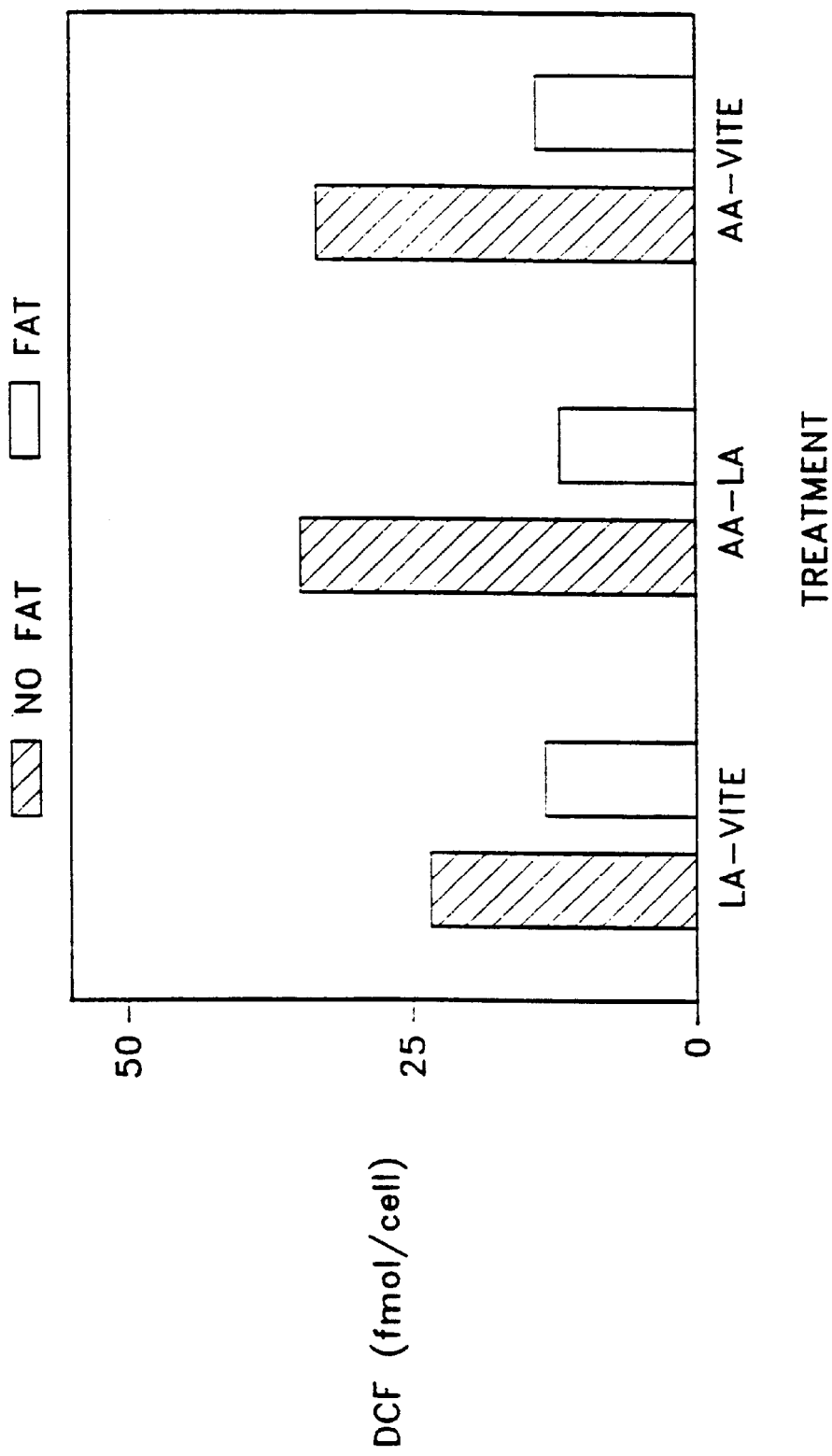
FIG. 5 depicts in bar graph format the levels of hydrogen peroxide produced by U937 monocytic cells following exposure of the cells to various combinations of antioxidants with and without a mixture of saturated and unsaturated fatty acids (Examples 27–32).
Figure 6:
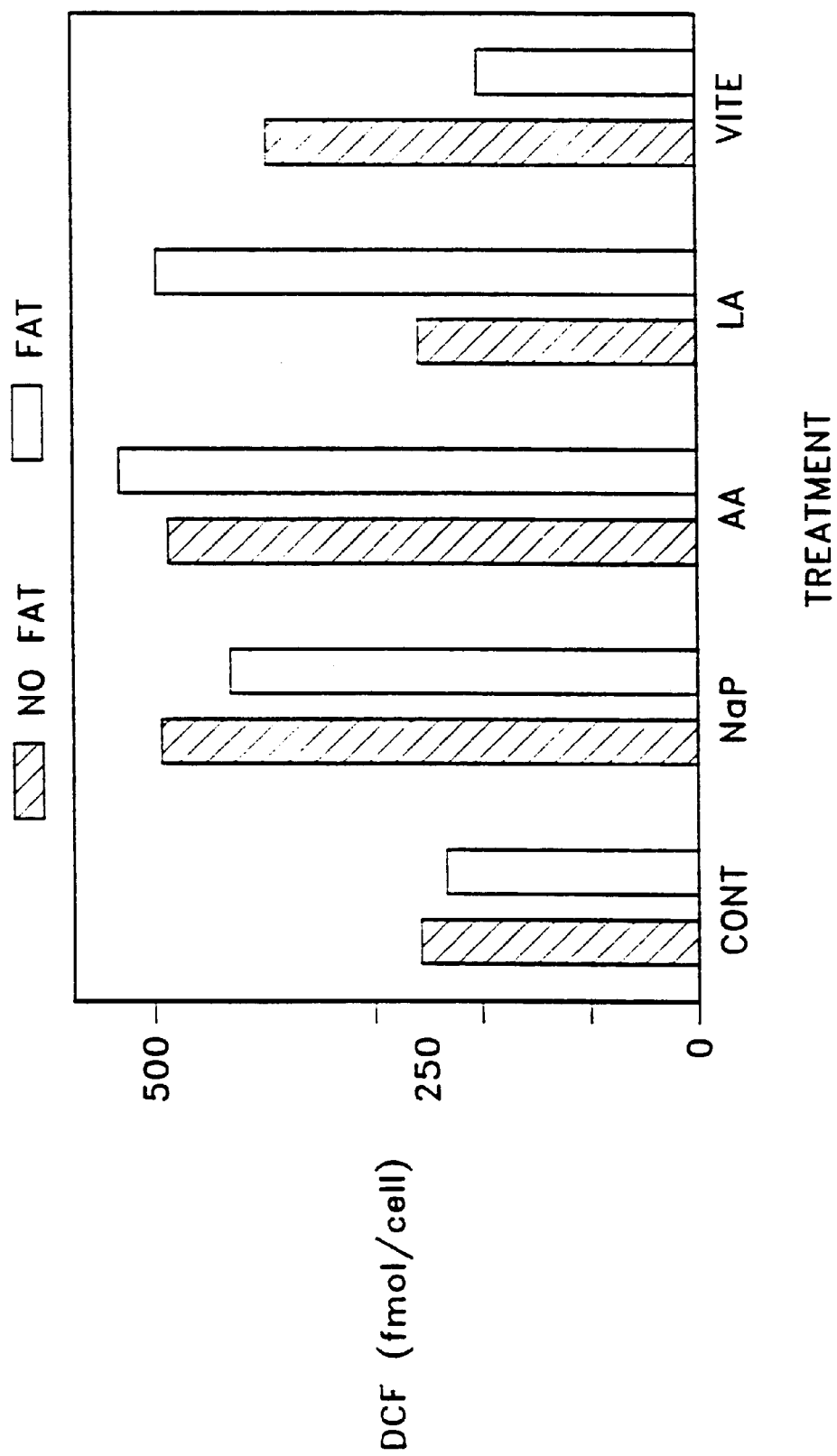
FIG. 6 depicts in bar graph format the levels of hydrogen peroxide produced by epidermal keratinocytes following exposure of the cells to various antioxidants with and without a mixture of saturated and unsaturated fatty acids (Examples 33–42).
Figure 7:
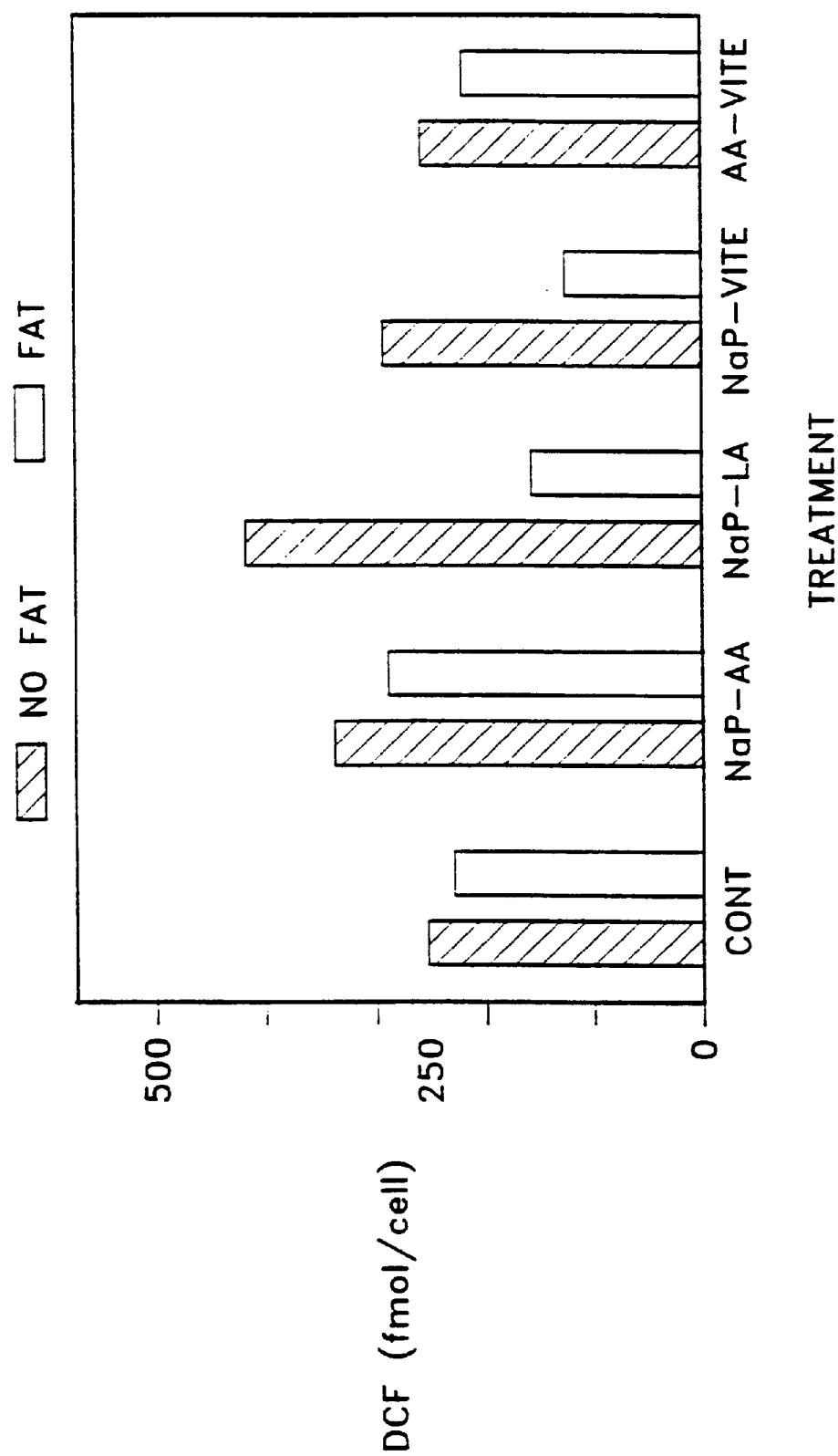
FIG. 7 depicts in bar graph format the levels of hydrogen peroxide produced by epidermal keratinocytes following exposure of the cells to various combinations of antioxidants with and without a mixture of saturated and unsaturated fatty acids (Examples 43–52).

This study demonstrates a comparison of the levels of hydrogen peroxide produced by U937 monocytic cells and epidermal keratinocytes after exposure of the cells to various combinations of antioxidants with and without a mixture of saturated and unsaturated fatty acids. The results of this study are illustrated in FIGS. 5–7 and examples 27–52 below.

Mammalian epidermal keratinocytes and U937 monocytic cells and the test solutions of sodium pyruvate, lactic acid, ascorbic acid, and Vitamin E were prepared as describe above for Examples 1–26. Intracellular hydrogen peroxide production by the mammalian epidermal keratinocytes and U937 monocytes was also measured as described above.

A mixture of fatty acids derived from chicken fat was prepared for addition to the cultured cells by mixing 0.1% of the chicken fat with the culture media. At the temperature of the culture media, 37° C., the chicken fat was miscible. This chicken fat mixture was added to cultures of cells prior to exposure of the cells to ultraviolet-B light or TPA treatment.

As set out in examples 1–26, mammalian epidermal keratinocytes and monocytes were exposed to (a) 1 M.E.D. dose of ultraviolet light-B and (b) 100 ng/ml of 12-O-tetradecanoylphorbol-13-acetate in the presence of various antioxidants and combinations of antioxidants with and without a mixture of saturated and unsaturated fatty acids [0.1%, 0.5%, and 1.0% chicken fat].

FIG. 5 depicts in bar graph format the levels of hydrogen peroxide produced by U937 monocytic cells after exposure of the cells to various combinations of antioxidants with and without a mixture of saturated and unsaturated fatty acids. Specifically, the levels of hydrogen peroxide produced by U937 monocytic cells were measured after exposure to lactic acid and Vitamin E without fatty acids (Example 27) and with fatty acids (Example 28), to ascorbic acid and lactic acid without fatty acids (Example 29) and with fatty acids (Example 30), and to ascorbic acid and Vitamin E without fatty acids (Example 31) and with fatty acids (Example 32). The ability of the combinations of lactic acid and Vitamin E, ascorbic acid and lactic acid, and ascorbic acid and Vitamin E to reduce the hydrogen peroxide production by monocytes was increased in the presence of fatty acids. The most effective combination to reduce the hydrogen peroxide production of monocytes was lactic acid (0.05%) and Vitamin E (50 E) in the presence of a mixture of saturated and unsaturated fatty acids (0.5%).

FIG. 6 depicts in bar graph format the levels of hydrogen peroxide produced by epidermal keratinocytes after exposure of the cells to various antioxidants with and without a mixture of saturated and unsaturated fatty acids. Specifically, the levels of hydrogen peroxide produced by epidermal keratinocytes were measured after exposure to no antioxidant without fatty acids (Example 33, control) and with fatty acids (Example 34), to sodium pyruvate without fatty acids (Example 35) and with fatty acids (Example 36), to ascorbic acid without fatty acids (Example 37) and with fatty acids (Example 38), to lactic acid without fatty acids (Example 39) and with fatty acids (Example 40), and to Vitamin E without fatty acids (Example 41) and with fatty acids (Example 42). The ability of sodium pyruvate and Vitamin E to reduce the hydrogen peroxide production by epidermal keratinocytes was increased in the presence of fatty acids. The most effective combinations to reduce the hydrogen peroxide production of epidermal keratinocytes were sodium pyruvate in combination with a mixture saturated and unsaturated fatty acids and Vitamin E in combination with a mixture of saturated and unsaturated fatty acids.

FIG. 7 depicts in bar graph format the levels of hydrogen peroxide produced by epidermal keratinocytes after exposure of the cells to various combinations of antioxidants with and without a mixture of saturated and unsaturated fatty acids. Specifically, the levels of hydrogen peroxide produced by epidermal keratinocytes were measured after exposure to no antioxidant without fatty acids (Example 43, control) and with fatty acids (Example 44), to sodium pyruvate and ascorbic acid without fatty acids (Example 45) and with fatty acids (Example 46), to sodium pyruvate and lactic acid without fatty acids (Example 47) and with fatty acids (Example 48), to sodium pyruvate and Vitamin E without fatty acids (Example 49) and with fatty acids (Example 50), and to ascorbic acid and Vitamin E without fatty acids (Example 51) and with fatty acids (Example 52). The ability of all combinations of antioxidants to reduce the hydrogen peroxide production by epidermal keratinocytes was increased in the presence of fatty acids. In order of potency, the most effective combinations to reduce the hydrogen peroxide production of epidermal keratinocytes were sodium pyruvate and Vitamin E, sodium pyruvate and lactic acid, and Vitamin E, each in combination with a mixture of saturated and unsaturated fatty acids (0.5%).

Because of the cytotoxicity of cells towards ascorbic acid described above, the ascorbic acid combinations without sodium pyruvate were not considered significantly different from the control test solution.

Summary Analysis Of The Data From Studies 1 and 2

Human epidermal keratinocytes were isolated by trypsinization of epithelial sheets and grown in modified base MCDB 153 medium supplemented with epidermal growth factor and bovine pituitary extract. Cells were seeded in culture dishes at a density of $3\times10^5$ dish. Prior to exposure to UV B light (100 mJ/cm$^2$) or treatment with 100 ng/ml TPA, the cultures were treated with the appropriate concentration of wound healing components. Intracellular production of hydrogen peroxide was measured using DCFH-DA, a nonpolar compound that readily diffuses into cells, hydrolyzed to a polar derivative. In the presence of intracellular hydrogen peroxide, DCFH is oxidized to a highly fluorescent compound DCF. Thus, cellular fluorescence intensity is directly proportional to levels of hydrogen peroxide produced and can be monitored by flow cytometry. Hydrogen peroxide is cytotoxic, therefore lower levels of hydrogen peroxide production is desirable for cellular viability.

In all cases, the three component wound healing composition surpassed the predicted outcomes, clearly demonstrating unpredicted synergy.

| | Results | | |
|---|---|---|---|
| 1 | 2 | 3 | 4 |
| 1-Control | 250 | 250 | 0 |
| 2-Fatty Acids (0.5%) | 250 | 230 | −20 |
| 3-Sodium Pyruvate (10 mM) | 250 | 490 | +240 |
| 4-Vitamin E (50 units) | 250 | 400 | +150 |
| 5-Pyruvate & Fatty Acids | 250 | 430 | +180 |
| 6-Vitamin E & Fatty Acids | 250 | 200 | −50 |
| 7-Pyruvate & Vitamin E | 250 | 290 | +40 |
| 8-Pyruvate & Vitamin E & Fatty Acids (wound healing compositon) | 250 | 120 | −130 |

Column 1 shows the different treatment groups.
Column 2 shows the production of $H_2O_2$ in control cells (fmol/cell).
Column 3 shows the production of $H_2O_2$ after treatment with wound healing components.
Column 4 shows the difference in production of $H_2O_2$ from control after the treatment.

All comparisons were assessed against the controls, which produced 250 $H_2O_2$ fmol/cell. The positive numbers represent $H_2O_2$ production in excess of the control and the negative numbers represent $H_2O_2$ production below the control. These results are set out in FIG. 8.

Combination of Single Ingredient Effects
Fatty Acids (−20) & Vitamin E (+150) & Pyruvate (+240)
  +370 Is The Predicted Three Component Effect
  −130 Is The Wound healing composition Actual Effect
  500 Is The Difference Between Predicted Effect minus Actual effect
  (Synergy)

Combination of Paired and Single Ingredients
Pyruvate & Fatty Acids (+180) & vitamin E (+150)
  +330 Is The Predicted Predicted Three Component Effect
  −130 Is The Wound healing composition Actual Effect
  460 Is The Difference between Predicted Effect minus Actual Effect
  (Synergy)

Vitamin E & Fatty Acids (−50) & Pyruvate (+240)
  +190 Is The Predicted Three Component Effect
  −130 Is The Wound healing composition Actual Effect
  320 Is The Difference between Predicted Effect minus Actual Effect (Synergy)

Pyruvate & Vitamin E (+40) & Fatty Acids (−20)

+20 Is The Predicted Three Component Effect

−130 Is The Wound healing composition Actual Effect

150 Is The Difference between Predicted Effect minus Actual Effect (Synergy)

In all cases, the three component wound healing composition surpassed the predicted outcomes clearly demonstrating unpredicted synergy.

E. (continued) Examples Of The Wound Healing Compositions Of Embodiment One (I.A–D)

Study 3

This study demonstrates a comparison of the wound healing abilities of the therapeutic wound healing compositions of the present invention versus conventional wound healing compositions. The results of this study are illustrated in examples A–D.

The wound healing compositions of Examples A–D were prepared having the compositions set out in Table A.

TABLE A

| | Examples | | | |
|---|---|---|---|---|
| Ingredient | A PREP.-H™ | B | C | D |
| sodium pyruvate | - | 2% | - | - |
| vitamin E | -- | 1% | -- | -- |
| chicken fat | -- | 2% | -- | -- |
| LYCD | 2000 U* | 2400 U | 2400 U | -- |
| shark liver oil | 3%* | 3% | 3% | -- |
| petrolatum | in amounts | 64% | 66.5% | 68% |
| mineral oil | totaling | 22.53% | 25.03% | 26.8% |
| paraffin | 100%* | 5% | 5% | 5% |
| emulsifier | | 0.2% | 0.2% | 0.2% |

* These components are present in PREPARATION H ®

Wound healing composition A was commercially available PREPARATION H®. Wound healing composition B was a petrolatum base formulation containing live yeast cell derivative, shark oil, and a mixture of sodium pyruvate, vitamin E, and chicken fat. Wound healing composition C was a petrolatum base formulation containing live yeast cell derivative and shark oil. Wound healing composition D was a petrolatum base formulation only.

Wound healing studies were carried out using hairless mice (SKR-1, Charles River) 6–8 weeks in age. One group of mice were untreated as a control group and were referred to as Example E. In each group there were 6 mice for evaluation at either day 3 or day 7 for a total number of 60 animals in the study. The mice were anesthetized with ether and a midline 3 cm full thickness longitudinal incision was made with a number 10 scalpel blade. Incisions were closed using steel clips at 1 cm intervals. Formulations A–D set out above were applied in a randomized blinded study to the wounds on day 0 at 2 hours following wounding and reapplied at 24 hour intervals during the 7 days of the study. The wounds were examined daily and scored on a basis of 0–5 for closure on each day of the study, with a score of 5 representing the wound best healed.

The animals were sacrificed on day 3 and day 7 using cervical dislocation. The dorsal skin including the incision was dissected without the subcutaneous tissue. The skin was placed in neutral buffered formalin and subsequently sectioned and stained with hematoxylin and eosin. The wounds were examined microscopically and representative tissue sections were photographed. Wound healing was graded subjectively.

On each day of the experiment, the score and rank order of the formulations for closure of wounds and speed of healing were as follows:

B(5)>>D(4)>>C(2)>/=E, Control (2)>A(1)

Formulation B, which was a petrolatum base formulation containing live yeast cell derivative, shark oil, and a mixture of sodium pyruvate, vitamin E, and chicken fat, was a significantly better wound healing agent than the other formulations. These results are based on the subjective grading of the wound closures and the speed of healing on each day (1–7) of the experiment as well as the objective histological examination of tissue sections to measure the extent of inflammatory cell infiltrate within the wound and the extent of epithelialization at the wound edges. The final result was that less scar tissue was present at 5 day 7 on the mice treated with Formulation B.

Formulation D, which was a white petrolatum formulation only, was judged to be significantly more effective to promote healing than either Formulation C, which was a petrolatum base formulation containing shark liver oil and live yeast cell derivative, or Formulation A, which was PREPARATION H®. The superior ability of Formulation D over Formulation C to improve healing may result from a delay in the healing process caused when the live yeast cell derivative is depleted and the cells shift to an alternative nutrient source. The presence of the mixture of sodium pyruvate, vitamin E, and chicken fat in Formulation B apparently offsets the depletion of the live yeast cell derivative.

Formulation C, which was a petrolatum base formulation containing live yeast cell derivative and shark oil, was judged comparable to the control (untreated wound) in speed of wound closure and extent of healing. Formulation A, which was PREPARATON H®, appeared to be the least effective healing formulation by both subjective grading of wound healing and by objective examination of tissue sections. The superior ability of Formulation D and Formulation C over Formulation A to improve healing may be due to their ability to act as an occlusive wound dressing that prevents transepidermal water loss and thus promotes healing and wound closure. The poor ability of Formulation A to improve healing may be due to the potential cytotoxicity of phenylmercuric nitrate present in PREPARATION H® as a preservative.

These results show that the wound healing compositions of the present invention which comprise a mixture of sodium pyruvate, vitamin E, and chicken fat increase the proliferation and resuscitation rate of mammalian cells. The wound healing compositions mediate low levels of oxygen in the initial stages of healing to suppress oxidative damage and higher levels of oxygen in the later stages of healing to promote collagen formation.

2. The TGF-beta-Wound Heating Compositions

A. Embodiment Two (II.A–D+GF)

As set out above, applicant has discovered therapeutic TGF-beta-wound healing compositions (II.A–D+GF) which comprise a TGF-beta (GF) and the wound healing compositions of Embodiment One (I.A–D). Preferably, the wound healing composition (I.A) comprises (a) pyruvate, (b) an antioxidant, and (c) a mixture of saturated and unsaturated fatty acids. Applicant believes that the combination of a TGF-beta and a wound healing composition results in a therapeutic TGF-beta-wound healing composition which reduces the formation of scar tissue.

More than two dozen peptides structurally related to TGF-beta appear of crucial importance in the regulation of cell proliferation, cell differentiation, and embryogenesis. TGF-beta 1 and its close homologs, TGF-beta 2–5, are multifunctional peptides, the effects of which on cell functions are dependent upon the cell type, the environment, and the presence of other growth factors. TGF-beta is defined by its ability to induce growth and a transformed phenotype in NRK fibroblasts in the presence of TGF-alpha (or EGF). The name transforming growth factor is misleading because TGF-beta actually inhibits the proliferation of many cell types and the "transforming" activity may be explained by secondary effects through extracellular matrix production and synthesis of other growth factors. The cloning of TGF-beta 1 has lead to the identification of a number of structurally related but functionally distinct peptides.

Mature active TGF-beta 1 is a homodimer of 25 kD, made of two identical 112 amino acid subunits bound together by a disulfide link. TGF-beta 2–5 are highly (75–85%) homologous structures, With a conserved domain containing six cysteines arranged in an intra-subunit cysteine knot and a seventh one engaged in the dimer bonding. Based on sequence conservation in the C-terminal domain of this TGF-beta 2–5 family, more than two dozen related peptides have been recognized, leading to the term, the TGF-beta superfamily.

Studies of the biological activities of the TGF-betas have mainly focused on TGF-beta 1. More recent data shows that TGF-beta 1–5 exhibit biological effects which appear qualitatively similar. TGF-beta 1 may stimulate or inhibit proliferation, depending upon the nature of the target cells. In addition, on the same type of cell, the effect of TGF-beta is dependent upon the cell differentiation state and the set of growth factors present in the cell environment. TGF-beta 1 is a multi-functional protein found in all mammalian tissues and has been implicated in the control of development, growth, immune system function, and carcinogenesis.

The transforming growth factors-beta (TGF-beta, TGF-B) in the TGF-beta-wound healing compositions of the present invention may be any TGF-beta known in the art which has the therapeutic wound healing and reduction of scar formation properties of the transforming growth factors family. Preferably, the TGF-beta is selected from the group consisting of Type 1 TGF-beta (TGF-beta 1), Type 2 TGF-beta (TGF-beta 2), Type 3 TGF-beta (TGF-beta 3), Type 4 TGF-beta (TGF-beta 4), and Type 5 TGF-beta (TGF-beta 5). More preferably, the TGF-beta is selected from the group consisting of TGF-beta 1, TGF-beta 2, and TGF-beta 3. More preferably, the TGF-beta is TGF-beta 1. The TGF-betas may be administered in sustained release or prolonged action form.

The TGF-β used in the present invention may be derived from platelets or any other mammalian tissue employing methods known in the art. Additionally, purified TGF-β produced from recombinant cell cultures is also suitable for purposes of the present invention. Since TGF-β is not species specific it is within the scope of the present invention to employ TGF-β from animal sources other than human, for example porcine or bovine sources. TGF-β is discussed in more detail in European Patent Application EP 128849 (Dec. 19, 1984), European Patent Application EP322842-A (Jul. 12, 1989), JP61219395 (Sep. 29, 1980), JP63028386 (Feb. 6, 1988), and PCT application WO 8911293-A (Nov. 30, 1989), and E. M. Chainbaz, Horm. Res. 1996:45, 222–226, which disclosures are incorporated herein by reference.

The TGF-β compositions to be used in the present invention can be formulated and dosed in a fashion consistent with good medical practice taking into consideration the disorder to be treated, the condition of the individual patient, the site of delivery of the TGF-β, the method of administration, and other factors known to practitioners. TGF-β is prepared for administration by mixing TGF-β at the desired degree of purity with physiologically acceptable carriers, carriers which are nontoxic to recipients at the dosages and concentrations employed. Ordinarily, this administration will entail combining TGF-β with buffers, low molecular weight (less than about 10 residues) polypeptides, proteins, amino acids, carbohydrates including glucose or dextrans, chelating agents such as EDTA, and other excipients. TGF-β for use in therapeutic administration must be sterile. This is readily accomplished by sterile filtration through membranes known in the art for this purpose. TGF-β ordinarily will be stored as an aqueous solution since it is highly stable to thermal and oxidative denaturation, although lyophilized formulations for reconstitution are acceptable.

The amount of TGF-beta used in the present invention may vary depending upon the therapeutic dosage recommended or permitted for the particular TGF-beta. In general, the amount of TGF-beta present is the ordinary dosage required to obtain the desired result. Such dosages are known to the skilled practitioner in the medical arts and are not a part of the present invention. In a preferred embodiment, the TGF-beta in the TGF-beta-wound healing composition should be formulated and delivered to the target site at a dosage capable of establishing in the tissue a TGF-β level greater than about 0.25 ng/gram tissue. Typically, the TGF-β concentrations at or near the target site should range from about 0.25 to about 5.0 ng/gram tissue. These intra-tissue concentrations should be maintained if possible over the treatment period by continuous infusions, sustained release formulations or pegylation or by injection at empirically determined frequencies.

The TGF-beta of the present invention may be used in many distinct physical forms well known in the pharmaceutical art to provide an initial dosage of the TGF-beta and/or a further time-release form of the TGF-beta. Without being limited thereto, such physical forms include free forms and encapsulated forms, and mixtures thereof.

B. Methods For Making The TGF-beta-Wound Healing Compositions Of Embodiment Two (II.A–D+GF)

The present invention extends to methods for making the therapeutic TGF-beta-wound healing compositions (II.A–D+GF). In general, a therapeutic TGF-beta-wound healing composition is made by forming an admixture of the wound healing components of Embodiment One (I.A–D) and a TGF-beta. In a first aspect of Embodiment Two (II.A+GF), a TGF-beta-wound healing therapeutic composition is made by forming an admixture of a TGF-beta and a wound healing composition comprising (a) a pyruvate, (b) an antioxidant, and (c) a mixture of saturated and unsaturated fatty acids. In a second aspect of Embodiment Two (II.B+GF), a TGF-beta-wound healing therapeutic composition is made by forming an admixture of a TGF-beta and a wound healing composition comprising (a) a pyruvate, (b) a lactate, and (c) a mixture of saturated and unsaturated fatty acids. In a third aspect of Embodiment Two (II.C+GF), a TGF-beta-wound healing therapeutic composition is made by forming an admixture of a TGF-beta and a wound healing composition comprising (a) an antioxidant and (b) a mixture of saturated and unsaturated fatty acids. In a fourth aspect of Embodiment Two (II.D+GF), a TGF-beta-wound healing therapeutic composition is made by forming an admixture of a TGF-beta and a wound healing composition comprising (a) a lactate, (b) an antioxidant, and (c) a mixture of saturated and unsaturated fatty acids.

In a preferred embodiment, the invention is directed to a method for preparing a therapeutic TGF-beta-wound healing composition (II.A+GF) which comprises the steps of admixing the following ingredients:
(A) a therapeutically effective amount of a TGF-beta; and
(B) a wound healing composition which comprises:
  (a) pyruvate selected from the group consisting of pyruvic acid, pharmaceutically acceptable salts of pyruvic acid, and mixtures thereof;
  (b) an antioxidant; and
  (c) a mixture of saturated and unsaturated fatty acids wherein the fatty acids are those fatty acids required for the repair of cellular membranes and resuscitation of mammalian cells.

C. Methods For Employing The TGF-beta-Wound Healing Compositions Of Embodiment Two (II.A–D+GF)

The present invention extends to methods for employing the therapeutic TGF-beta-wound healing compositions (II.A–D+GF). In general a therapeutic composition is employed by contacting the therapeutic composition with a wound. In a preferred embodiment, the invention is directed to a method for healing an infected wound in a mammal with a TGF-beta-wound healing composition (II.A+GF) which comprises the steps of:
(A) providing a therapeutic TGF-beta-wound healing composition which comprises:
  (1) a therapeutically effective amount of a TGF-beta; and
  (2) a wound healing composition which comprises:
    (a) pyruvate selected from the group consisting of pyruvic acid, pharmaceutically acceptable salts of pyruvic acid, and mixtures thereof;
    (b) an antioxidant; and
    (c) a mixture of saturated and unsaturated fatty acids wherein the fatty acids are those fatty acids required for the repair of cellular membranes and resuscitation of mammalian cells; and
(B) contacting the TGF-beta-wound healing composition with the infected wound.

D. The Augmented TGF-beta-Wound Healing Compositions Of Embodiment Two (II.A–D+GF+M)

In another aspect of Embodiment Two, the therapeutic TGF-beta-wound healing compositions (II.A–D+GF) of the present invention may be combined with medicaments useful for treating wounds (M) to form augmented TGF-beta-wound healing compositions (II.A–D+GF+M). In this embodiment, the combination of the TGF-beta-wound healing composition of the present invention and the medicament useful for treating wounds provides an augmented TGF-beta-wound healing composition having an enhanced ability to increase the proliferation and resuscitation rate of mammalian cells. For example, the therapeutic compositions of the present invention may be used in combination with medicaments useful for treating wounds such as immunostimulating agents, other TGF-betas, antikeratolytic agents, anti-inflammatory agents, antifungal agents, respiratory bursting inhibitors (lactic acid, adenosine), inhibitors of prostaglandin synthesis (ibuprofen, aspirin, indomethacin, meclofenomic acid, retinoic acid, padimate O, meclomen, oxybenzone), steroidal anti-inflamrnatory agents (corticosteroids including synthetic analogs), antimicrobial agents (neosporin ointment, silvadine), antiseptic agents, anesthetic agents (pramoxine hydrochloride, lidocaine, benzocaine), cell nutrient media, burn relief medications, sun burn medications, sunscreen agents, acne preparations, tretinoin, insect bite and sting medications, wound cleansers, wound dressings, scar reducing agents (vitamin E), dermatological agents, antihistamine agents, antibacterial agents, and mixtures thereof to further enhance the proliferation and resuscitation rate of mammalian cells. Preferably, the medicaments useful for treating wounds are selected from the group consisting of cytotoxic agents, other TGF-betas, antikeratolytic agents, anti-inflammatory agents, antifungal agents, tretinoin, sunscreen agents, a buffering agent to maintain the pH of dermatitis in a range from about 5 to about 8 togetlier with an anti-inflammatory agent, topical antihistamine agents, antibacterial agents, respiratory bursting inhibitors, inhibitors of prostaglandin synthesis, antimicrobial agents, cell nutrient media, scar reducing agents, and mixtures thereof.

Nonlimiting illustrative examples of immunostimulating agents may be selected from the group consisting of betafectin® and Freund's complete adjuvant. Nonlimiting illustrative examples of cytotoxic agents may be selected from the group consisting of epithelial cell cohesiveness reducers, dermatological abradants, anti-inflammatories, lipid regulating agents, centrally acting anticholinesterases, chemotherapeutic drugs, and gastric irritants. Nonlimiting illustrative examples of antiviral agents may be selected from the group consisting of acyclovir, foscarnet sodium, ribavirin, vidarabine, ganeiclovir sodium, zidovudine, phenol, amantadine hydrochloride, and interferon alfa-n3. Nonlimiting illustrative examples of antikeratolytic agents may be selected from the group consisting of salicylic acid, lactic acid, and urea. Nonlimiting illustrative examples of anti-inflammatory agents may be selected from the group consisting of ibuprofen, naproxen, sulindac, diflunisal, piroxicam, indomethacin, etodolac, meclofenamate sodium, fenoproben calcium, ketoprofen, mefenamic acid, nabumetone, ketorclac tromethamine, diclofenac, evening primrose oil, acetylsalicylic acid, mesalamine, salsalate, diflunisal, salicylsalicylic acid, choline magnesium trisalicylate, flunisolide, triamcinoline, triamcinoline acetonide, beclomethasone diprorionate, betamethasone diprorionate, hydrocortisone, cortisone, dexamethasone, prednisone, methyl prednisolone, and prednisolone. Nonlimiting illustrative examples of antifungal agents may be selected from the group consisting of lactic acid, sorbic acid, miconazole, clotrimazole, tioconazole, terconazole, povidone-iodine, and butoconazole. Nonlimiting illustrative examples of sunscreen agents may be selected from the group consisting of ethvlhexyl p-methoxycinnamate, octyl methoxycinnamate, octyl dimethyl p-aminobenzoic acid, 2-ethylhexyl salicylate, octyl salicylate, menthyl anthranilate, octocrylene, padimate o, titanium dioxide, urea, and oxybenzone. Nonl.miting illustrative examples of topical antihistamine agents may be selected from the group consisting of diphenhydramine hydrochloride and pramoxine hydrochloride. Nonlimiting illustrative examples of antibacterial agents may be selected from the group consisting of bismuth compounds, such as bismuth aluminate, bismuth subcitrate, bismuth subgalate, bismuth subsalicylate; the sulfonamides; the nitrofurans, such as nitrofurazone and nitrofurantoin; furazolidone, metronidazole, tinidazole, nimorazole, benzoic acid, the aminoglycosides; such as gentamicin, neomycin, kanamycin, and streptomycin; the macrolides, such as erythromycin, clindamycin, and rifamycin; the penicillins, such as penicillin G, penicillin V, Ampicillin and amoxicillin; the polypeptides, such as bacitracin and polymyxin; the tetracyclines, such as tetracycline, chlorotetracycline, oxytetracycline, and doxycycline; the cephalosporins, such as cephalexin and cephalothin; and chloramphenicol, and clidamycin.

In a preferred embodiment, the invention is directed to an augmented TGF-beta-wound healing composition (II.A+GF+M) which comprises:
(A) a therapeutic TGF-beta-wound healing composition which comprises:
  (1) a therapeutically effective amount of a TGF-beta; and
  (2) a wound healing composition which comprises:
    (a) pyruvate selected from the group consisting of pyruvic acid, pharmaceutically acceptable salts of pyruvic acid, and mixtures thereof;
    (b) an antioxidant, and
    (c) a mixture of saturated and unsaturated fatty acids wherein the fatty acids are those fatty acids required for the repair of cellular membranes and resuscitation of mammalian cells; and
(B) a medicament useful for treating wounds.

The present invention extends to methods for making the augmented TGF-beta-wound healing compositions. In general, the augmented compositions are made by admixing the therapeutic TGF-beta-wound healing composition with the medicament useful for treating wounds to prepare the augmented TGF-beta-wound healing composition.

The present invention also extends to methods for employing the augmented TGF-beta-wound healing compositions. In general, an augmented TGF-beta-wound healing composition is employed by contacting the composition with a wound. In a preferred embodiment, the invention is directed to a method for healing an infected wound in a mammal with an augmented TGF-beta-wound healing composition (II.A+GF+M) which comprises the steps of:
(A) providing a therapeutic augmented TGF-beta-wound healing composition which comprises:
  (1) a therapeutically effective amount of a TGF-beta;
  (2) a wound healing composition which comprises:
    (a) pyruvate selected from the group consisting of pyruvic acid, pharmaceutically acceptable salts of pyruvic acid, and mixtures thereof;
    (b) an antioxidart; and
    (c) a mixture of saturated and unsaturated fatty acids wherein the fatty acids are those fatty acids required for the repair of cellular membranes and resuscitation of mammalian cells; and
  (3) providing a medicament useful for treating wounds; and
(B) contacting the augmented TGF-beta-wound healing composition with the infected wound.

The types of wounds which may be healed using the TGF-beta-wound healing compositions and the augmented TGF-beta-wound healing compositions of the present invention are those which result from an infected injury which causes epidermal damage. The topical therapeutic compositions may be used orally in the form of a mouth wash or spray to protect and accelerate the healing of injured oral tissue.

Methods for healing a wound comprise topically administering the compositions of the present invention directly to a wound site to increase the healing rate of the wound. The composition is maintained in contact with the wound for a period of time sufficient to increase the proliferation and resuscitation rate of the cells.

E. Formulations Of The TGF-beta-Wound Healing Compositions Of Embodiment Two (II.A–D+GF)

Once prepared, the inventive therapeutic TGF-beta-wound healing compositions and augmented TGF-beta-wound healing compositions may be stored for future use or may be formulated in effective amounts with pharmaceutically acceptable carriers such as pharmaceutical appliances and topical vehicles (oral and non-oral) to prepare a wide variety of pharmaceutical compositions. The pharmaceutically acceptable carriers which may be employed and the methods used to prepare the pharmaceutical compositions have been described above in connection with the formulations of the wound healing compositions of Embodiment One (I.A–D).

In a preferred embodiment, the invention is directed to a TGF-beta-wound healing pharmaceutical composition which comprises:
(A) a therapeutic TGF-beta-wound healing composition (II.A+GF) which comprises:
  (1) a therapeutically effective amount of a TGF-beta; and
  (2) a wound healing composition which comprises:
    (a) pyruvate selected from the group consisting of pyruvic acid, pharmaceutically acceptable salts of pyruvic acid, and mixtures thereof;
    (b) an antioxidant; and
    (c) a mixture of saturated and unsaturated fatty acids wherein the fatty acids are those fatty acids required for the repair of cellular membranes and resuscitation of mammalian cells; and
(B) a pharmaceutically acceptable carrier selected from the group consisting of pharmaceutical appliances, bioadhesives, and occlusive vehicles.

In another preferred embodiment, the invention is directed to a method for preparing a pharmaceutical composition for increasing the proliferation and resuscitation rate of mammalian cells, which comprises the steps of:
(A) providing a therapeutically effective amount of a TGF-beta-wound healing composition (II.A+GF) which comprises:
  (1) a TGF-beta; and
  (2) a wound healing composition comprising:
    (a) pyruvate selected from the group consisting of pyruvic acid, pharmaceutically acceptable salts of pyruvic acid, and mixtures thereof;
    (b) an antioxidant; and
    (c) a mixture of saturated and unsaturated fatty acids wherein the fatty acids are those fatty acids required for the repair of cellular membranes and resuscitation of mammalian cells;
(B) providing a pharmaceutically acceptable carrier; and
(C) admixing the TGF-heta-wound healing composition from step (A) and the pharmaceutically acceptable carrier from step (B) to form a pharmaceutical composition.

The invention being thus described, it will be obvious that the same may be varied in many ways. Such variations are not to be regarded as a departure from the spirit and scope of the invention and all such modifications are intended to be included within the scope of the following claims.

We claim:

1. A therapeutic TGF-beta-wound healing composition which comprises a therapeutically effective amount of a TGF-beta and a wound healing composition, wherein the wound healing composition comprises:
   (a) pyruvate selected from the group consisting of pyruvic acid, pharmaceutically acceptable salts of pyruvic acid, and mixtures thereof;
   (b) an antioxidant; and
   (c) a mixture of saturated and unsaturated fatty acids wherein the fatty acids are those fatty acids required for the resuscitation of injured mammalian cells; wherein components a, b, and c are present in amounts sufficient to synergistically enhance wound healing.

2. The composition according to claim 1, wherein the TGF-beta is selected from the group consisting of Type 1 TGF-beta, Type 2 TGF-beta, and Type 3 TGF-beta.

3. The composition according to claim 2, wherein the TGF-beta is Type 1 TGF-beta.

4. The composition according to claim 1, wherein the pyruvate is selected from the group consisting of pyruvic acid, lithium pyruvate, sodium pyruvate, potassium pyruvate, magnesium pyruvate, calcium pyruvate, zinc pyruvate, manganese pyruvate, methyl pyruvate, α-ketoglutaric acid, pharmaceutically acceptable salts of pyruvic acid, prodrugs of pyruvic acid, and mixtures thereof.

5. The composition according to claim 4, wherein the pyruvate is sodium pyruvate.

6. The composition according to claim 1, wherein the antioxidant is selected from the group consisting of all forms of Vitamin A; all forms of carotene;; all forms of Vitamin C; all forms of Vitamin E; Vitamin E esters which readily undergo hydrolysis to Vitamin E; prodrugs of Vitamin A, carotene, Vitamin C, and Vitamin E; pharmaceutically acceptable salts of Vitamin A, carotene, Vitamin C, and Vitamin E, and mixtures thereof.

7. The composition according to claim 6, wherein the antioxidant is Vitamin E acetate.

8. The composition according to claim 1, wherein the mixture of saturated and unsaturated fatty acids comprises animal and vegetable fats and waxes.

9. The composition according to claim 8, wherein the mixture of saturated and unsaturated fatty acids is selected from the group consisting of human fat, chicken fat, cow fat, sheep fat, horse fat, pig fat, and whale fat.

10. The composition according to claim 9, wherein the mixture of saturated and unsaturated fatty acids comprises lauric acid, myristic acid, myristoleic acid, pentadecanoic acid, palmitic acid, palmitoleic acid, margaric acid, margaroleic acid, stearic, oleic acid, linoleic acid, linolenic acid, arachidic acid, and gadoleic acid.

11. The composition according to claim 1, wherein the TGF-beta is present in the therapeutic wound healing composition in an amount capable of establishing in the tissue a TGF-3 level greater than about 0.25ng/gram tissue.

12. The composition according to claim 1, wherein pyruvate is present in the therapeutic wound healing composition in an amount from about 10% to about 50%, by weight of the therapeutic wound healing composition.

13. The composition according to claim 1, wherein the antioxidant is present in the therapeutic wound healing composition in an amount from about 0.1% to about 40%, by weight of the therapeutic wound healing composition.

14. The composition according to claim 1, wherein the mixture of saturated and unsaturated fatty acids is present in the therapeutic wound healing composition in an amount from about 10% to about 50%, by weight of the therapeutic wound healing composition.

15. A method for treating a wound in a mammal which comprises administering to a mammal in need thereof: a therapeutic TGF-beta-wound healing composition which comprises:
   (1) a TGF-beta; and
   (2) a therapeutically effective amount of a wound healing composition comprising:
      (a) pyruvate selected from the group consisting of pyruvic acid, pharmaceutically acceptable salts of pyruvic acid, and mixtures thereof;
      (b) an antioxidant; and
      (c) a mixture of saturated and unsaturated fatty acids wherein the fatty acids are those fatty acids required for the repair of cellular membranes and resuscitation of mammalian cells;
   wherein components a, b, and c are present in amounts sufficient to enhance wound.

16. A method for preparing a therapeutic TGF-beta-wound healing composition which comprises the steps of admixing the following ingredients:
   (1) a TGF-beta; and
   (2) a therapeutically effective amount of a wound healing composition comprising:
      (a) pyruvate selected from the group consisting of pyruvic acid, pharmaceutically acceptable salts of pyruvic acid, and mixtures thereof;
      (b) an antioxidant; and
      (c) a mixture of saturated and unsaturated fatty acids wherein the fatty acids are those fatty acids required for the repair of cellular membranes and resuscitation of mammalian cells; wherein components a, b, and c are present in amounts sufficient to synergistically enhance wound healing.

17. An augmented TGF-beta-wound healing composition which comprises:
   (A) a therapeutic TGF-beta-wound healing composition which comprises:
      (1) a therapeutically effective amount of a TGF-beta; and
      (2) a wound healing composition which comprises:
         (a) pyruvate selected from the group consisting of pyruvic acid, pharmaceutically acceptable salts of pyruvic acid, and mixtures thereof;
         (b) an antioxidant; and
         (c) a mixture of saturated and unsaturated fatty acids wherein the fatty acids are those fatty acids required for the repair of cellular membranes and resuscitation of mammalian cells; wherein components a, b, and c are present in amounts sufficient to synergistically enhance wound healing; and,
   (B) a medicament useful for treating wounds.

18. The augmented TGF-beta-wound healing composition according to claim 17, wherein the medicament useful for treating wounds is selected from the group consisting of immunostimulating agents, antiviral agents, antikeratolytic agents, anti-inflammatory agents, antifungal agents, acne treating agents, sunscreen agents, dermatological agents, antihistamine agents, antibacterial agents, respiratory bursting inhibitors, inhibitors of prostaglandin synthesis, antimicrobial agents, antiseptic agents, anesthetic agents, cell nutrient media, burn relief medications, sun burn medications, insect bite and sting medications, wound cleansers, wound dressings, scar reducing agents, and mixtures thereof.

19. The augmented TGF-beta-wound healing composition according to claim 18, wherein the medicament useful for treating wounds is selected from the group consisting of immunostimulating, agents, antiviral agents, antikeratolytic agents, anti-inflammatory agents, antifungal agents, acre treating agents, sunscreen agents, dermatological agents, antihistamine agents, and antibacterial agents.

20. The augmented TGF-beta-wound healing composition according to claim 19, wherein the medicament useful for treating wounds is an immunostimulating agent selected from the group consisting of betafectin® and Freund's complete adjuvant.

21. The augmented TGF-beta-wound healing composition according to claim 17, wherein the medicament useful for treating wounds is a cytotoxic agent selected from the group consisting of epithelial cell cohesiveness reducers, dermatological abradants, anti-inflammatories, lipid regulating agents, centrally acting anticholinesterases, chemotherapeutic drugs, and gastric irritants.

22. The augmented TGF-beta-wound healing composition according to claim 19, wherein the medicament useful for treating wounds is an antiviral agent selected from the group consisting of acyclovir, foscamet sodium, ribavirin, vidarabine, ganeiclovir sodium, zidovudine, phenol, amantadine hydrochloride, and interferon alfa-n3.

23. The augmented TGF-beta-wound healing composition according to claim 19, wherein the medicament useful for treating wounds is an antikeratolytic agent selected from the group consisting of salicylic acid, lactic acid, and urea.

24. The augmented TGF-beta-wound healing composition according to claim 19, wherein the medicament useful for treating wounds is an anti-inflammatory agent selected from the group consisting of ibuprofen, naproxen, sulindac, diflunisal, piroxicam, indomethacin, etodolac, meclofenamate sodium, fenoproben calcium, ketoprofen, mefenamic acid, nabumetone, ketorolac tromethamine, diclofenac, evening primrose oil, acetylsalicylic acid, mesalamine, salsalate, diflunisal, salicylsalicylic acid, choline magnesium trisalicylate, flunisolide, triamcinoline, triamcinoline acetonide, beclomethasone dipropriorate, betamethasone dipropionate, hydrocortisone, cortisone, dexamethasone, prednisone, methyl prednisolone, and prednisolone.

25. The augmented TGF-beta-wound healing composition according to claim 19, wherein the medicament useful for treating wounds is an antifungal agent selected from the group consisting of lactic acid, sorbic acid, miconazole, clotrimazole, tioconazole, terconazole, povidone-iodine, and butoconazole.

26. The augmented TGF-beta-wound healing composition according to claim 19, wherein the medicament useful for treating wounds is tretinoin.

27. The augmented TGF-beta-wound healing composition according to claim 19, wherein the medicament useful for treating wounds is a sunscreen agent selected from the group consisting of ethylhexyl p-methoxycinnamate, octyl methoxycinnamate, octyl dimethyl p-aminobenzoic acid, 2-ethylhexyl salicylate, octyl salicylate, menthyl anthranilate, octocrylene, padimate o, titanium dioxide, urea, and oxybenzone.

28. The augmented TGF-beta-wound healing composition according to claim 19, wherein the medicament useful for treating wounds is a buffering agent to maintain the pH of dermatitis in a range from about 5 to about 8 together with an anti-inflammatory agent.

29. The augmented TGF-beta-wound healing composition according to claim 19, wherein the medicament useful for treating wounds is a topical antihistamine agent selected from the group consisting of diphenhydramine hydrochloride and pramoxine hydrochloride.

30. The augmented TGF-heta-wound healing composition according to claim 19, wherein the medicament useful for treating wounds is an antibacterial agent selected from the group consisting of bismuth compounds, such as bismuth aluminate, bismuth subcitrate, bismuth subgalate, bismuth subsalicylate; the sulfonamides; the nitrofurans, such as nitrofurazone and nitrofurantoin; furazolidone, metronidazole, tinidazole, nimorazole, benzoic acid, the aminoglycosides; such as gentamicin, neomycin, kanamycin, and streptomycin, the macrolides, such as erythromycin, clindamycin, and rifamycin; the penicillins, such as penicillin G, penicillin V, Ampicillin and amoxicillin; the polypeptides, such as bacitracin and polymyxin; the tetracyclines, such as tetracycline, chlorotetracycline, oxytetracycline, and doxycycline; the cephalosporins, such as cephalexin and cephalothin; and chloramphenicol, and clidamycin.

31. A method for treating a wound in a mammal with an augmented TGF-beta-wound healing composition which comprises administering to a mammal in need thereof a therapeutic augmented TGF-beta-wound healing composition which comprises:
(1) a therapeutically effective amount of a TGF-beta;
(2) a wound healing composition which comprises:
(a) pyruvate selected from the group consisting of pyruvic acid, pharmaceutically acceptable salts of pyruvic acid, and mixtures thereof;
(b) an antioxidant; and
(c) a mixture of saturated and unsaturated fatty acids wherein the fatty acids are those fatty acids required for the repair of cellular membranes and resuscitation of mammalian cells; wherein components a, b, and c are present in amounts sufficient to synergistically enhance wound healing; and,
(3) a medicament useful for treating wounds.

32. The method according to claim 31, wherein the medicament useful for treating wounds is selected from the group consisting of immunostimulating agents, antiviral agents, antikeratolytic agents, anti-inflammatory agents, antifungal agents, acne treating agents, sunscreen agents, dermatological agents, antihistamine agents, antibacterial agents, TGF-betas, respiratory bursting inhibitors, inhibitors of prostaglandin synthesis, antimicrobial agents, antiseptic agents, anesthetic agents, cell nutrient media, burn relief medications, sun burn medications, insect bite and sting medications, wound cleansers, wound dressings, scar reducing agents, and mixtures thereof.

33. A TGF-beta-wound healing pharmaceutical composition which comprises:
(A) a therapeutic TGF-beta-wound healing composition which comprises:
(1) a therapeutically effective amount of a TGF-beta; and
(2) a wound healing composition which comprises:
(a) pyruvate selected from the group consisting of pyruvic acid, pharmaceutically acceptable salts of pyruvic acid, and mixtures thereof;
(b) an antioxidant; and
(c) a mixture of saturated and unsaturated fatty acids wherein the fatty acids are those fatty acids required for the repair of cellular membranes and resuscitation of mammalian cells; wherein components a, b, and c are present in amounts sufficient to synergistically enhance wound healing; and,
(B) a pharmaceutically acceptable carrier selected from the group consisting of pharmaceutical appliances, bioadhesives, and occlusive vehicles.

* * * * *